(12) United States Patent
Fujii et al.

(10) Patent No.: US 7,514,452 B2
(45) Date of Patent: Apr. 7, 2009

(54) 2-FURANCARBOXYLIC ACID HYDRAZIDES AND PHARMACEUTICAL COMPOSITIONS CONTAINING THE SAME

(75) Inventors: Akihito Fujii, Ikoma (JP); Toshiyuki Negoro, Osaka (JP); Chiaki Migihashi, Kyoto (JP); Makoto Murata, Hirakata (JP); Keiji Nakamura, Kashiba (JP); Takashi Nukuda, Toyonaka (JP); Takafumi Matsumoto, Takatsuki (JP); Kiyomi Imano, Sakai (JP)

(73) Assignee: Dainippon Pharmaceutical Co., Ltd, Osaka (JP)

( * ) Notice: Subject to any disclaimer, the term of this patent is extended or adjusted under 35 U.S.C. 154(b) by 764 days.

(21) Appl. No.: 10/503,215

(22) PCT Filed: Jan. 30, 2003

(86) PCT No.: PCT/JP03/00871

§ 371 (c)(1),
(2), (4) Date: Jul. 30, 2004

(87) PCT Pub. No.: WO03/064404

PCT Pub. Date: Aug. 7, 2003

(65) Prior Publication Data

US 2005/0171196 A1 Aug. 4, 2005

(30) Foreign Application Priority Data

Feb. 1, 2002 (JP) .............................. 2002-026012

(51) Int. Cl.
*A61K 31/47* (2006.01)
*C07D 307/02* (2006.01)
*C07D 405/00* (2006.01)

(52) U.S. Cl. ...................... 514/314; 514/336; 514/414; 514/471; 549/473; 549/487; 546/152; 546/167; 546/284.7; 548/466

(58) Field of Classification Search ................. 549/473, 549/487; 546/167, 284.7, 152; 548/466; 514/317, 336, 414, 471
See application file for complete search history.

(56) References Cited

U.S. PATENT DOCUMENTS

| | | | | |
|---|---|---|---|---|
| 3,746,703 A | * | 7/1973 | Bruce | 564/150 |
| 3,859,281 A | * | 1/1975 | Bruce | 544/272 |
| 4,334,015 A | * | 6/1982 | Yarian | 503/218 |
| 5,229,038 A | * | 7/1993 | Uchino et al. | 252/582 |
| 5,728,646 A | * | 3/1998 | Tominaga et al. | 503/208 |
| 5,880,139 A | * | 3/1999 | Chang | 514/326 |

FOREIGN PATENT DOCUMENTS

| JP | 48-91061 | 11/1973 |
|---|---|---|
| JP | 11-106371 | 4/1999 |
| WO | WO 99/01423 | 1/1999 |
| WO | WO 00/39088 | 7/2000 |

OTHER PUBLICATIONS

Yakkyoku, Pharmacy, vol. 48 No. 5 pp. 753 (1997).*
Abel, Cur. Drug. Tar. Imm. Endo. Meta. Dis. vol. 5 No. 2 , abstract, (2005).*
Olatunbosun MD, Insulin Resistance eMedicine, pp. 1-10, (2006).*
"Hyperglycemia of Diabetic Rats Decreased by a Glucagon Receptor Antagonist," Science, vol. 215 p. 1115-1116 Feb. 26, 1982.
Unson, et al., "Biological Activities of des-His[1] [Glu[9]]Glucagon Amide, a Glucagon Antagonist[1]," Peptides, vol. 10, p. 1171-1177 1989.
Terlecky J, et al., "The Glucagon Receptor Antagonist ALT 3000 Lowers Fasting Hyperglycemia in Rat Models of Diabetes," 1996, 45, (suppl 2), 220A.
Chemical Abstracts vol. 80, 1974 120745v.

* cited by examiner

*Primary Examiner*—Janet L. Andres
*Assistant Examiner*—Raymond Covington
(74) *Attorney, Agent, or Firm*—Knobbe, Martens, Olson & Bear LLP

(57) ABSTRACT

The present invention provides 2-furancarboxylic acid hydrazide compounds represented by General Formula (I) below, and prodrugs, physiologically acceptable salts, hydrates, solvates thereof:

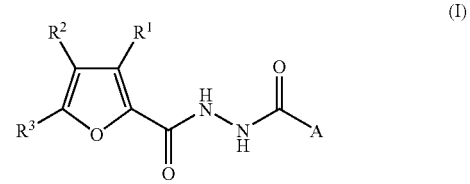

wherein A is a group represented by Formula (a) or the like:

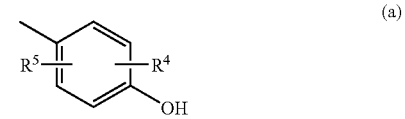

(wherein either $R^4$ or $R^5$ represents cyano, nitro or the like, and the other represents a hydrogen atom or the like); either $R^1$ or $R^2$ represents a group: -D-(X)m-$R^6$ or the like, and the other represents a group: -E-(Y)n-$R^7$, hydrogen atom, aryl or the like; $R^3$ is a hydrogen atom or the like; D and E independently represent aryl; X and Y independently represent O or the like; $R^6$ and $R^7$ independently represent alkyl, aryl, arylalkyl or the like; and m and n are independently 0 or 1, provided that the aryl is optionally substituted.

15 Claims, No Drawings

2-FURANCARBOXYLIC ACID HYDRAZIDES AND PHARMACEUTICAL COMPOSITIONS CONTAINING THE SAME

This application is the U.S. National Phase under 35 U.S.C. §371 of International Application PCT/JP03/00871, filed Jan. 30, 2003, which claims priority to Japanese Patent Application No. 2002-26012, filed Feb. 1, 2002. The International Application was not published under PCT Article 21(2) in English.

TECHNICAL FIELD

The present invention relates to novel 2-furancarboxylic acid hydrazide compounds having an antagonistic activity on glucagon receptor, and pharmaceutical compositions containing such compounds.

BACKGROUND OF THE INVENTION

Blood-sugar levels in humans are controlled by insulin, glucagon, adrenalin, growth hormone, etc. The hyperglycemic state caused by the abnormality of this controlling mechanism is called diabetes mellitus. Diabetes mellitus is categorized into type I diabetes (insulin-dependent diabetes mellitus, or IDDM) and type II diabetes (non-insulin-dependent diabetes mellitus, or NIDDM). Type I diabetes is caused by the absolute decrease of insulin secretion, and type II diabetes is caused by the relative decrease of insulin secretion or the diminished insulin sensitivity of peripheral tissues and the liver. Type II diabetes that is not accompanied by obesity is considered to be typically caused by the decrease of insulin secretion, and type II diabetes that is accompanied by obesity is considered to be typically caused by diminished insulin sensitivity. Moreover, in addition to insulin, glucagon is also considered to be involved in the cause of diabetes mellitus.

Glucagon is a peptide hormone composed of 29 amino acids secreted from the pancreatic islet α-cells. Glucagon raises blood sugar levels by promoting glycogenolysis and glucogenesis. Glucagon is bound to a seven-transmembrane, G protein-coupled receptor present at the cell membrane, and expresses its physiological functions via cAMP as the second messenger.

In type II diabetic patients, blood glucagon levels are increased, and hepatic glucose production is enhanced accordingly, resulting in a high blood sugar condition. This suggests that controlling the function of glucagon could be used to control hepatic glucose production, decreasing blood sugar levels, and ameliorating the high blood sugar conditions of diabetic patients.

It has been reported that peptidergic glucagon receptor antagonists decrease blood sugar levels of diabetic animal models (*Science* 1982, 215, 1115-1116; *Peptides* 1989, 10, 1171-1177; *Diabetes* 1996, 45(Suppl2), 220A). However, it is a problem that the peptidergic glucagon receptor antagonists are susceptible to enzymolysis and do not have activities from oral administration.

Although several nonpeptidergic glucagon receptor antagonists have been proposed, none are used clinically yet. Therefore, it has been strongly desired to develop an excellent nonpeptidergic glucagon.

WO 99/01423 discloses that a hydrazide compound represented by Formula (1) below functions as a glucagon antagonist or an inverse agonist:

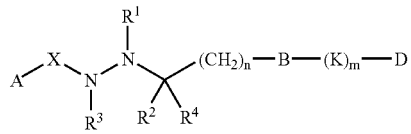

(1)

wherein $R^1$ and $R^2$ are independently hydrogen or lower alkyl, or together form a valence bond;
$R^3$ and $R^4$ independently are hydrogen or lower alkyl;
n is 0, 1, 2 or 3;
m is 0 or 1;
X is $>C=O$, $>C=S$, $>=NR^5$ or $>SO_2$;
A is a group represented by one of the following groups:

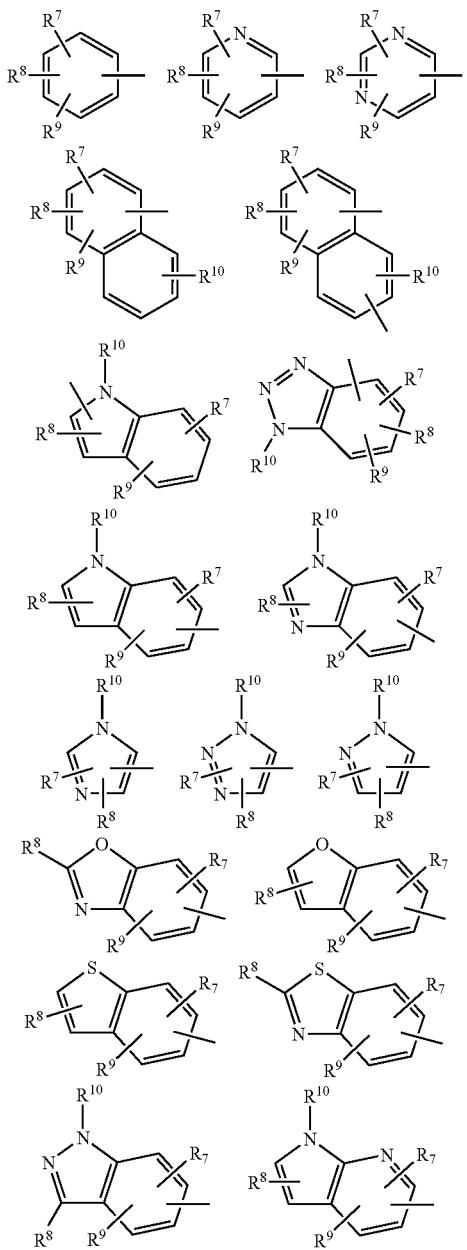

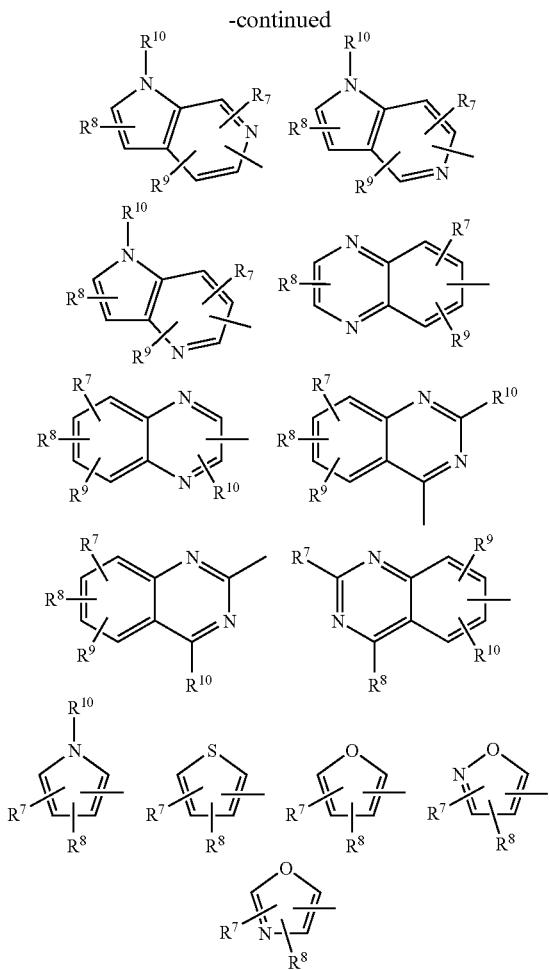

(wherein R⁷ is hydrogen, halogen, —CN, —CF₃, —OCF₃, —OCH₂CF₃, —NO₂, —OR¹¹, —NR¹¹R¹², lower alkyl, aryl, aryl-lower alkyl, —SCF₃, —SO₂NR¹¹R¹², —SR¹¹, —CHF₂, —OCHF₂, —OSO₂R¹¹, —CONR¹¹R¹², —OCH₂CONR¹¹R¹², —CH₂OR¹¹, —CH₂NR¹¹R¹², —OCOR¹¹, —CO₂R¹³ or —OSO₂CF₃;

R⁸ and R⁹ independently are hydrogen, halogen, —CN, —CF₃, —OCF₃, —OCH₂CF₃, —NO₂, —OR¹¹, —NR¹¹R¹², lower alkyl, aryl, —SCF₃, —SR¹¹, —CHF₂, —OCHF₂, —OSO₂R¹¹, —CONR¹¹R¹², —CH₂OR¹¹, —CH₂NR¹¹R¹², —OCOR¹¹, —CO₂R¹³ or —OSO₂CF₃, or R⁸ and R⁹ together form —OCH₂O— or —OCH₂CH₂O—;

R¹¹ and R¹² independently are hydrogen, —COR¹³, —SO₂R¹³, lower alkyl or aryl;

R¹³ is hydrogen, lower alkyl, aryl-lower alkyl or aryl; and

R¹⁰ is hydrogen, lower alkyl, aryl-lower alkyl or aryl);

B is a group represented by the following formula:

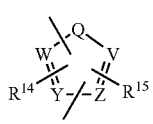

(wherein R¹⁴ and R¹⁵ independently are hydrogen, halogen, —CN, —CF₃, —OCF₃, —O(CH₂)₁CF₃, —NO₂, —OR¹⁶, —NR¹⁶R¹⁷, lower alkyl, aryl, aryl-lower alkyl, —SCF₃, —SR¹⁶, —CHF₂, —OCHF₂, —OCF₂CHF₂, —OSO₂CF₃, —CONR¹⁶R¹⁷, —(CH₂)₁CONR¹⁶R¹⁷, —O(CH₂)₁CONR¹⁶R¹⁷, —(CH₂)₁COR¹⁶, —(CH₂)₁OR¹⁶, —O(CH₂)₁OR¹⁶, —(CH₂)₁NR¹⁶R¹⁷, —O(CH₂)₁NR¹⁶R¹⁷, —OCOR¹⁶, —CO₂R¹⁸, —O(CH₂)₁CO₂R¹⁸, —O(CH₂)₁CN or —O(CH₂)₁Cl, or R¹⁴ and R¹⁵ together form —O(CH₂)₁O— or —(CH₂)₁—;

1, 2, 3 or 4;

R¹⁶ and R¹⁷ independently are hydrogen, —COR¹⁸, —SO₂R¹⁸, lower alkyl or aryl, or R¹⁶ and R¹⁷ together form a C₂₋₇ cyclic alkyl bridge;

R¹⁸ is hydrogen, lower alkyl, aryl or aryl-lower alkyl;

W is —N= or —CR¹⁹=;

Y is —N= or —CR²⁰=;

Z is —N= or —CR²¹=;

V is —N= or —CR²²=; and

Q is —N²³, —O— or —S—);

K is a group represented by the following formula:

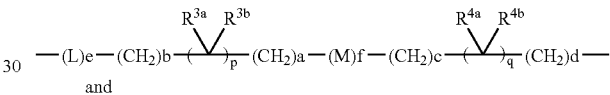

and

D is hydrogen or a group represented by the following formula:

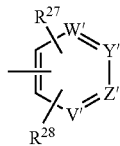

(wherein Y' is —N= or —CR³²=;

Z' is —N= or —CR³³=;

V' is —N= or —CR³⁴=;

W' is —N= or —CR³⁵=;

R²⁷, R²⁸, R³², R³³, R³⁴ and R³⁵ independently are hydrogen, halogen, —CN, —CF₃, —O(CH₂)ᵧCF₃, —(CH₂)ᵧNH-COCF₃, —NO₂, lower alkyl, aryl, aryl-lower alkyl, —SCF₃, —SR²⁹, —CHF₂, —OCHF₂, —OCF₂CHF₂, —OSO₂R²⁹, —OSO₂CF₃, —(CH₂)ᵧCONR²⁹R³⁰, —O(CH₂)ᵧCONR²⁹R³⁰, —(CH₂)ᵧOR²⁹, —(CH₂)ᵧNR²⁹R³⁰, —OCOR²⁹, —COR²⁹ or —CO₂R²⁹, or R²⁷ and R²⁸, R³² and R³³, R³³ and R³⁴, or R³⁴ and R³⁵ together form —O(CH₂)ᵧO—; and y is 0, 1, 2, 3 or 4).

Although the claims of the aforementioned PCT application include a great number of compounds, it discloses the compound represented by Formula (2) below as the only specific example of a compound represented by the aforementioned Formula (1) wherein B is a furan ring.

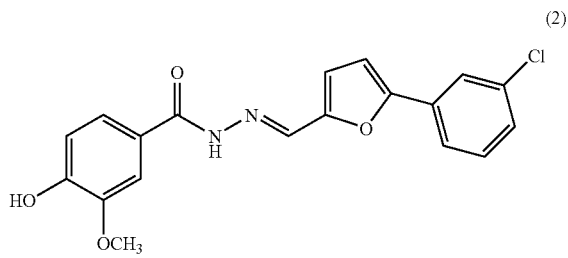

(2)

WO 00/39088 discloses compounds having chemical structures similar to those of the compounds disclosed in WO99/01423 and also teaches that they can be used as a glucagon antagonist or an inverse agonist.

Japanese Unexamined Patent Publication No. 91061/1973 (*Chem. Abstr.* 1974, 80, 120745v) discloses that a diphenyl furan derivative represented by Formula (3) below has antibacterial and antiprotozoal actions, and is useful as a pharmaceutical or animal drug:

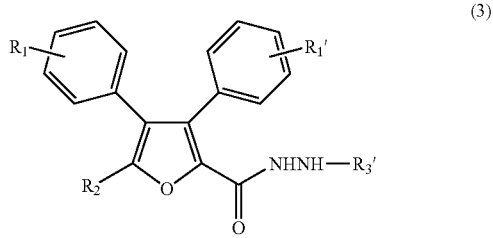

(3)

wherein $R_1$ and $R_1'$ are the same or different, and independently represent a hydrogen atom, a lower alkyl or lower alkoxy group; $R_2$ is a hydrogen atom or a nitro group; and $R_3'$ is an acyl group or an arylsulfonyl group.

However, the aforedmentioned patent publication discloses only the following 9 compounds shown in Table 1 as 2-furancarboxylic acid 2-acylhydrazide compounds:

TABLE 1

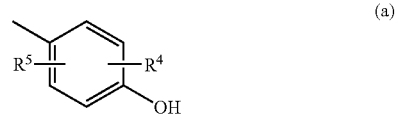

| $R_2$ | $R_3'$ |
|---|---|
| H | 2-furoyl |
| H | 5-methyl-2-furoyl |
| $NO_2$ | Acetyl |
| $NO_2$ | 5-methyl-2-furoyl |
| $NO_2$ | 5-bromo-2-furoyl |
| $NO_2$ | isonicotinoyl |
| $NO_2$ | 4-chlorobenzoyl |
| $NO_2$ | 3,4-diphenyl-2-furoyl |
| $NO_2$ | 5-nitro-3,4-diphenyl-2-furoyl |

DISCLOSURE OF THE INVENTION

The present inventors have intensively studied on 2-furancarboxylic acid derivatives and have found that the novel 2-furancarboxylic acid hydrazide compounds represented by General Formula (I) below exhibit a potent antagonistic activity on glucagon receptor, and are useful as preventive and/or therapeutic agents for symptoms and diseases in which glucagon is involved, and finally have accomplished the present invention.

An object of the present invention is to provide a novel 2-furancarboxylic acid hydrazide compound having a potent antagonistic activity on glucagon receptor. In particular, an object of the present invention is to provide a novel 2-furancarboxylic acid hydrazide compound useful as a therapeutic agent for diabetes mellitus. Another object of the present invention is to provide a pharmaceutical composition containing such a compound. These objects, other objects and advantages of the present invention are obvious to any person skilled in the art from the following disclosure.

The present invention provides 2-furancarboxylic acid hydrazide compounds represented by Formula (I) below, their prodrugs, their physiologically acceptable salts, their hydrates, their solvates, methods for producing them and pharmaceutical compositions containing them:

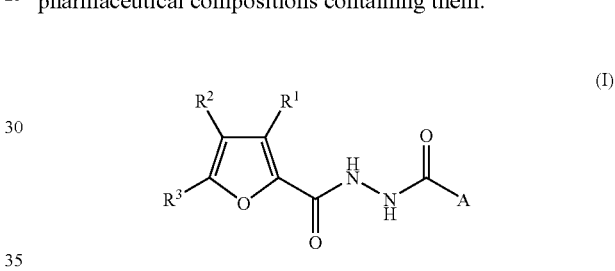

(I)

wherein A is a substituted or unsubstituted heteroaryl group other than 2-furyl group, or a group represented by Formula (a) below:

(a)

wherein either $R^4$ or $R^5$ represents a hydrogen atom, a halogen atom, a trifluoromethyl group, a hydroxy group, a $C_{1-6}$ alkyl group, a $C_{2-6}$ alkenyl group, a $C_{2-6}$ alkynyl group, a $C_{1-6}$ alkoxy group, a trifluoromethoxy group, a trifluoroethoxy group, a $C_{1-2}$ alkylsulfonyl group, a cyano group, a nitro group, an amino group, a mono- or di-substituted amino group, a $C_{1-6}$ alkoxycarbonylamino group, a carbamoyl group, a mono- or di-substituted carbamoyl group, a sulfamoyl group, a mono- or di-substituted sulfamoyl group, a $C_{1-6}$ alkylsulfonylamino group, an aryl group, a heteroaryl group, a $C_{1-6}$ alkoxycarbonyl group, an arylmethyloxycarbonyl group, a carboxyl group, a 5-tetrazolyl group, a sulfo group (—$SO_2OH$) or a fluorosulfonyl group, and the other represents a hydrogen atom or a halogen atom, either $R^1$ or $R^2$ represents a group: -D-(X)m-$R^6$, an aryl group or a heteroaryl group, and the other represents a group: -E-(Y)n-$R^7$, a hydrogen atom, a halogen atom, a $C_{1-10}$ alkyl group, a $C_{3-7}$ cycloalkyl group, a $C_{2-10}$ alkenyl group, a $C_{2-10}$ alkynyl group, an aryl group or a heteroaryl group, with the alkyl group, the alkenyl group and the alkynyl group being optionally substituted by 1 to 3 atoms or groups selected from the group consisting of halogen, hydroxy (this hydroxy itself being optionally acylated, carbamated or etherified), disubstituted amino, aryl and heteroaryl, $R^3$ is a hydrogen atom, a halogen atom, a hydroxy atom, a $C_{1-6}$ alkyl group, a $C_{1-6}$ alkoxy group, an aryl group, a heteroaryl group or an aryl-substituted $C_{1-4}$ alkyl group, D and E are the same or different, and independently represent an arylene group, X and Y are the same or different, and independently represent —O—, —S—, —SO—, —SO$_2$—, —OSO$_2$—, —NR$^8$—, —CO—, —CH=CH—, —C≡C—, —CONH—, —NHCO—, —NHCOO—, —OCH$_2$CONH— or —OCH$_2$CO—, $R^6$ and $R^7$ are the same or different, and independently represent a $C_{1-10}$ alkyl group, a $C_{2-10}$ alkenyl group, a $C_{2-10}$ alkynyl group, a $C_{3-7}$ cycloalkyl group, a $C_{3-7}$ cycloalkyl-substituted $C_{1-4}$ alkyl group, an aryl group, a heteroaryl group, an aryl-substituted $C_{1-4}$ alkyl group or a heteroaryl-substituted $C_{1-4}$ alkyl, with the alkyl moiety of the aryl-substituted $C_{1-4}$ alkyl group or the heteroaryl-substituted $C_{1-4}$ alkyl group being optionally substituted by hydroxy, $R^8$ is a hydrogen atom or a $C_{1-10}$ alkylcarbonyl group, and m and n are independently 0 or 1, provided that the aryl group, the aryl moiety, the heteroaryl group, the heteroaryl moiety and the arylene group are optionally substituted by 1 to 4 atoms or groups selected from the group consisting of halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl).

Prodrugs of the compounds represented by General Formula (I) refer to compounds that are represented by General Formula (I) wherein A is a group represented by Formula (a) in which the hydroxy group at the 4-position of the benzoyl moiety is modified but can be converted to a hydroxy group by enzymatic or chemical cleavage in vivo. Examples include those in which the hydroxy group at the 4-position of the benzoyl moiety is etherified or esterified.

In particular, examples include compounds in which the aforementioned hydroxy group is substituted by a $C_{1-6}$ alkoxy group, an unsubsititued or substituted arylmethyloxy group, a hydroxy $C_{1-6}$ alkoxy group, a formyloxy group, a $C_{1-6}$ alkylcarbonyloxy group (the alkyl moiety thereof optionally being substituted by amino, mono- or di-substituted amino, or carboxyl), an unsubsititued or substituted aroyloxy group, a $C_{1-6}$ alkoxycarbonyloxy group, or an oxy group having an acid residue derived from an inorganic acid. Typical examples include those substituted by a methoxy group, a benzyloxy group, an acetoxy group, a pivaloyloxy group, a dimethylaminoacetoxy group, an alanyloxy group, a 2-amino-2-methylpropanoyloxy group, a 3-carboxypropanoyl group, a benzoyloxy group, a 4-methoxybenzoyloxy group, a 4-dimethylaminobenzoyloxy group, a 4-diethylaminobenzoyloxy group, a 3,4,5-trihydroxybenzoyloxy group, a phosphoxy group or the like. Preferable are ester-type compounds.

Physiologically acceptable salts of the compounds represented by General Formula (I) or prodrugs thereof are those having a group that can form an acid addition salt in their structure (e.g., a substituted or unsubstituted amino, substituted or unsubstituted nitrogen-containing heteroaryl, nitrogen-containing heterocyclic group), and those that can form a salt with a base in their structure (e.g., COOH, SO$_3$H, phenolic OH, etc.). Specific examples of acid addition salts include a salt with an inorganic acid such as hydrochloride, hydrobromide, hydroiodide, sulfate, perchlorate and phosphate, a salt with organic acid such as oxalate, malonate, succinate, maleate, fumarate, lactate, malate, citrate, tartrate, benzoate, trifluoroacetate, acetate, methanesulfonate, p-toluenesulfonate and trifluoromethanesulfonate, or a salt with an acidic amino acid such as glutamate and aspartate. Specific examples of a salt with a base include an alkali metal or an alkaline-earth metal salt such as sodium salt, potassium salt and calcium salt, a salt with an organic base such as pyridine salt and triethylamine salt, a salt with a basic amino acid such as lysine and arginine.

The compounds of General Formula (I), and prodrugs and salts thereof, may be in the form of hydrates or solvates, and the present invention also includes such hydrates and solvates. Furthermore, the compounds of General Formula (I) and prodrugs thereof may include one or more asymmetrical carbon atoms or may have geometrical isomers. Therefore, the compounds of General Formula (I) and prodrugs thereof may sometimes be present as some stereoisomers. The present invention includes such stereoisomers, and mixtures and racemates thereof.

Solvents usable to form solvates are alcohols such as ethanol and propanol, organic acids such as acetic acid, ethers such as ethyl acetate, tetrahydrofuran and diethyl ether, DMSO, etc.

The terms used herein are defined as below:

In this specification, when the number of carbon atoms is specified, such as "$C_{1-6}$" alkylcarbonyloxy, this carbon number refers to the carbon number of the group or moiety that comes immediately after the number. Therefore, in the case above, "$C_{1-6}$" refers only to the carbon number of the alkyl. Hence, "$C_1$ alkylcarbonyloxy" is acetoxy.

The alkyl group or alkyl moiety may be linear or branched.

In the present specification, the alkyl moiety includes not only each alkyl group in a $C_{1-2}$ alkylsulfonyl group, a $C_{1-6}$ alkylsulfonylamino group, an aryl-substituted $C_{1-4}$ alkyl group, a heteroaryl-substituted $C_{1-4}$ alkyl group and a $C_{1-10}$ alkylcarbonyl group, but also the alkyl group of substituent(s) of the alkyl group of the alkoxy (O-alkyl) in a $C_{1-6}$ alkoxycarbonylamino group, a $C_{1-6}$ alkoxycarbonyl group and a $C_{1-6}$ alkoxy group, a mono- or di-substituted amino, a mono- or di-substituted sulfamoyl group and a disubstituted amino group.

The term "aryl moiety" refers to the aryl group in an arylmethyloxycarbonyl group and an aryl-substituted $C_{1-4}$ alkyl group.

The term "heteroaryl moiety" refers to the heteroaryl group in a heteroaryl-substituted $C_{1-4}$ alkyl group.

The term "halogen atom" refers to fluorine, chlorine, bromine or iodine. Preferable are fluorine, chlorine and bromine.

The "$C_{1-10}$ alkyl group" may be linear, branched or cyclic. Examples are methyl, ethyl, n-propyl, isopropyl, n-butyl, isobutyl, tert-butyl, n-pentyl, isopentyl, hexyl, heptyl, octyl, nonyl and decyl.

The "$C_{1-6}$ alkyl group" may be linear or branched. Examples are methyl, ethyl, n-propyl, isopropyl, n-butyl, isobutyl, tert-butyl, n-pentyl, isopentyl and hexyl.

The "$C_{1-4}$ alkyl group" may be linear or branched. Examples are methyl, ethyl, n-propyl, isopropyl, n-butyl, isobutyl and tert-butyl.

The "$C_{1-3}$ alkyl group" may be linear or branched. Examples are methyl, ethyl, n-propyl and isopropyl.

The "$C_{1-2}$ alkyl group" refers to methyl or ethyl.

Specific examples of the "$C_{3-7}$ cycloalkyl group" are cyclopropyl, cyclobutyl, cyclopentyl, cyclohexyl and cycloheptyl.

Specific examples of the "$C_{3-7}$ cycloalkyl-substituted $C_{1-4}$ alkyl group" are cyclopropylmethyl, cyclobutylmethyl, cyclopentylmethyl, cyclohexylmethyl and cycloheptylmethyl.

The "$C_{2-10}$ alkenyl group" may be linear, branched or cyclic, and has at least one double bond. Examples include vinyl, allyl, 1-propenyl, 2-methyl-2-propenyl, isopropenyl, 1-, 2- or 3-butenyl, 2-, 3- or 4-pentenyl, 2-methyl-2-butenyl, 3-methyl-2-butenyl, 5-hexenyl, 1-cyclopentenyl, 1-cyclohexenyl, 3-methyl-3-butenyl, and equivalents thereof.

The "$C_{2-6}$ alkenyl group" may be linear, branched or cyclic, and has at least one double bond. Examples include vinyl, allyl, 1-propenyl, 2-methyl-2-propenyl, isopropenyl, 1-, 2- or 3-butenyl, 2-, 3- or 4-pentenyl, 2-methyl-2-butenyl, 3-methyl-2-butenyl, 5-hexenyl, 1-cyclopentenyl, 1-cyclohexenyl, 3-methyl-3-butenyl, and equivalents thereof.

The "$C_{2-10}$ alkynyl group" may be linear, branched or cyclic, and has at least one triple bond. Examples include ethynyl, 1- or 2-propynyl, 1-, 2- or 3-butynyl, 1-methyl-2-propynyl, and equivalents thereof.

The "$C_{2-6}$ alkynyl group" may be linear, branched or cyclic, and has at least one triple bond. Examples include ethynyl, 1- or 2-propynyl, 1-, 2- or 3-butynyl, 1-methyl-2-propynyl, and equivalents thereof.

The term "monosubstituted" as in "mono- or di-substituted amino group", "mono- or di-substituted carbamoyl group", and "mono- or di-substituted sulfamoyl group" means that one of the hydrogen atoms bound to the nitrogen atom of the amino group, the carbamoyl group or the sulfamoyl group is substituted by $C_{1-6}$ alkyl. The term "di-substituted" means that two of the hydrogen atoms bound to the nitrogen atom of the amino group, the carbamoyl group or the sulfamoyl group are substituted by the same or different $C_{1-6}$ alkyl or a three- to eight-membered, and preferably five- or six-membered, nitrogen-containing cyclic group. Examples of nitrogen-containing cyclic groups include morpholino, 1-pyrrolidinyl, piperidino and 4-methyl-1-piperazinyl.

Examples of the amino groups mono-substituted by $C_{1-6}$ alkyl include methylamino, ethylamino, n-propylamino, isopropylamino, n-butylamino, isobutylamino, tert-butylamino, n-pentylamino, isopentylamino and hexylamino.

Examples of the amino groups di-substituted by $C_{1-6}$ alkyl include dimethylamino, diethylamino, di-n-propylamino, diisopropylamino, di-n-butylamino, diisobutylamino, di-tert-butylamino, di-n-pentylamino, diisopentylamino and dihexylamino.

Examples of the carbamoyl groups mono-substituted by $C_{1-6}$ alkyl include methylcarbamoyl, ethylcarbamoyl, n-propylcarbamoyl, isopropylcarbamoyl, n-butylcarbamoyl, isobutylcarbamoyl, tert-butylcarbamoyl, n-pentylcarbamoyl, isopentylcarbamoyl and hexylcarbamoyl.

Examples of the carbamoyl groups di-substituted by $C_{1-6}$ alkyl include dimethylcarbamoyl, diethylcarbamoyl, di-n-propylcarbamoyl, diisopropylcarbamoyl, di-n-butylcarbamoyl, diisobutylcarbamoyl, di-tert-butylcarbamoyl, di-n-pentylcarbamoyl, diisopentylcarbamoyl and dihexylcarbamoyl.

Examples the sulfamoyl groups mono-substituted by $C_{1-6}$ alkyl include methylsulfamoyl, ethylsulfamoyl, n-propylsulfamoyl, isopropylsulfamoyl, n-butylsulfamoyl, isobutylsulfamoyl, tert-butylsulfamoyl, n-pentylsulfamoyl, isopentylsulfamoyl and hexylsulfamoyl.

Examples of the sulfamoyl groups di-substituted by $C_{1-6}$ alkyl include dimethylsulfamoyl, diethylsulfamoyl, di-n-propylsulfamoyl, diisopropylsulfamoyl, di-n-butylsulfamoyl, diisobutylsulfamoyl, di-tert-butylsulfamoyl, di-n-pentylsulfamoyl, diisopentylsulfamoyl and dihexylsulfamoyl.

The term "aryl group" refers to a mono- or poly-cyclic group having five- or six-membered aromatic hydrocarbon ring(s). Specific examples include phenyl, naphthyl, fluorenyl, anthryl, biphenylyl, tetrahydronaphthyl, chromanyl, 2,3-dihydro-1,4-dioxanaphthalenyl, indanyl and phenanthryl.

The term "arylene group" refers to a mono- or poly-cyclic divalent group having five- or six-membered aromatic hydrocarbon ring(s). Specific examples include phenylene and naphthylene.

The term "heteroaryl group" refers to a mono- or polycyclic group that contains 1 to 3 hetero atoms selected from N, O and S and has five- or six-member aromatic hydrocarbon ring(s). When polycyclic, at least one ring is aromatic. Specific examples include furyl, thienyl, pyrrolyl, imidazolyl, pyrazolyl, oxazolyl, thiazolyl, isooxazolyl, isothiazolyl, pyridyl, pyrazinyl, pyrimidinyl, pyridazinyl, indolyl, quinolyl, isoquinolyl, benzo[b]thienyl and benzimidazolyl.

The term "acylated hydroxy" refers to $C_{1-6}$ alkylcarbonyloxy, arylcarbonyloxy or aryl-substituted $C_{1-4}$ alkylcarbonyloxy.

The term "carbamated hydroxy" refers to $C_{1-6}$ alkylaminocarbonyloxy, arylaminocarbonyloxy or aryl-substituted $C_{1-4}$ alkylaminocarbonyloxy.

The term "etherified hydroxy" refers to $C_{1-6}$ alkyloxy or aryl-substituted $C_{1-4}$ alkyloxy.

Specific examples of the $C_{1-6}$ alkylcarbonyloxy are methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy and hexylcarbonyloxy.

Specific examples of the arylcarbonyloxy are phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy and phenanthrylcarbonyloxy.

Specific examples of the aryl-substituted $C_{1-4}$ alkylcarbonyloxy are benzylcarbonyloxy, naphthylmethylcarbonyloxy, fluorenylmethylcarbonyloxy, anthrylmethylcarbonyloxy, biphenylylmethylcarbonyloxy, tetrahydronaphthylmethylcarbonyloxy, chromanylmethylcarbonyloxy, 2,3-dihydro-1,4-dioxanaphthalenylmethylcarbonyloxy, indanylmethylcarbonyloxy, phenanthrylmethylcarbonyloxy, phenethylcarbonyloxy, naphthylethylcarbonyloxy, fluorenylethylcarbonyloxy, anthrylethylcarbonyloxy, biphenylylethylcarbonyloxy, tetrahydronaphthylethylcarbonyloxy, chromanylethylcarbonyloxy, 2,3-dihydro-1,4-dioxanaphthalenylethylcarbonyloxy, indanylethylcarbonyloxy and phenanthrylethylcarbonyloxy.

Specific examples of the $C_{1-6}$ alkylaminocarbonyloxy are methylaminocarbonyloxy, ethylaminocarbonyloxy, n-propylaminocarbonyloxy, isopropylaminocarbonyloxy, n-butylaminocarbonyloxy, isobutylaminocarbonyloxy, tert-butylaminocarbonyloxy, n-pentylaminocarbonyloxy, isopentylaminocarbonyloxy and hexylaminocarbonyloxy.

Specific examples of the arylaminocarbonyloxy are phenylaminocarbonyloxy, naphthylaminocarbonyloxy, fluorenylaminocarbonyloxy, anthrylaminocarbonyloxy, biphenylylaminocarbonyloxy, tetrahydronaphthylaminocarbonyloxy, chromanylaminocarbonyloxy, 2,3-dihydro-1,4-dioxanaphthalenylaminocarbonyloxy, indanylaminocarbonyloxy and phenanthrylaminocarbonyloxy.

Specific examples of the aryl-substituted $C_{1-4}$ alkylaminocarbonyloxy are benzylaminocarbonyloxy, naphthylmethylaminocarbonyloxy, fluorenylmethylaminocarbonyloxy, anthrylmethylaminocarbonyloxy, biphenylylmethylaminocarbonyloxy, tetrahydronaphthylmethylaminocarbonyloxy, chromanylmethylaminocarbonyloxy, 2,3-dihydro-1,4-dioxanaphthalenylmethylaminocarbonyloxy, indanylmethylaminocarbonyloxy, phenanthrylmethylaminocarbonyloxy, phenethylaminocarbonyloxy, naphthylethylaminocarbonyloxy, fluorenylethylaminocarbonyloxy, anthrylethylaminocarbonyloxy, biphenylylethylaminocarbonyloxy, tetrahydronaphthylethylaminocarbonyloxy, chromanylethylaminocarbonyloxy, 2,3-dihydro-1,4-dioxanaphthalenylethylaminocarbonyloxy, indanylethylaminocarbonyloxy and phenanthrylethylaminocarbonyloxy.

Specific examples of the $C_{1-6}$ alkyloxy are methyloxy, ethyloxy, n-propyloxy, isopropyloxy, n-butyloxy, isobutyloxy, tert-butyloxy, n-pentyloxy, isopentyloxy and hexyloxy.

Specific examples of the aryloxy are phenyloxy, naphthyloxy, fluorenyloxy, anthryloxy, biphenylyloxy, tetrahydronaphthyloxy, chromanyloxy, 2,3-dihydro-1,4-dioxanaphthalenyloxy, indanyloxy and phenanthryloxy.

Specific examples of the aryl-substituted $C_{1-4}$ alkyloxy are benzyloxy, naphthylmethyloxy, fluorenylmethyloxy, anthrylmethyloxy, biphenylylmethyloxy, tetrahydronaphthylmethyloxy, chromanylmethyloxy, 2,3-dihydro-1,4-dioxanaphthalenylmethyloxy, indanylmethyloxy, phenanthrylmethyloxy, phenethyloxy, naphthylethyloxy, fluorenylethyloxy, anthrylethyloxy, biphenylylethyloxy, tetrahydronaphthylethyloxy, chromanylethyloxy, 2,3-dihydro -1,4-dioxanaphthalenylethyloxy, indanylethyloxy and phenanthrylethyloxy.

Specific examples of the combined groups containing a carbon-number-specified alkyl, cycloalkyl, alkenyl or alkynyl moiety, or aryl or heteroaryl moiety are those that have the aforementioned specific examples of each group at the corresponding moieties.

For example, specific examples of the $C_{1-6}$ alkoxy group are methoxy, ethoxy, propoxy, isopropoxy, butoxy, isobutoxy, tert-butoxy, pentyloxy, isopentyloxy and hexyloxy.

$CF_3CH_2O$— is preferable as the trifluoroethoxy group.

Specific examples of the $C_{1-2}$ alkylsulfonyl group are methylsulfonyl and ethylsulfonyl.

Specific examples of the $C_{1-6}$ alkoxycarbonylamino group are methoxycarbonylamino, ethoxycarbonylamino, propoxycarbonylamino, isopropoxycarbonylamino, butoxycarbonylamino, isobutoxycarbonylamino, tert-butoxycarbonylamino, pentyloxycarbonylamino, isopentyloxycarbonylamino and hexyloxycarbonylamino.

Specific examples of the $C_{1-6}$ alkylsulfonylamino group are methylsulfonylamino, ethylsulfonylamino, n-propylsulfonylamino, isopropylsulfonylamino, n-butylsulfonylamino, isobutylsulfonylamino, tert-butylsulfonylamino, n-pentylsulfonylamino, isopentylsulfonylamino and hexylsulfonylamino.

Specific examples of the $C_{1-6}$ alkoxycarbonyl group are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl and hexyloxycarbonyl.

Specific examples of the arylmethyloxycarbonyl group are phenylmethyloxycarbonyl, naphthylmethyloxycarbonyl, fluorenylmethyloxycarbonyl, anthrylmethyloxycarbonyl, biphenylylmethyloxycarbonyl, tetrahydronaphthylmethyloxycarbonyl, chromanylmethyloxycarbonyl, 2,3-dihydro-1,4-dioxanaphthalenylmethyloxycarbonyl, indanylmethyloxycarbonyl and phenanthrylmethyloxycarbonyl.

Specific examples of the aryl-substituted $C_{1-4}$ alkyl group are benzyl, naphthylmethyl, fluorenylmethyl, anthrylmethyl, biphenylylmethyl, tetrahydronaphthylmethyl, chromanylmethyl, 2,3-dihydro-1,4-dioxanaphthalenylmethyl, indanylmethyl, phenanthrylmethyl, phenethyl, naphthylethyl, fluorenylethyl, anthrylethyl, biphenylylethyl, tetrahydronaphthylethyl, chromanylethyl, 2,3-dihydro-1,4-dioxanaphthalenylethyl, indanylethyl and phenanthrylethyl.

Specific examples of the heteroaryl-substituted $C_{1-4}$ alkyl group are furylmethyl, thienylmethyl, pyrrolylmethyl, imidazolylmethyl, pyrazolylmethyl, oxazolylmethyl, thiazolylmethyl, isooxazolylmethyl, isothiazolylmethyl, pyridylmethyl, pyrazinylmethyl, pyrimidinylmethyl, pyridazinylmethyl, indolylmethyl, quinolylmethyl, isoquinolylmethyl, benzo[b]thienylmethyl, benzimidazolylmethyl, furylethyl, thienylethyl, pyrrolylethyl, imidazolylethyl, pyrazolylethyl, oxazolylethyl, thiazolylethyl, isooxazolylethyl, isothiazolylethyl, pyridylethyl, pyrazinylethyl, pyrimidinylethyl, pyridazinylethyl, indolylethyl, quinolylethyl, isoquinolylethyl, benzo[b]thienylethyl and benzimidazolylethyl.

Groups represented by Formula (a) are preferable as "A" in General Formula (I) above, with groups represented by Formula (b0) below being more preferable:

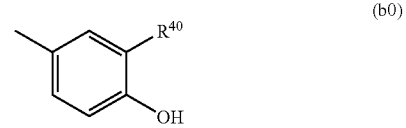

(b0)

wherein $R^{40}$ is a halogen atom, a trifluoromethyl group, a $C_{2-6}$ alkynyl group, a trifluoromethoxy group, a trifluoroethoxy group, a $C_{1-2}$ alkylsulfonyl group, a cyano group, a nitro group, a $C_{1-4}$ alkoxycarbonylamino group, a carbamoyl group, a mono- or di-substituted carbamoyl group, a sulfamoyl group, a mono- or di-substituted sulfamoyl group, a $C_{1-4}$ alkylsulfonylamino group, a $C_{1-4}$ alkoxycarbonyl group, an arylmethyloxycarbonyl group, a carboxyl group, a 5-tetrazolyl group, a sulfo group (—$SO_2OH$) or a fluorosulfonyl group.

As $R^{40}$, preferable are a halogen atom, a trifluoromethyl group, an ethynyl group, a methylsulfonyl group, a cyano group, a nitro group, a tert-butoxycarbonyl group and a carbamoyl group. A cyano group and a nitro group are particularly preferable.

In the groups represented by -D-(X)m-$R^6$ and -E-(Y)n-$R^7$ in $R^1$ and $R^2$, "D" and "E" are preferably phenylene groups. Such phenylene groups may be 1,2-, 1,3- or 1,4-phenylene group, with 1,3- and 1,4-phenylene groups being particularly preferable.

Preferable for "X" and "Y" are O, S, —CH=CH—, —$OCH_2CONH$— and —$OCH_2CO$—. For "m" and "n", 1 is preferable.

When "X" or "Y" is O or S, specific examples of groups represented by $R^6$ or $R^7$ are isopropyl, propyl, butyl, isobutyl, pentyl, hexyl, heptyl, nonyl, decyl, cyclohexyl, 2-methyl-2-butenyl, benzyl, phenethyl, 1-phenylethyl, 1-methyl-2-phenylethyl, 2-phenylpropyl, 4-phenylbutyl, 5-phenylpentyl, 2-, 3- or 4-fluorobenzyl, 2-, 3- or 4-methylbenzyl, 4-isopropylbenzyl, 4-tert-butylbenzyl, 2,4-, 2,5-, 3,4-, 3,5- or 2,6-dimethylbenzyl, 2,4,6-trimethylbenzyl, 2,3,5,6-tetramethylbenzyl, 2-, 3- or 4-methoxybenzyl, 2,3- or 2,5-dimethoxybenzyl, 2-chloro-4,5-methylenedioxybenzyl, 3,4,5-trimethoxybenzyl, 2-, 3- or 4-trifluoromethoxybenzyl, 2-, 3-, or 4-trifluoromethylbenzyl, 1-(3-trifluoromethylphenyl)ethyl, 4-methylsulfonylbenzyl, 2-, 3- or 4-dimethylaminobenzyl, 2-, 3-, or 4-nitrobenzyl, 4-chloro-2-dimethylaminobenzyl, 4-chloro- 2-nitrobenzyl, 4-chloro-3-dimethylaminobenzyl, 4-chloro-3-nitrobenzyl, 2-chloro-5-dimethylaminobenzyl, 2-chloro-5-nitrobenzyl, 3-dimethylamino-2-methylbenzyl, 2-methyl-3-nitrobenzyl, 3-dimethylamino-4-methylbenzyl, 4-methyl-3-nitrobenzyl, 2-dimethylamino-5-methylbenzyl, 5-methyl-2-nitrobenzyl, 2-dimethylamino-6-fluorobenzyl, 6-fluoro-2-nitrobenzyl, 5-dimethylamino-2-methoxybenzyl, 2-methoxy-5-nitrobenzyl, 2-dimethylamino-4,5-dimethoxybenzyl, 4,5-dimethoxy-2-nitrobenzyl, 2-dimethylamino-4-trifluoromethylbenzyl, 2-nitro-4-trifluoromethylbenzyl, 4-dimethylamino-3-phenylbenzyl, 4-nitro-3-phenylbenzyl, 2,3-dichloro-5-hydroxymethylbenzyl, 3-hydroxymethylbenzyl, 1- or 2-naphthylmethyl, 2-, 3- or 4-pyridylmethyl, 2-chloro-5-pyridylmethyl, 4,5-dichloro-3-pyridylmethyl, 2,6-dichloro-4-pyridylmethyl, 4-methyl-2-pyridylmethyl, 6-methyl-2-pyridylmethyl, 3,4-dimethoxy-2-pyridylmethyl, 2-phenyl-5-pyridylmethyl, 2-methyl-2-propenyl, and equivalents thereof.

When "X" or "Y" is —CH═CH—, specific examples of groups represented by $R^6$ or $R^7$ are 2-, 3- or 4-methoxyphenyl, 2-, 3-, or 4-nitrophenyl, 2-, 3- or 4-aminophenyl, 2-, 3- or 4-dimethylaminophenyl, 2,3-, 2,5- or 3,5-dimethoxyphenyl, 3,4,5-trimethoxyphenyl, 2-, 3- or 4-pyridyl, 4-methoxybenzyl, 3,5-dimethoxybenzyl, 2-pyridylmethyl, 2-, 3- or 4-methylbenzyl, and equivalents thereof.

When "X" or "Y" is —OCH$_2$CONH—, specific examples of groups represented by $R^6$ or $R^7$ are phenyl, 2-, 3- or 4-fluorophenyl, 2-, 3- or 4-chlorophenyl, 2-, 3- or 4-bromophenyl, 2,4-difluorophenyl, 2,3-, 2,4-, 3,4-, 3,5- or 2,6-dichlorophenyl, 3-chloro-4-fluorophenyl, 4-isopropylphenyl, 2,6-dimethylphenyl, 2-, 3- or 4-trifluoromethylphenyl, 4-methoxyphenyl, 4-trifluoromethoxyphenyl, 2-, 3- or 4-dimethylaminophenyl, 2-, 3- or 4-nitrophenyl, 4-sulfamoylphenyl, 2-chloro-3-pyridyl, 4-iodo-2-pyridyl, 4-methyl-2-pyridyl, 3-chloro-5-trifluoromethyl-2-pyridyl, 2-methoxy-3-trifluoromethyl-5-pyridyl, 2-, 3- or 4-methylbenzyl, and equivalents thereof.

When "X" or "Y" is —OCH$_2$CO—, specific example of groups represented by $R^6$ or $R^7$ are phenyl, 2-, 3- or 4-fluorophenyl, 2- or 4-chlorophenyl, 3- or 4-bromophenyl, 2,4- or 3,4-difluorophenyl, 2,4-dichlorophenyl, 4-methylphenyl, 4-trifluoromethylphenyl, 4-chloro-3-methylphenyl, 3-chloro-4-ethylphenyl, 2-, 3- or 4-methoxyphenyl, 2,4- or 2,5-dimethoxyphenyl, 4-trifluoromethoxyphenyl, 2-, 3- or 4-dimethylaminophenyl, 2-, 3- or 4-nitrophenyl, 4-chloro-3-dimethylaminophenyl, 4-(1-pyrrolidinyl)phenyl, 4-methylsulfonylaminophenyl, 4-diethylsulfamoylphenyl, 2-, 3- or 4-pyridyl, 2-, 3- or 4-methylbenzyl, and equivalents thereof.

The definition of $R^1$ and $R^2$ in General Formula (I) above can also be stated as:

$R^1$ is a group: -D-(X)m-$R^6$; an aryl group; a heteroaryl group; a hydrogen atom; a halogen atom; or a $C_{1-10}$ alkyl group, a $C_{3-7}$ cycloalkyl group, a $C_{2-10}$ alkenyl group or a $C_{2-10}$ alkynyl group optionally substituted by 1 to 3 atoms or groups selected from halogen, hydroxy (which itself may be acylated, carbamated or etherified), disubstituted amino, aryl and heteroaryl.

When $R^1$ is a group: -D-(X)m-$R^6$; an aryl group or a heteroaryl group, then $R^2$ is a group: -E-(Y)n-$R^7$; an aryl group, a heteroaryl group; a hydrogen atom; a halogen atom; or a $C_{1-10}$ alkyl group, a $C_{3-7}$ cycloalkyl group, a $C_{2-10}$ alkenyl group or a $C_{2-10}$ alkynyl group optionally substituted by 1 to 3 atoms or groups selected from halogen, hydroxy (which itself may be acylated, carbamated or etherified), disubstituted amino, aryl and heteroaryl.

When $R^1$ is a hydrogen atom; a halogen atom; or a $C_{1-10}$ alkyl group, a $C_{3-7}$ cycloalkyl group, a $C_{2-10}$ alkenyl group or a $C_{2-10}$ alkynyl group optionally substituted by 1 to 3 atoms or groups selected from halogen, hydroxy (which itself may be acylated, carbamated or etherified), disubstituted amino, aryl and heteroaryl, then $R^2$ is a group: -E-(Y)n-$R^7$, aryl or heteroaryl.

The scope of the present invention preferably includes the 2-furancarboxylic acid hydrazide compounds of General Formula (I0) below, their prodrugs, their physiologically acceptable salts, their hydrates, their solvates, methods for producing them and pharmaceutical compositions containing them:

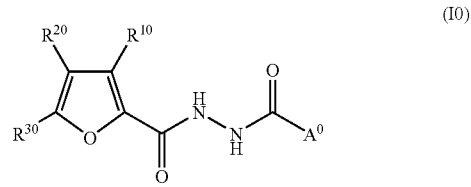

(I0)

wherein $A^0$ is a heteroaryl group other than 2-furyl group that may be substituted by halogen, trifluoromethyl, trifluoromethoxy, trifluoroethoxy, cyano, nitro or $C_{1-3}$ alkylsulfonyl, or a group represented by Formula (a0) below:

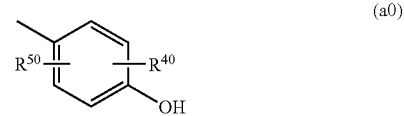

(a0)

wherein $R^{40}$ is a hydrogen atom, a halogen atom, a trifluoromethyl group, a hydroxy group, a $C_{1-6}$ alkyl group, a $C_{2-6}$ alkenyl group, a $C_{2-6}$ alkynyl group, a $C_{1-6}$ alkoxy group, a trifluoromethoxy group, a trifluoroethoxy group, a $C_{1-2}$ alkylsulfonyl group, a cyano group, a nitro group, an amino group, a mono- or di-substituted amino group, a $C_{1-6}$ alkoxycarbonylamino group, a carbamoyl group, a mono- or di-substituted carbamoyl group, a sulfamoyl group, a mono- or di-substituted sulfamoyl group, a $C_{1-6}$ alkylsulfonylamino group, an aryl group, a heteroaryl group, a $C_{1-6}$ alkoxycarbonyl group, an arylmethyloxycarbonyl group, a carboxyl group, a 5-tetrazolyl group, a sulfo group (—SO$_2$OH) or a fluorosulfonyl group.

$R^{50}$ is a hydrogen atom or a halogen atom, either $R^{10}$ or $R^{20}$ is
   a group: -$D^0$-($X^0$)m$^0$-$R^{60}$; or an aryl group or a heteroaryl group optionally substituted by 1 to 4 atoms or groups selected from halogen, hydroxy, hydroxy $C_{1-3}$ alkyl, trifluoromethyl, trifluoromethoxy, trifluoroethoxy, cyano, nitro, amino, disubstituted amino, carbamoyl, sulfamoyl, $C_{1-3}$ alkylsulfonylamino and methylenedioxy, and the other is a group: -$E^0$-($Y^0$)n$^0$-$R^{70}$; a hydrogen atom; a halogen atom; a $C_{1-10}$ alkyl group, a $C_{2-10}$ alkenyl group or a $C_{2-10}$ alkynyl group optionally substituted by 1 to 3 atoms or groups selected from halogen, hydroxy, $C_{1-6}$ alkylcarbonyloxy, arylcarbonyloxy, aryl-substituted $C_{1-4}$ alkylcarbonyloxy, $C_{1-6}$ alkylaminocarbonyloxy, arylaminocarbonyloxy, aryl-substituted $C_{1-4}$ alkylaminocarbonyloxy, $C_{1-6}$ alkyloxy, aryl-substituted $C_{1-4}$ alkyloxy, disubstituted amino, aryl and heteroaryl; a $C_{3-7}$ cycloalkyl group; or an aryl group or a heteroaryl group optionally substituted by 1 to 4 atoms or groups selected from halogen, hydroxy, hydroxy $C_{1-3}$ alkyl, trifluoromethyl, trifluoromethoxy, trifluoroethoxy, cyano, nitro, amino, disubstituted amino, carbamoyl, sulfamoyl, $C_{1-3}$ alkylsulfonylamino and methylenedioxy, $R^{30}$ is a hydrogen atom; a halogen atom; a hydroxy group; a $C_{1-6}$ alkyl group; a $C_{1-6}$ alkoxy group; an aryl group or a heteroaryl group optionally substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl); or an aryl-substituted $C_{1-4}$ alkyl group wherein the aryl moiety may be substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl), $D^0$ and $E^0$ are the same or different, and independently represent an arylene group optionally substituted by 1 to 3 atoms or groups selected from halogen, $C_{1-6}$ alkyl, $C_{1-6}$ alkoxy, trifluoromethyl, trifluoromethoxy and trifluoroethoxy, $X^0$ and $Y^0$ are the same or different, and independently represent —O—, —S—, —SO—, —SO$_2$—, —OSO$_2$—, —NR$^{80}$—, —CO—, —CH=CH—, —C≡C—, —CONH—, —NHCO—, —NHCOO—, —OCH$_2$CONH— or —OCH$_2$CO—, $R^{60}$ and $R^{70}$ are the same or different, and independently represent a $C_{1-10}$ alkyl group; a $C_{2-10}$ alkenyl group; a $C_{2-10}$ alkynyl group; a $C_{3-7}$ cycloalkyl group; a $C_{3-7}$ cycloalkyl-substituted $C_{1-4}$ alkyl group; an aryl group or a heteroaryl group optionally substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl); or an aryl- or heteroaryl-substituted $C_{1-4}$ alkyl group wherein the alkyl moiety may be substituted by hydroxy and the aryl moiety or heteroaryl moiety may be substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl), $R^{80}$ is a hydrogen atom or a $C_{1-10}$ alkylcarbonyl group, and $m^0$ and $n^0$ are independently 0 or 1.

Prodrugs of compounds represented by General Formula (I0) refer to those of General Formula (I0) wherein $R^{10}$, $R^{20}$ and $R^{30}$ are as defined above; and $A^0$ is a heteroaryl group other than a 2-furyl group that may be substituted by halogen, trifluoromethyl, trifluoromethoxy, trifluoroethoxy, cyano, nitro or $C_{1-3}$ alkylsulfonyl; or a group represented by Formula (c) below;

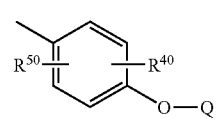

(c)

wherein Q is a hydrogen atom; a $C_{1-6}$ alkyl group; an arylmethyl group whose aryl moiety may be substituted by 1 to 3 groups selected from hydroxy, disubstituted amino and $C_{1-6}$ alkoxy; a hydroxy $C_{1-6}$ alkyl group; a formyl group; a $C_{1-6}$ alkylcarbonyl group; an amino $C_{1-6}$ alkylcarbonyl group; a mono- or di-substituted amino $C_{1-6}$ alkylcarbonyl group; a carboxy $C_{1-6}$ alkylcarbonyl group; an arylcarbonyl group optionally substituted by 1 to 3 groups selected from hydroxy, disubstituted amino and $C_{1-6}$ alkoxy; a $C_{1-6}$ alkoxycarbonyl group; or a phospho group; and $R^{40}$ and $R^{50}$ are as defined above.

Preferable are compounds having General Formula (I0) wherein $A^0$ is represented by Formula (a0), and $R^{10}$, $R^{20}$ and $R^{30}$ are as defined above, and prodrugs, physiologically acceptable salts, hydrates and solvates thereof.

Particularly preferable are those that have General Formula (I0) wherein $A^0$ is represented by Formula (b0):

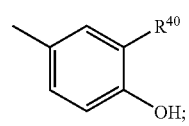

(b0)

wherein either $R^{10}$ or $R^{20}$ is a group: -$D^0$-($X^0$)$m^0$-$R^{60}$; or a phenyl group or an indolyl group optionally substituted by halogen or hydroxy, and the other is a group: -$E^0$-($Y^0$)$n^0$-$R^{70}$, a hydrogen atom, a halogen atom, a $C_{1-10}$ alkyl group, a $C_{2-10}$ alkenyl group, a $C_{2-10}$ alkynyl group, or a phenyl group optionally substituted by halogen or hydroxy, $R^{30}$ is a hydrogen atom, $D^0$ and $E^0$ are phenylene groups, $X^0$ and $Y^0$ are the same or different, and independently represent —O—, —S—, —CH=CH—, —OCH$_2$CONH— or —OCH$_2$CO—, $R^{60}$ and $R^{70}$ are the same or different, and independently represent a $C_{1-10}$ alkyl group, a $C_{2-10}$ alkenyl group, a $C_{2-10}$ alkynyl group, a phenyl $C_{1-4}$ alkyl group, a naphthylmethyl group, a thienylmethyl group or a pyridylmethyl group whose cyclic moiety may be substituted by 1 to 4 atoms or groups selected from halogen, $C_{1-4}$ alkyl, hydroxymethyl, $C_{1-3}$ alkoxy, trifluoromethyl, trifluoromethoxy, nitro, disubstituted amino, carbamoyl, sulfamoyl, methylsulfonylamino, $C_{1-3}$ alkylcarbonylamino, methylenedioxy and phenyl (this phenyl itself being optionally substituted by halogen or trifluoromethyl), and $m^0$ and $n^0$ are as defined above, and prodrugs, physiologically acceptable salts, hydrates and solvates thereof.

Particularly preferable compounds are those that have General Formula (Ia) below, and prodrugs (e.g., compounds wherein the hydroxy group at the 4-position of the benzoyl moiety is substituted by an acetoxy group, a pivaloyloxy group or a benzoyloxy group), physiologically acceptable salts, hydrates and solvates thereof:

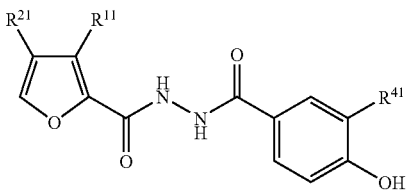

(Ia)

wherein $R^{41}$ is a halogen atom, a trifluoromethyl group, an ethynyl group, a methylsulfonyl group, a cyano group, a nitro group, a tert-butoxycarbonyl group or a carbamoyl group, $R^{11}$ is a halogen atom; a vinyl group; an ethynyl group; or a phenyl group or an indolyl group optionally substituted by a group: —$X^1$—$R^{61}$, $C_{1-10}$ alkyl, halogen or hydroxy, when $R^{11}$ is a halogen atom; a vinyl group; an ethynyl group, $R^{21}$ is a phenyl group optionally substituted by a group: —$Y^1$—$R^{71}$, $C_{1-10}$ alkyl, halogen or hydroxy, and when $R^{11}$ is a phenyl group or an indolyl group optionally substituted by a group: —$X^1$—$R^{61}$, $C_{1-10}$ alkyl, halogen or hydroxy, $R^{21}$ is a hydrogen atom; a halogen atom; a vinyl group; an ethynyl group; or a phenyl group optionally substituted by a group: —$Y^1$—$R^{71}$, $C_{1-10}$ alkyl, halogen or hydroxy, wherein $X^1$ and $Y^1$ are the same or different, and independently represent —O—, —S—, —CH═CH—, —OCH$_2$CONH— or —OCH$_2$CO—, and $R^{61}$ and $R^{71}$ are the same or different, and independently represent a $C_{1-10}$ alkyl group, a $C_{2-10}$ alkenyl group, a $C_{2-10}$ alkynyl group, a phenyl $C_{1-4}$ alkyl group, a naphthylmethyl group or a pyridylmethyl group, in which the cyclic moiety of these groups (for example, a cyclic $C_{2-10}$ alkenyl group, a cyclic $C_{2-10}$ alkynyl group, a phenyl moiety, a naphthyl moiety and a pyridyl moiety) may be substituted by 1 to 4 atoms or groups selected from halogen, $C_{1-4}$ alkyl, hydroxymethyl, $C_{1-3}$ alkoxy, trifluoromethyl, trifluoromethoxy, nitro, disubstituted amino, carbamoyl, sulfamoyl, methylsulfonylamino, $C_{1-3}$ alkylcarbonylamino, methylenedioxy and phenyl (this phenyl itself being optionally substituted by halogen or trifluoromethyl).

Further preferable compounds of the present invention are those that have General Formula (Ia) wherein $R^{41}$ is a cyano group or a nitro group, and $R^{11}$ and $R^{21}$ are as defined above, and prodrugs (e.g., compounds wherein the hydroxy group at the 4-position of the benzoyl moiety is replaced by an acetoxy group, a pivaloyloxy group or a benzoyloxy group), physiologically acceptable salts, hydrates and solvates thereof.

Especially preferable compounds of the present invention are those that have General Formula (Ia) wherein $R^{41}$ is a cyano group or an nitro group, $R^{11}$ is a phenyl group or an indolyl group optionally substituted by a group: —$X^1$—$R^{61}$, $C_{1-10}$ alkyl, halogen or hydroxy, $R^{21}$ is a hydrogen atom or a phenyl group optionally substituted by $C_{1-10}$ alkyl, halogen or hydroxy, $X^1$ and $R^{61}$ are as defined above, and $X^1$ is bound to the 3- or 4-position of the phenyl group, and prodrugs (e.g., compounds wherein the hydroxy group at the 4-position of the benzoyl moiety is substituted by an acetoxy group, a pivaloyloxy group or a benzoyloxy group), physiologically acceptable salts, hydrates and solvates thereof.

Especially particularly preferable other compounds of the present invention are those that have General Formula (Ia) wherein $R^{41}$ is a cyano group or a nitro group, $R^{11}$ is a phenyl group optionally substituted by hydroxy, $C_{1-6}$ alkyl or $C_{1-6}$ alkoxy, $R^{21}$ is a phenyl group optionally substituted by a group: —$Y^1$—$R^{71}$, $Y^1$ and $R^{71}$ are as defined above, and $Y^1$ is bound to the 3- or 4-position of the phenyl group, and prodrugs (e.g., compounds wherein the hydroxy group at the 4-position of the benzoyl moiety is substituted by an acetoxy group, a pivaloyloxy group or a benzoyloxy group), physiologically acceptable salts, hydrates and solvates thereof.

Among the compounds of the present invention, especially preferable are the compounds whose specific examples are given below; and prodrugs (e.g., compounds wherein the hydroxy group at the 4-position of the benzoyl moiety is substituted by an acetoxy group, a pivaloyloxy group or a benzoyloxy group), physiologically acceptable salts, hydrates and solvates thereof:

3,4-Diphenyl-2-furancarboxylic acid 2-(3-cyano-4-hydroxybenzoyl)hydrazide (compound of Example 18), 3,4-Diphenyl-2-furancarboxylic acid 2-(4-hydroxy-3-nitrobenzoyl)hydrazide (compound of Example 19), 3-[3-(2,3,5,6-Tetramethylbenzyloxy)phenyl]-2-furancarboxylic acid 2-(3-cyano-4-hydroxybenzoyl)hydrazide (compound of Example 1), 3-[4-(2,3,5,6-Tetramethylbenzyloxy)phenyl]-2-furancarboxylic acid 2-(3-cyano-4-hydroxybenzoyl)hydrazide (compound of Example 15), 3-[3-(2,3,5,6-Tetramethylbenzyloxy)phenyl]-2-furancarboxylic acid 2-(4-hydroxy-3-nitrobenzoyl)hydrazide (compound of Example 20), 3-[4-(2,3,5,6-Tetramethylbenzyloxy)phenyl]-2-furancarboxylic acid 2-(4-hydroxy-3-nitrobenzoyl)hydrazide (compound of Example 113), 4-Phenyl-3-[3-(2,3,5,6-tetramethylbenzyloxy)phenyl]-2-furancarboxylic acid 2-(3-cyano-4-hydroxybenzoyl)hydrazide (compound of Example 98), 3-Phenyl-4-[3-(2,3,5,6-tetramethylbenzyloxy)phenyl]-2-furancarboxylic acid 2-(3-cyano-4-hydroxybenzoyl)hydrazide (compound of Example 99), 4-Phenyl-3-[3-(2,3,5,6-tetramethylbenzyloxy)phenyl]-2-furancarboxylic acid 2-(4-hydroxy-3-nitrobenzoyl)hydrazide (compound of Example 100), 3-(3-Benzyloxyphenyl)-2-furancarboxylic acid 2-(3-cyano-4-hydroxybenzoyl)hydrazide (compound of Example 3), 3-(3-Benzyloxyphenyl)-2-furancarboxylic acid 2-(4-hydroxy-3-nitrobenzoyl)hydrazide (compound of Example 101), 3-(3-Phenoxyphenyl)-2-furancarboxylic acid 2-(3-cyano-4-hydroxybenzoyl)hydrazide (compound of Example 2), 3-(3-Phenethyloxyphenyl)-2-furancarboxylic acid 2-(3-cyano-4-hydroxybenzoyl)hydrazide (compound of Example 4), 3-(3-Phenethyloxyphenyl)-2-furancarboxylic acid 2-(4-hydroxy-3-nitrobenzoyl)hydrazide (compound of Example 209), 3-[3-(4-Pyridylmethyloxy)phenyl]-2-furancarboxylic acid 2-(3-cyano-4-hydroxybenzoyl)hydrazide (compound of Example 102), 3-[3-(4-Methylsulfonylbenzyloxy)phenyl]-2-furancarboxylic acid 2-(4-hydroxy-3-nitrobenzoyl)hydrazide (compound of Example 120), 3-[3-(4-Methylsulfonylbenzyloxy)phenyl]-2-furancarboxylic acid 2-(3-cyano-4-hydroxybenzoyl)hydrazide (compound of Example 136), 3-Phenyl-2-furancarboxylic acid 2-(3-cyano-4-hydroxybenzoyl)hydrazide (compound of Example 61), 3-Phenyl-2-furancarboxylic acid 2-(4-hydroxy-3-nitrobenzoyl)hydrazide (compound of Example 143), 3-[3-(2-Methylbenzyloxy)phenyl]-2-furancarboxylic acid 2-(4-hydroxy-3-nitro benzoyl)hydrazide (compound of Example 119), 3-[3-(3-Methylbenzyloxy)phenyl]-2-furancarboxylic acid 2-(4-hydroxy-3-nitrobenzoyl)hydrazide (compound of Example 123), 3-[3-(4-Methylbenzyloxy)phenyl]-2-furancarboxylic acid 2-(4-hydroxy-3-nitrobenzoyl)hydrazide (compound of Example 126), 3-[3-(2,5-Dimethylbenzyloxy)phenyl]-2-furancarboxylic acid 2-(4-hydroxy-3-nitrobenzoyl)hydrazide (compound of Example 127), 3-[3-(3,4-Dimethylbenzyloxy)phenyl]-2-furancarboxylic acid 2-(4-hydroxy-3-nitrobenzoyl)hydrazide (compound of Example 129), 3-[3-(2,4-Dimethylbenzyloxy)phenyl]-2-furancarboxylic acid 2-(4-hydroxy-3-nitrobenzoyl)hydrazide (compound of Example 128), 3-[3-(2-Methylsulfonylaminobenzyloxy)phenyl]-2-furancarboxylic acid 2-(4-hydroxy-3-nitrobenzoyl)hydrazide (compound of Example 138), 3-(4-Butylphenyl)-2-furancarboxylic acid 2-(4-hydroxy-3-nitrobenzoyl)hydrazide (compound of Example 142), 3-(3-Methylphenyl)-2-furancarboxylic acid 2-(4-hydroxy-3-nitrobenzoyl)hydrazide (compound of Example 145), 3-(4-Methylphenyl)-2-furancarboxylic acid 2-(4-hydroxy-3-nitrobenzoyl)hydrazide (compound of Example 146), 3-(3,4-Dimethylphenyl)-2-furancarboxylic acid 2-(4-hydroxy-3-nitrobenzoyl)hydrazide (compound of Example 150), 3-(3-Isopropylphenyl)-2-furancarboxylic acid 2-(4-hydroxy-3-nitrobenzoyl)hydrazide (compound of Example 152), 3-(4-Isopropylphenyl)-2-furancarboxylic acid 2-(4-hydroxy-3-nitrobenzoyl)hydrazide (compound of Example 153), 3-(4-Ethylphenyl)-2-furancarboxylic acid 2-(4-hydroxy-3-nitrobenzoyl)hydrazide (compound of Example 156), 3-(4-Hexylphenyl)-2-furancarboxylic acid 2-(4-hydroxy-3-nitrobenzoyl)hydrazide (compound of Example 158), 3-(4-Pentyloxyphenyl)-2-furancarboxylic acid 2-(4-hydroxy-3-nitrobenzoyl)hydrazide (compound of Example 159), 3-(4-Propylphenyl)-2-furancarboxylic acid 2-(4-hydroxy-3-nitrobenzoyl)hydrazide (compound of Example 160), 3-(4-Pentylphenyl)-2-furancarboxylic acid 2-(4-hydroxy-3-nitrobenzoyl)hydrazide (compound of Example 162), 3-[3-(2-Methoxy-5-pyridylmethyloxy)phenyl]-2-furancarboxylic acid 2-(4-hydroxy-3-nitrobenzoyl)hydrazide (compound of Example 164), 3-[3-(4-Methoxybenzyloxy)phenyl]-2-furancarboxylic acid 2-(4-hydroxy-3-nitrobenzoyl)hydrazide (compound of Example 176), 3-[3-(2-Acetylaminobenzyloxy)phenyl]-2-furancarboxylic acid 2-(4-hydroxy-3-nitrobenzoyl)hydrazide (compound of Example 179), 3-(3-Isopentyloxyphenyl)-2-furancarboxylic acid 2-(4-hydroxy-3-nitrobenzoyl)hydrazide (compound of Example 180), 3-(3-Butoxyphenyl)-2-furancarboxylic acid 2-(4-hydroxy-3-nitrobenzoyl)hydrazide (compound of Example 181), 3-(3-Pentyloxyphenyl)-2-furancarboxylic acid 2-(4-hydroxy-3-nitrobenzoyl)hydrazide (compound of Example 182), 3-(3-Isobutoxyphenyl)-2-furancarboxylic acid 2-(4-hydroxy-3-nitrobenzoyl)hydrazide (compound of Example 183), 3-(3-Hexyloxyphenyl)-2-furancarboxylic acid 2-(4-hydroxy-3-nitrobenzoyl)hydrazide (compound of Example 184), 3-(3-Heptyloxyphenyl)-2-furancarboxylic acid 2-(4-hydroxy-3-nitrobenzoyl)hydrazide (compound of Example 185), 3-(3-Hexylphenyl)-2-furancarboxylic acid 2-(4-hydroxy-3-nitrobenzoyl)hydrazide (compound of Example 188), 3-(3-Benzylphenyl)-2-furancarboxylic acid 2-(4-hydroxy-3-nitrobenzoyl)hydrazide (compound of Example 189), 3-(3-Pentylphenyl)-2-furancarboxylic acid 2-(4-hydroxy-3-nitrobenzoyl)hydrazide (compound of Example 192), 3-[3-(3-Methyl-2-butenyloxy)phenyl]-2-furancarboxylic acid 2-(4-hydroxy-3-nitrobenzoyl)hydrazide (compound of Example 196), 3-[3-(2-Methyl-2-propenyloxy)phenyl]-2-furancarboxylic acid 2-(4-hydroxy-3-nitrobenzoyl)hydrazide (compound of Example 197), 3-[3-(2-Butenyloxy)phenyl]-2-furancarboxylic acid 2-(4-hydroxy-3-nitrobenzoyl)hydrazide (compound of Example 198), and 3-[3-(2-Allyloxy)phenyl]-2-furancarboxylic acid 2-(4-hydroxy-3-nitrobenzoyl)hydrazide (compound of Example 199).

In addition to the especially preferable compounds listed above, and the compounds described in the examples hereinbelow, specific examples of compounds of the present invention include those shown in Table 2 below and prodrugs thereof (e.g., compounds wherein the hydroxy group at the 4-position of the benzoyl moiety is substituted by an acetoxy group, a pivaloyloxy group or a benzoyloxy group).

The following abbreviations may be used in Table 2, and in Tables 7 and 9 of the following examples in order to simplify the description. For the groups themselves having substituents, such substituents are specified in parentheses immediately after the group: Ac: acetyl group, Bn: benzyl group, Bu$^t$: tert-butyl group, Et: ethyl group, iPr: isopropyl group, Me: methyl group, MDO: methylenedioxy group, Morph: morpholino group, Naph: naphthyl group, Ph: phenyl group, Py: pyridyl group, Pyrr: 1-pyrrolidinyl group.

Therefore, for example, "Ph[3-OCH$_2$(3-Py)]" denotes 3-(3-pyridylmethoxy)phenyl group, "Ph[3-OBn(2-Cl-4,5-MDO)]" denotes 3-(2-chloro-4,5-methylenedioxy-benzyloxy)phenyl group, and "Ph[3-OCH$_2$CONHPh[3,5-(OMe)$_2$]]" denotes 3-[(3,5-dimethoxyphenyl)carbamoylmethoxy]phenyl group.

TABLE 2

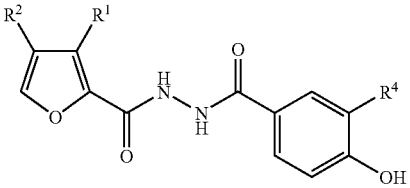

| R¹ | R² | R⁴ |
|---|---|---|
| Ph[3-OCH₂(3-Py)] | H | CN |
| Ph[3-OCH₂(3-Py)] | H | CF₃ |
| Ph[3-OCH₂(3-Py)] | H | CONH₂ |
| Ph[3-OCH₂(3-Py)] | H | COOBuᵗ |
| Ph[3-OCH₂(3-Py)] | H | C≡CH |
| Ph[3-OCH₂(2-Py)] | H | CN |
| Ph[3-OCH₂(2-Py)] | H | CF₃ |
| Ph[3-OCH₂(2-Py)] | H | CONH₂ |
| Ph[3-OCH₂(2-Py)] | H | COOBuᵗ |
| Ph[3-OCH₂(2-Py)] | H | C≡CH |
| Ph[3-OCH₂(4-Py)] | H | CF₃ |
| Ph[3-OCH₂(4-Py)] | H | CONH₂ |
| Ph[3-OCH₂(4-Py)] | H | COOBuᵗ |
| Ph[3-OCH₂(4-Py)] | H | C≡CH |
| Ph[3-OCH₂(1-Naph)] | H | CN |
| Ph[3-OCH₂(2-Naph)] | H | CN |
| Ph[3-OBn(3-OMe)] | H | CN |
| Ph[3-OBn(2-OMe)] | H | CN |
| Ph[3-OBn(4-OMe)] | H | CN |
| Ph[3-OCH₂CH₂Ph(4-OMe)] | H | NO₂ |
| Ph[3-OBn(4-OCF₃)] | H | NO₂ |
| Ph[3-OBn(4-OCF₃)] | H | CN |
| Ph[3-OBn(4-iPr)] | H | NO₂ |
| Ph[3-OBn(4-iPr)] | H | CN |
| Ph[3-OCH₂[5-Py(2-Cl)]] | H | CN |
| Ph[3-OCH₂[3-Py(4,5-Cl₂)]] | H | SO₂Me |
| Ph[3-OCH₂[4-Py(2,6-Cl₂)]] | H | SO₂Me |
| Ph[3-OCH₂[4-Py(2,6-Cl₂)]] | H | NO₂ |
| Ph[3-OCH₂[4-Py(2,6-Cl₂)]] | H | CN |
| Ph[3-OCH₂[2-Py(4-Me)]] | H | NO₂ |
| Ph[3-OCH₂[2-Py[3,4-(OMe)₂]]] | H | CN |
| Ph[3-OBn(4-NHAc)] | H | NO₂ |
| Ph[3-OBn(4-NO₂)] | H | NO₂ |
| Ph[3-OBn(2-NMe₂)] | H | NO₂ |
| Ph[3-OBn(2-NMe₂)] | H | CN |
| Ph[3-OCH₂CH₂Ph(2-NMe₂)] | H | NO₂ |
| Ph[3-OBn(3-NMe₂)] | H | NO₂ |
| Ph[3-OBn(3-NMe₂)] | H | CN |
| Ph[3-OCH₂CH₂Ph(3-NO₂)] | H | NO₂ |
| Ph[3-OCH₂CH₂Ph(3-NEtMe)] | H | NO₂ |
| Ph[3-OBn(4-NMe₂)] | H | NO₂ |
| Ph[3-OBn(4-NMe₂)] | H | CN |
| Ph[3-OCH₂CH₂Ph(4-NEt₂)] | H | NO₂ |
| Ph[3-OBn[4-(1-Pyrr)]] | H | NO₂ |
| Ph[3-OBn(4-Morph)] | H | NO₂ |
| Ph[3-OBn(3,4-Cl₂)] | H | NO₂ |
| Ph[3-OBn(3,4-Cl₂)] | H | CN |
| Ph[3-OBn(4-CF₃)] | H | NO₃ |
| Ph[3-OBn(4-CF₃)] | H | CN |
| Ph[3-OBn[2,3,4-(OMe)₃]] | H | NO₂ |
| Ph[3-OBn[2,3,4-(OMe)₃]] | H | CN |
| Ph[3-OBn[3,5-(OMe)₂]] | H | NO₂ |
| Ph[3-OBn[3,5-(OMe)₂]] | H | CN |
| Ph[3-OBn[2,5-(OMe)₂]] | H | SO₂Me |
| Ph[3-OBn[2,3-(OMe)₂]] | H | SO₂Me |
| Ph[3-OBn(3-CH₂OH)] | H | SO₂Me |
| Ph[3-OBn(5,6-Cl₂-3-CH₂OH)] | H | NO₂ |
| I | Ph[3-OBn(2,3,5,6-Me₄)] | NO₂ |
| I | Ph[3-OBn(2,3,5,6-Me₄)] | CN |
| Ph[3-OBn(2,3,5,6-Me₄)] | —C≡CH | NO₂ |
| Ph[3-OBn(2,3,5,6-Me₄)] | —C≡CH | CN |
| Ph[3-OBn(2,3,5,6-Me₄)] | —CH=CH₂ | NO₂ |
| Ph[3-OBn(2,3,5,6-Me₄)] | —CH=CH₂ | CN |
| —C≡CH | Ph[3-OBn(2,3,5,6-Me₄)] | NO₂ |
| —C≡CH | Ph[3-OBn(2,3,5,6-Me₄)] | CN |
| —CH=CH₂ | Ph[3-OBn(2,3,5,6-Me₄)] | NO₂ |
| —CH=CH₂ | Ph[3-OBn(2,3,5,6-Me₄)] | CN |
| Ph[3-OBn(2-Cl-4,5-MDO)] | H | NO₂ |
| Ph[3-OBn(2-Cl-4,5-MDO)] | H | CN |
| Ph[3-OCH₂[2-Py(6-Me)]] | H | CN |
| Ph[3-OBn(4-Buᵗ)] | H | NO₂ |
| Ph[3-OBn(4-Buᵗ)] | H | CN |
| Ph | Ph(4-OH) | NO₂ |
| Ph | Ph(4-OH) | CN |
| Ph | Ph(4-OH) | CF₃ |
| Ph(4-OH) | Ph | NO₂ |
| Ph(4-OH) | Ph | CN |
| Ph(4-OH) | Ph | CF₃ |
| Ph | Ph[3-OBn(2,3,5,6-Me₄)] | NO₂ |
| Ph | Ph(4-OMe) | NO₂ |
| Ph | Ph(4-OMe) | CF₃ |
| Ph(4-OMe) | Ph | NO₂ |
| Ph(4-OMe) | Ph | CN |
| Ph(4-OMe) | Ph | CF₃ |
| Ph(3-OBn) | Ph | NO₂ |
| Ph(3-OBn) | Ph | CN |
| Ph(3-OCH₂CH₂Ph) | Ph | NO₂ |
| Ph(3-OCH₂CH₂Ph) | Ph | CN |
| Ph[3-OBn(2,3,5,6-Me₄)] | H | CF₃ |
| Ph[3-OBn(2,3,5,6-Me₄)] | H | CONH₂ |
| Ph[3-OBn(2,3,5,6-Me₄)] | H | COOBuᵗ |
| Ph[3-OBn(2,3,5,6-Me₄)] | H | C≡CH |
| Ph[4-OBn(2,3,5,6-Me₄)] | H | CF₃ |
| Ph[4-OBn(2,3,5,6-Me₄)] | H | CONH₂ |
| Ph[4-OBn(2,3,5,6-Me₄)] | H | COOBuᵗ |
| Ph[4-OBn(2,3,5,6-Me₄)] | H | C≡CH |
| Ph(3-OBn) | H | CF₃ |
| Ph(3-OBn) | H | CONH₂ |
| Ph(3-OBn) | H | COOBuᵗ |
| Ph(3-OBn) | H | C≡CH |
| Ph(3-OCH₂CH₂Ph) | H | CF₃ |
| Ph(3-OCH₂CH₂Ph) | H | CONH₂ |
| Ph(3-OCH₂CH₂Ph) | H | COOBuᵗ |
| Ph(3-OCH₂CH₂Ph) | H | C≡CH |
| Ph[3-OBn(2,3,5,6-Me₄)] | Ph | CF₃ |
| Ph[3-OBn(2,3,5,6-Me₄)] | Ph | CONH₂ |
| Ph[3-OBn(2,3,5,6-Me₄)] | Ph | COOBuᵗ |
| Ph[3-OBn(2,3,5,6-Me₄)] | Ph | C≡CH |
| Ph[4-OBn(2,3,5,6-Me₄)] | Ph | CF₃ |
| Ph[4-OBn(2,3,5,6-Me₄)] | Ph | CONH₂ |
| Ph[4-OBn(2,3,5,6-Me₄)] | Ph | COOBuᵗ |
| Ph[4-OBn(2,3,5,6-Me₄)] | Ph | C≡CH |
| Ph(3-OBn) | Ph | CF₃ |
| Ph(3-OBn) | Ph | CONH₂ |
| Ph(3-OBn) | Ph | COOBuᵗ |
| Ph(3-OBn) | Ph | C≡CH |
| Ph(3-OCH₂CH₂Ph) | Ph | CF₃ |
| Ph(3-OCH₂CH₂Ph) | Ph | CONH₂ |
| Ph(3-OCH₂CH₂Ph) | Ph | COOBuᵗ |
| Ph(3-OCH₂CH₂Ph) | Ph | C≡CH |
| Ph | Ph | CONH₂ |
| Ph | Ph | COOBuᵗ |
| Ph | Ph | C≡CH |
| Ph | Ph[3-OBn(2,3,5,6-Me₄)] | CF₃ |
| Ph(3-OCH₂CONHPh) | H | NO₂ |
| Ph(3-OCH₂CONHPh) | H | CN |
| Ph[3-OCH₂CONH[2-Py(4-Me)]] | H | NO₂ |
| Ph[3-OCH₂CONH[2-Py(4-Me)]] | H | CN |
| Ph[3-OCH₂CONH[2-Py(3-Cl-5-CF₃)]] | H | NO₂ |
| Ph[3-OCH₂CONHPh(4-F)] | H | NO₂ |
| Ph[3-OCH₂CONHPh(4-F)] | H | CN |
| Ph[3-OCH₂CONHPh(4-OMe)] | H | NO₂ |
| Ph[3-OCH₂CONHPh(4-OMe)] | H | CN |

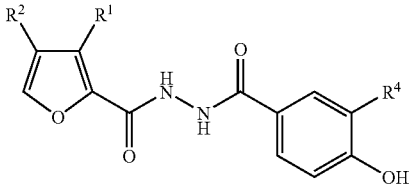

TABLE 2-continued

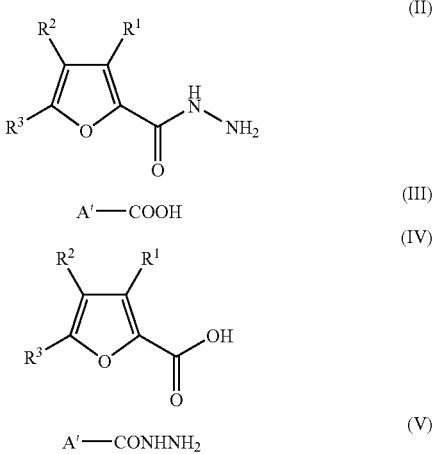

| R¹ | R² | R⁴ |
|---|---|---|
| Ph[3-OCH$_2$CONHPh(4-SO$_2$NH$_2$)] | H | NO$_2$ |
| Ph[3-OCH$_2$CONHPh[3,5-(OMe)$_2$]] | H | NO$_2$ |
| Ph[3-OCH$_2$CONHPh[3,5-(OMe)$_2$]] | H | CN |
| Ph[3-OCH$_2$CONHPh(4-iPr)] | H | NO$_2$ |
| Ph[3-OCH$_2$CONHPh(4-iPr)] | H | CN |
| Ph[3-OCH$_2$CONHPh(4-CF$_3$)] | H | NO$_2$ |
| Ph[3-OCH$_2$CONHPh(4-CF$_3$)] | H | CN |
| Ph[3-OCH$_2$CONHPh(4-Bu$^t$)] | H | NO$_2$ |
| Ph[3-OCH$_2$CONHPh(4-Bu$^t$)] | H | CN |
| Ph[3-CH=CH-CH$_2$(2-Py)] | H | NO$_2$ |
| Ph[3-CH=CH-CH$_2$(2-Py)] | H | CN |
| Ph[3-CH=CH-Ph(4-OMe)] | H | NO$_2$ |
| Ph[3-CH=CH-Ph(3-NO$_2$)] | H | NO$_2$ |
| Ph[3-CH=CH-Ph(2-NMe$_2$)] | H | NO$_2$ |
| Ph[3-CH=CH-Ph(3-NEtMe)] | H | NO$_2$ |
| Ph[3-CH=CH-Ph(4-NEt$_2$)] | H | NO$_2$ |
| Ph[3-CH=CH-CH$_2$Ph(4-OMe)] | H | NO$_2$ |
| Ph[3-CH=CH-CH$_2$Ph(4-OMe)] | H | CN |
| Ph[3-CH=CH-CH$_2$Ph[3,5-(OMe)$_2$]] | H | NO$_2$ |
| Ph[3-CH=CH-CH$_2$Ph[3,5-(OMe)$_2$]] | H | CN |
| Ph[3-OCH$_2$CO(3-Py)] | H | NO$_2$ |
| Ph[3-OCH$_2$CO(3-Py)] | H | CN |
| Ph[3-OCH$_2$COPh(4-OMe)] | H | NO$_2$ |
| Ph[3-OCH$_2$COPh(4-OMe)] | H | CN |
| Ph[3-OCH$_2$COPh[2,4-(OMe)$_2$]] | H | NO$_2$ |
| Ph[3-OCH$_2$COPh[2,4-(OMe)$_2$]] | H | CN |
| Ph[3-OCH$_2$COPh(4-SO$_2$NEt$_2$)] | H | NO$_2$ |
| Ph[3-OCH$_2$COPh(4-NHSO$_2$Me)] | H | NO$_2$ |
| Ph[3-OCH$_2$COPh[4-(1-Pyrr)]] | H | NO$_2$ |

The compounds of General Formula (I) and prodrugs thereof can be prepared by, for example, reacting compounds of the following Formula (II) with compounds of the following Formula (III) or reactive derivatives thereof whose carboxyl group is activated, or by reacting compounds of the following Formula (IV) or reactive derivatives thereof whose carboxyl group is activated with compounds of the following Formula (V); and, as necessary, by converting the reaction products to the compounds of Formula (I):

(II)

(III) A'—COOH (IV)

(V) A'—CONHNH$_2$ wherein A' is identical to the group represented by A defined above, or a group in which the hydroxy group at the 4-position of A is etherified, acylated or carbamated; and R¹, R² and R³ are as defined above.

Specific examples of hydrazidation are described in Reference Examples 4, 18, 31, 32, 40, 72, 73, 89, etc.

Examples of activated carboxyl derivatives of the compounds of Formulae (III) and (IV) include activated esters, acid anhydrides and acid halides (especially acid chlorides). Specific examples of activated esters include p-nitrophenyl esters, N-hydroxysuccinimide esters and pentafluorophenyl esters. Specific examples of acid anhydrides include symmetrical acid anhydrides and mixed acid anhydrides prepared with ethyl chlorocarbonate, isobutyl chlorocarbonate, isovaleric acid, pivalic acid, etc.

The reaction of a compound of Formula (II) with a compound of Formula (III) or an activated carboxyl derivative thereof, and the reaction of a compound of Formula (IV) or an activated carboxyl derivative thereof with a compound of Formula (V) are carried out under conditions which are usually used for amide bond formation reactions.

When a compound of Formula (III) or (IV) is used, the reaction is usually carried out in the presence of a condensing agent. Specific examples of condensing agents include N,N'-dicyclohexylcarbodiimide, 1-ethyl-3-(3-dimethylaminopropyl)carbodiimide hydrochloride (WSC), N,N'-carbonyldiimidazole, benzotriazole-1-yloxytris(pyrrolidino)phosphonium hexafluorophosphate (PyBOP reagent) and benzotriazole-1-yloxytris(dimethylamino)phosphonium hexafluorophosphate (BOP reagent). These condensing agents can be used singly or in combination with peptide synthesis reagents such as N-hydroxysuccinimide, 1-hydroxybenzotriazole and the like.

The reaction of a compound of Formula (II) with a compound of Formula (III) or an activated carboxyl derivative thereof, and the reaction of a compound of Formula (V) with a compound of Formula (IV) or an activated carboxyl derivative thereof may be carried out in the presence or absence of solvent. The solvents can be selected according to the type of starting compounds. Examples include toluene, tetrahydrofuran, dioxane, ethylene glycol diethyl ether, dichloromethane, chloroform, ethyl acetate, acetone, acetonitrile, dimethylformamide, 1,3-dimethyl-2-imidazolidinone and 1-methyl-2-pyrrolidinone. Such solvents can be used singly or in combination of two or more.

These reactions may be carried out in the presence of a base, if necessary. Specific examples of bases are inorganic bases such as potassium carbonate and sodium bicarbonate, and organic bases such as triethylamine, ethyldiisopropylamine, N-methylmorpholine, pyridine and 4-dimethylaminopyridine. Although the reaction temperature varies according to the type of starting compounds, it is usually about 0 to about 100° C.

When there is a functional group which may be involved in the reaction exists in the structure of compound (II), (III), (IV) or (V), it is preferable to protect it according to a conventional method and remove the protecting group after the reaction. The trialkylsilyl group such as tert-butyldimethylsilyl is, for example, preferable as a protecting group for alcoholic hydroxy group. Removal of such a protecting group can be readily performed by treating the reaction products with tetrabutylammonium fluoride in tetrahydrofuran, thereby converting the reaction products into compounds of Formula (I) having an alcoholic hydroxy group. This reaction is specifically described in Reference Example 43.

When compounds of Formula (I) wherein a lower alkoxy group is substituted for a phenolic hydroxy group are obtained, these can be converted to compounds of Formula (I) having a phenolic hydroxy group by treating them according to conventional methods under conditions suitable for phenolic ether cleavage. The cleavage conditions can be suitably selected according to the type of reaction product. Such reaction products can be readily converted to compounds of Formula (I) having a phenolic hydroxy group by, for example, treating the reaction products with boron tribromide in dichloromethane or with pyridine hydrochloride in the absence of solvent. When compounds of Formula (I) wherein a benzyloxy group is substituted for the phenolic hydroxy group are obtained, these can be converted to compounds of Formula (I) containing a phenolic hydroxy group by hydrogenolysis according to conventional methods. When compounds of Formula (I) wherein an alkylcarbonyloxy group is substituted for the phenolic hydroxy group are obtained, these can be converted to the compounds of Formula (I) containing phenolic hydroxy by hydrolysis according to conventional methods. Moreover, the compounds of Formula (I) containing a phenolic hydroxy group can be converted to prodrugs of the compounds of Formula (I) by reaction with various alkylating agents, carboxylic acids or their reactive derivatives, or inorganic acids or their reactive derivatives according to conventional methods.

The starting compounds in the methods of the aforementioned preparation, i.e., compounds (II), (III), (IV) and (V), can be prepared by known methods, or are readily available since they are commercially available. Typical production methods are described hereinbelow.

A method for preparing the compounds of Formula (IV) is described first since they can be regarded as intermediates in the preparation of the compounds of Formula (II).

The compounds of Formula (IV) or activated carboxyl derivatives thereof can be prepared, as described hereinbelow, by combining synthetic methods and reactions known in the field of furan compounds.

1. Introduction of a Carboxyl Group to 2-Position of a Furan Skeleton

A carboxyl group can be introduced to 2-position of the furan skeleton according to or with reference to the methods described in *Bull. Soc. Chim.* 1970, 1838-1846; *J. Chem. Soc., Perkin Trans. II* 1998, 679-689; *Synth. Commun.* 1998, 28, 1093-1096; and Reference Examples 36-39 and 42. Using these methods, 2-furancarboxylic acid compounds can be prepared from 2-position-unsubstituted furan compounds. Such 2-position-unsubstituted furan compounds to be used in such reactions can be prepared, for example, according to or with reference to the methods described in the above references and Reference Examples.

2. Introduction of Substituted or Unsubstituted (hetero)aryl into a Furan Skeleton A 2-furancarboxylic acid compound having substituted or unsubstituted (hetero)aryl at the 3, 4 and/or 5 positions can be prepared by reacting a 2-furancarboxylic acid compound having bromine at the 3-, 4- and/or 5-positions with substituted or unsubstituted (hetero)arylboronic acid in the presence of a palladium catalyst such as tetrakis(triphenylphosphine)palladium and a base such as cesium carbonate. Specific examples of this reaction are given in Reference Examples 2, 5, 10-14, 17, 19, 23, 30, 54, 56, 58-61, 69, 71, 76-78, 79, 81 and 87.

2-Furancarboxylic acid compounds having bromine at the 3, 4 and/or 5 positions are commercially available or can be prepared according to or with reference to known methods or the methods described in the references cited in Reference Examples 1 and 10.

Substituted or unsubstituted (hetero)arylboronic acids are commercially available or can be prepared according to or with reference to known methods, for example, the methods described in Reference Examples 16 and 29 using as starting materials bromo(hetero)aryl derivatives. Bromo(hetero)aryl derivatives are commercially available and can be prepared according to or with reference to known methods, methods described in Reference Examples 15 and 28, etc.

When the substituted aryl group is benzyloxyaryl in the furan skeleton, the compound can be converted to a furan compound having a hydroxyaryl group by hydrogenolysis. When furan compounds having a hydroxyaryl group are reacted according to conventional methods with various alkylating agents or substituted aryl alkylating agents under alkylating reaction conditions, the compounds wherein the hydroxy group is converted into the alkoxy group or the substituted arylalkyloxy group can be obtained. Specific examples of this reaction are given in Reference Examples 3, 6-9, 20, 21, 27, 28 and 70.

2-Furancarboxylic acid compounds having a hydroxyaryl group can be converted to 2-furancarboxylic acid compounds having various types of substituents such as a benzylaryl group by, for example, reaction with trifluoromethanesulfonic acid anhydride to convert the hydroxy group into the trifluoromethylsulfonyloxy group and then with organozinc reagents such as benzyl zinc bromide. Reference Examples 24 and 25 give specific embodiments of this reaction.

3. Synthesis of Carboxylic Acid Compounds having Identical Unsubstituted or Substituted (hetero)aryls at 3- and 4-Positions A 2-furancarboxylic acid compound having identical unsubstituted or substituted (hetero)aryls at 3- and 4-positions can be prepared according to the method described in *Journal of the Pharmaceutical Society of Japan* 1974, 94, 1312-1321.

4. Introduction of Leaving Group, and Subsequent Substitution Reaction Thereof

As demonstrated in Reference Examples 52 and 55, when 2-furancarboxylic acid compounds having a phenyl group at 3-position or at 3- and 4-positions are reacted with bromine, 5-position thereof is easily brominated.

The bromine atom at 5-position of 2-furancarboxylic acid compounds can be readily converted to a $C_{1-6}$ alkoxy group as demonstrated in Reference Example 53. Moreover, this bromine atom can be converted to a $C_{1-6}$ alkyl group or an aryl-substituted $C_{1-4}$ alkyl group according to the method described in Reference Example 25.

5. Modification of Functional Groups Located in Side Chains

The alcoholic hydroxy group located in side chains can be acylated, carbamated, acetoxylated, substituted- or unsubstituted-aminocarbonylmethylated, or etherified according to conventional methods. Reference Examples 44-47 give specific embodiments.

A hydroxymethyl group is readily oxidized and converted to formyl group. A formyl group is readily converted to a disubstituted aminomethyl group by reductive amination with disubstituted amine. Moreover, a formyl group can be converted to a substituted or unsabstituted alkenyl group by the Wittig reaction. Reference Examples 48-50 give specific embodiments.

Compounds of Formula (III) and the activated carboxyl derivatives thereof are commercially available or can be prepared according to or with reference to known methods, for example, methods described in Reference Examples 62-68 hereinbelow. Compounds of Formula (III) wherein the phenolic hydroxy group is substituted by an acetoxy group are commercially available or can be prepared according to or with reference to known methods, or methods described in Reference Examples 80, 85 and 86 below.

Compounds of Formula (II) or (V) can be prepared by reacting lower alkyl esters ($C_{1-2}$ alkyl esters in particular) of compounds of Formula (IV) or (III) with hydrazine monohydrate according to conventional methods or the method described in Reference Example 89.

The compounds of Formula (I) or prodrugs thereof prepared according to or with reference to the aforementioned methods can be isolated and purified by conventional techniques such as chromatography, recrystallization, reprecipitation, etc. The compounds of Formula (I) or prodrugs thereof may be obtained in the form of acid addition salts or salts formed with bases depending on the type of functional groups present in the structure, selection of starting materials, reaction and treatment conditions, etc. These salts can be converted to the compounds of Formula (I) or prodrugs thereof according to conventional methods. Compounds of Formula (I) having in their structures a group that is capable of forming an acid addition salt or prodrugs thereof can be converted to acid addition salts by treatment with various acids according to conventional methods. Likewise, compounds of Formula (I) having in their structures a group that is capable of forming a salt with a base or prodrugs thereof can be converted to salts by treatment with various bases according to conventional methods.

Experiments are given below to demonstrate the effect of the compounds of the present invention to support their efficacy as glucagon receptor antagonists:

Experiment 1 Experiment for Glucagon Binding Inhibition

The preparation of membrane from mouse and rat livers was carried out according to the method described in *Bioorg. Med. Chem. Lett.* 1992, 12, 915-918 in this experiment and $^{125}$I-glucagon binding activity was measured with these membranes as glucagon receptor's samples.

Livers were removed from male SD rats (about 250 g body weight per rat) and male ddY mice (about 30 g body weight per mouse). Each liver was suspended in 20-fold volume of 50 mM Tris-HCl buffer (pH 7.2) based on the wet weight of the liver, and homogenized by a glass-Teflon homogenizer. The homogenate was centrifuged for 15 minutes at 30,000×g. The precipitation was resuspended in 20-fold volume of 50 mM Tris-HCl buffer (pH 7.2) based on the wet weight of the liver and centrifuged for 15 minutes at 30,000×g. The precipitaion thus obtained was used as a hepatic membrane sample.

Each hepatic membrane sample was suspended in 100-fold volume of 50 mM Tris-HCl buffer (pH 7.2) containing 1 mg/ml BSA (Nacalai Tesque Inc.) and 0.1 mg/ml bacitracin (Wako Pure Chemical Industries Ltd.) based on the wet weight of the liver. $^{125}$I-glucagon (Perkin Elmer Life Sciences Inc., U.S.A, final concentration: 50 pM) and a test compound were added to 0.16 ml of the suspension to give a total amount of 0.2 ml. The mixture was incubated at 25° C. for 30 minutes.

$^{125}$I-glucagon bound to the membrane was recovered by suction filtration onto a GF/C filter (Whatman International Ltd., Great Britain) pretreated with 0.1% polyethyleneimine (Nacalai Tesque Inc.). The filter was washed 3 times with 50 mM Tris-HCl buffer (pH 7.2), and the radioactivity of the filter was measured by a γ counter (ARC-360, Aloka Co., Ltd.). The amount of specific binding was measured by subtracting the amount of nonspecific binding determined in the presence of 1 μM glucagon (Peptide Institute Inc.) from the total amount of binding. Each experiment was carried out in duplicate.

The amount of binding in the absence of test compound was regarded as 100%, and inhibitions (%) at various concentrations of test compounds were calculated. The concentration at 50% inhibition of binding ($IC_{50}$) was calculated using a pseudo Hill plot. The results are shown in Table 3.

TABLE 3

Glucagon binding inhibitory activity

| Test compound | $IC_{50}$ (nM) Mouse | Rat | Test compound | $IC_{50}$ (nM) Mouse | Rat |
|---|---|---|---|---|---|
| Example 1 | 99 | 21 | Example 2 | 140 | 330 |
| Example 3 | 52 | 30 | Example 4 | 130 | 28 |
| Example 5 | 130 | 200 | Example 8 | 310 | 170 |
| Example 9 | 75 | 210 | Example 10 | 230 | 180 |
| Example 11 | 450 | 140 | Example 12 | 170 | 85 |
| Example 13 | 180 | 190 | Example 15 | 170 | 27 |
| Example 16 | 180 | 87 | Example 17 | 160 | 99 |
| Example 18 | 120 | 41 | Example 19 | 97 | 86 |
| Example 20 | 24 | 9.2 | Example 43 | 390 | 160 |
| Example 45 | 120 | 220 | Example 53 | 240 | 75 |
| Example 54 | 380 | 150 | Example 56 | 220 | 150 |
| Example 59 | 84 | 35 | Example 60 | 160 | 120 |
| Example 61 | 200 | 58 | Example 98 | 4.0 | 1.5 |
| Example 99 | 13 | 3.4 | Example 100 | 9.1 | 5.8 |
| Example 101 | 28 | 33 | Example 102 | 93 | 95 |
| Example 107 | 360 | 140 | Example 108 | 310 | 110 |
| Example 113 | 43 | 28 | Example 115 | 80 | 54 |
| Example 119 | 9.6 | 16 | Example 120 | 27 | 37 |
| Example 123 | 65 | 33 | Example 126 | 15 | 14 |
| Example 127 | 7.8 | 8.6 | Example 128 | 2.8 | 3.4 |
| Example 129 | 6.1 | 5.2 | Example 136 | 48 | 96 |
| Example 138 | 23 | 15 | Example 142 | 9.3 | 5.5 |
| Example 143 | 56 | 89 | Example 145 | 190 | 100 |
| Example 146 | 38 | 27 | Example 150 | 73 | 90 |
| Example 152 | 250 | 120 | Example 153 | 18 | 24 |
| Example 156 | 45 | 44 | Example 158 | 7.1 | 5.9 |
| Example 159 | 60 | 31 | Example 160 | 3.4 | 2.9 |
| Example 162 | 8.6 | 9.6 | Example 164 | 6.5 | 3.9 |
| Example 176 | 5.2 | 6.4 | Example 179 | 28 | 63 |
| Example 180 | 46 | 84 | Example 181 | 62 | 30 |
| Example 182 | 50 | 49 | Example 183 | 34 | 51 |
| Example 184 | 59 | 18 | Example 185 | 23 | 20 |
| Example 189 | 3.0 | 5.5 | Example 190 | 110 | 110 |
| Example 196 | 63 | 40 | Example 197 | 56 | 37 |
| Example 198 | 20 | 75 | Example 199 | 75 | 99 |
| Example 161 | 140 | 100 | Example 223 | 26 | 12 |
| Example 188 | 28 | 26 | Example 224 | 48 | 27 |
| Example 193 | 350 | 330 | Example 225 | 68 | 11 |
| Example 203 | 7.7 | 7.9 | Example 226 | 31 | 21 |
| Example 204 | 5.4 | 3.6 | Example 227 | 55 | 24 |
| Example 207 | 9.5 | 8.0 | Example 229 | 58 | 28 |
| Example 208 | 270 | 290 | Example 230 | 120 | 33 |
| Example 209 | 35 | 20 | Example 232 | 34 | 38 |
| Example 210 | 7.9 | 3.9 | Example 234 | 56 | 39 |
| Example 211 | 25 | 8.5 | Example 235 | 18 | 49 |
| Example 212 | 20 | 15 | Example 238 | 210 | 160 |
| Example 213 | 80 | 35 | Example 240 | 180 | 300 |
| Example 214 | 39 | 49 | Example 242 | 180 | 89 |
| Example 217 | 37 | 60 | Example 243 | 290 | 380 |
| Example 218 | 56 | 95 | Example 245 | 64 | 29 |
| Example 222 | 42 | 25 | | | |

As is clear from Table 3, compounds of the present invention exhibit strong binding inhibitory activity on mouse and rat glucagon receptors. Accordingly, the inventors then verified that a number of compounds listed in Table 3 exhibit a strong inhibitory activity in the experiment for glucagon binding inhibition using membrane samples prepared from human normal hepatic cells.

Experiment 2 Inhibitory Effect on the Blood Sugar Increase Caused by Glucagon Stimulation in Rats This experiment was carried out according to the method described in *J. Med. Chem.* 2001, 44 (19), 3141-3149.

5-16 Male SD rats (body weight at the time of testing: 200-250 g) were used per group in this experiment. Each test compound was suspended in 0.5% tragacanth and orally administered into the animals in a specific amount. Glucagon (Peptide Institute Inc.) was intravenously administered 30 minutes later in a dose of 3.0 μg/kg, and 10 minutes later blood was collected from the tails of the rats. The blood thus collected was centrifuged, and the glucose concentration in the plasma was measured according to the glucose oxidase method. The test animals were purchased from Charles River Japan Inc., and were allowed to eat feed (standard forage CE-2; CLEA-Japan Inc.) and drink water at will until the test morning.

A number of compounds listed in Table 3 significantly suppressed the blood sugar increase caused by glucagon stimulation at a dose of 10-100 mg/kg.

Experiment 3 Blood Sugar Decreasing Action to GK (Goto-Kakizaki) Rats

Male GK rats (9-11 weeks old) having a blood sugar level of at least 160 mg/dl were used in this experiment. GK rats herein are established as type II diabetes model rats. Within 3 days of the beginning of the experiment, the rats used in this experiment were divided into groups with 9 rats per group to balance the blood sugar levels. A specific amount of a test compound suspended in 0.5% CMC was orally administered into the rats, and 4 hours later blood was collected from the tails of the rats. The blood thus collected was centrifuged, and the glucose concentration in the plasma was measured according to the glucose oxidase method. The test animals were purchased from Charles River Japan Inc., and were allowed to eat feed (standard forage CE-2; CLEA-Japan Inc.) and drink water at will until the test morning.

A number of compounds listed in Table 3 significantly decreased the blood sugar levels at a dose of 3-100 mg/kg.

As is clear from the results of the above experiment, the compounds of Formula (I), and prodrugs, physiologically acceptable salts, hydrates and solvates thereof (hereinafter sometimes referred to as "compounds of the present invention") exhibit a potent antagonistic activity on glucagon receptor with low toxicity. Therefore, they can be used as preventive and/or therapeutic agents for symptoms and diseases in which glucagon is involved. Specifically, they can be suitably employed in the prevention and/or treatment of hyperglycemia, abnormal glucose tolerance, insulin resistance syndrome, syndrome X, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, diabetic complications (cataract, retinopathy, keratopathy, neuropathy, nephropathy, etc.) and like symptoms and diseases.

Although the compounds of the present invention can be administered orally, parenterally or rectally, oral administration is preferable. Dosage of the compounds of the present invention varies according to the type of the compounds, administration method, symptoms, age of a patient, and other factors. It is usually 0.1-100 mg/kg/day, and preferably 0.5-50 mg/kg/day, in a single dose or divided doses.

The compounds of the present invention are suitably used as glucagon receptor antagonists in the form of pharmaceutical compositions prepared with pharmaceutical carriers.

Specific examples of pharmaceutical compositions include tablets, capsules, granules, powders, syrups, injections, patches, suppositories, etc. Such pharmaceutical compositions can be prepared according to conventional methods.

The pharmaceutical acceptable carriers may be any conventional ones in the medical field and do not react with the compound of the present invention. Specific examples of pharmaceutically acceptable carriers usable in the preparation of tablets, capsules, granules and powders are excipients such as lactose, corn starch, saccharose, mannitol, calcium sulfate and crystalline cellulose; disintegrators such as carmellose sodium, modified starch and carmellose calcium; binders such as methylcellulose, gelatin, gum arabic, ethylcellulose, hydroxypropylcellulose and polyvinyl pyrrolidone; and lubricants such as light anhydrous silicic acid, magnesium stearate, talc and hydrogenated oil. Tablets may be coated according to conventional methods with coating agents such as carnauba wax, hydroxypropylmethyl cellulose, macrogol, hydroxypropylmethyl phthalate, cellulose acetate phthalate, saccharose, titanium oxide, sorbitan fatty acid esters, calcium phosphate and the like.

Specific examples of carriers for use in the preparation of syrups are sweeteners such as saccharose, glucose and fructose; suspending agents such as gum arabic, tragacanth, carmellose sodium, methylcellulose, sodium alginate, crystalline cellulose and veegum; and dispersants such as sorbitan fatty acid esters, sodium lauryl sulfate and polysorbate 80. In syrup preparation, corrigent, aromatic, preservatives, etc., can be added, if necessary. Syrups may be in the form of dry syrups, to be dissolved or suspended when used.

Specific examples of bases for suppositories include cacao butter, saturated fatty acid glycerol ester, glycerogelatin and macrogol. Surfactants, preservatives, etc., can be used in the preparation of suppositories, if necessary.

Such pharmaceutical compositions usually contain as an active ingredient a compound of Formula (I) or prodrugs, physiologically acceptable salts, hydrates or solvates thereof in a proportion of 0.5% or greater, and preferably 10 to 70%. Moreover, they may contain other therapeutically effective substances as described below.

According to the symptoms of a patient, pharmaceutical compositions comprising compounds of the present invention can be administered in conjunction with various pharmaceuticals that are typically used in the prevention or treatment of type II diabetes. Specific examples of such pharmaceuticals are sulfonylureas (e.g., glibenclamide, gliclazide, glimepiride, glyclopyramide, chlorpropamide, tolbutamide, acetohexamide and tolazamide), biguanides (e.g., metformin hydrochloride and buformin hydrochloride), α-glucosidase inhibitors (e.g., acarbose, voglibose and miglitol), fast-acting insulin secretagogues (e.g., nateglinide, repaglinide and mitiglinid), aldose reductase inhibitors (e.g., epalrestat), insulin, insulin analogs, anti-obesity drugs (e.g., sibutramine hydrochloride) and lipase inhibitors (e.g., orlistat).

BEST MODE FOR CARRYING OUT THE INVENTION

The present invention is illustrated in more detail by Reference Examples and Examples but is not limited to these examples. The identification of compounds is carried out by elemental analysis, mass spectroscopy, IR spectroscopy, NMR spectroscopy, HPLC (high performance liquid chromatography), etc. The conditions for HPLC analysis included: column [Capcell Pak C18 SG 120 (manufactured by Shiseido Co., Ltd,) 4.6ϕ×150 mm], temperature of 30° C., flow rate of 1 ml/min, eluent: acetonitrile/0.05% aqueous trifluoroacetic acid solution=45/55, and UV detection(254 nm).

The following abbreviations may be used in the Reference Examples and Examples in order to simplify the description:

BOP reagent: benzotriazole-1-yloxytris(dimethylamino) phosphonium hexafluorophosphate,
DMF: dimethylformamide,
PyBOP reagent: benzotriazole-1-yloxytrispirolysinophosphonium hexafluorophosphate,
THF: tetrahydrofuran,
WSC: 1-ethyl-3-(3-dimethylaminopropyl)carbodiimide hydrochloride.

REFERENCE EXAMPLE 1

Preparation of ethyl 3-bromo-2-furancarboxylate

WSC (17.3 g), 4-dimethylaminopyridine (1.1 g) and ethanol (5.2 ml) were added to a dichloromethane solution (100 ml) of 17.2 g 3-bromo-2-furancarboxylic acid and stirred for 5 hours at 25° C. The reaction solution was washed with saturated brine and dried over MgSO$_4$. The solvent was evaporated under reduced pressure, and the residue was purified by silica gel column chromatography (eluent: ethyl acetate/hexane=1/30), thereby giving 17.5 g of the desired compound.

The starting compound, i.e., 3-bromo-2-furancarboxylic acid, was prepared according to the method described in *Bull. Soc. Chim.* 1970, 1838-1846 and *J. Chem. Soc., Perkin Trans. II* 1998, 679-689.

REFERENCE EXAMPLE 2

Preparation of 3-(3-hydroxyphenyl)-2-furancarboxylic acid

A mixture of the compound of Reference Example 1 (1.5 g), 3-hydroxyphenylboronic acid pinacol cyclic ester (2.4 g), tetrakis(triphenylphosphine)palladium (0.8 g) and cesium carbonate (3.5 g) were heated at reflux in a mixed solvent of THF (20 ml) and water (10 ml) for 16 hours under an argon atmosphere. After cooling, toluene was added to the reaction solution, and extracted with a 5% aqueous sodium hydroxide solution. The aqueous layer was acidified with concentrated hydrochloric acid and extracted with ethyl acetate. The organic layer was successively washed with water and saturated brine, and the solvent was evaporated under reduced pressure, thereby giving 1.4 g of the desired compound (1.4 g).

REFERENCE EXAMPLE 3

Preparation of 3-[3-(2,3,5,6-tetramethylbenzyloxy)phenyl]-2-furancarboxylic acid 2,3,5,6-tetramethylbenzyl ester To a solution of the compound of Reference Example 2 in DMF (35 ml) was added sodium hydride (60%, 0.37 g), and the mixture was stirred for 30 minutes at 60° C. Potassium iodide (60 mg) and 2,3,5,6-tetramethylbenzyl chloride (1.7 g) were further added and the mixture was stirred for 16 hours at the same temperature. The reaction solution was poured into ice water and extracted with ethyl acetate. The organic phase was successively washed with water and saturated brine. The solvent was evaporated under reduced pressure, thereby giving 0.9 g of the desired compound.

$^1$H-NMR (DMSO-d$_6$, δ): 2.19 (s, 6H), 2.21 (s, 6H), 2.27 (s, 12H), 5.07 (s, 2H), 5.42 (s, 2H), 6.60 (d, J=1.8 Hz, 1H), 6.95 (s, 1H), 6.95-7.05 (m, 2H), 7.20-7.35 (m, 2H), 7.52 (d, J=1.8 Hz, 1H)

REFERENCE EXAMPLE 4

Preparation of 3-[3-(2,3,5,6-tetramethylbenzyloxy)phenyl]-2-furancarboxylic acid hydrazide Hydrazine monohydrate (1.94 ml) was added to an ethanol (15 ml)/dioxane (3 ml) mixed solution of 0.5 g of the compound of Reference Example 3, and heated at reflux for 4 hours. The reaction solution was concentrated under reduced pressure, water was added to the residue, and the resultant crystals were filtered, thereby giving 0.5 g of the desired compound.

REFERENCE EXAMPLE 5

Preparation of ethyl 3-(2-hydroxyphenyl)-2-furancarboxylate (1) A mixture of the compound of Reference Example 1 (2.20 g), 2-benzyloxyphenylboronic acid (3.40 g), tetrakis(triphenylphosphine)palladium (1.20 g) and cesium carbonate (4.90 g) in a mixed solvent of THF (30 ml) and water (15 ml) were heated at reflux overnight under an argon atmosphere. After cooling, the reaction solution was diluted with ethyl acetate, and the organic layer was dried over MgSO$_4$. The solvent was evaporated under reduced pressure, and the residue was purified by silica gel column chromatography (eluent: ethyl acetate/hexane=1/20), thereby giving 3.40 g of ethyl 3-(2-benzyloxyphenyl)-2-furancarboxylate.

(2) To a dioxane (60 ml) solution of 2.30 g of the 3-(2-benzyloxyphenyl) compound obtained above, was added 5% palladium carbon. The mixture was hydrogenated at 45° C. while stirring. Once the calculated amount of hydrogen has been consumed, the catalyst was filtered off, and the filtrate was concentrated under reduced pressure, thereby giving 1.60 g of the desired compound.

REFERENCE EXAMPLE 6

Preparation of 3-[2-(2,3,5,6-tetramethylbenzyloxy)phenyl]-2-furancarboxylic acid hydrazide Sodium hydride (60%, 0.39 g) was added to a DMF (35 ml) solution of 0.7 g of the compound of Reference Example 5, and stirred for 30 minutes at 60° C. Potassium iodide (60 mg) and 2,3,5,6-tetramethylbenzyl chloride (1.8 g) were further added and stirred for 16 hours at the same temperature. The reaction solution was treated in the same manner as in Reference Example 3, thereby giving a reaction product (0.8 g). This reaction product was dissolved in ethanol (10 ml), mixed with hydrazine monohydrate (3.3 ml), and heated at reflux for 5 hours. Water was added to the reaction solution, and the precipitated crystals were filtered, thereby giving 0.5 g of the desired compound.

REFERENCE EXAMPLES 7-9

Reactions and treatments were carried out in the same manner as in Reference Example 6 except that the 2,3,5,6-tetramethylbenzyl chloride used in Reference Example 6 was replaced with the appropriate bromine compounds to obtain the following compounds:

3-(2-Isopropoxyphenyl)-2-furancarboxylic acid hydrazide (Reference Example 7),
3-(2-Propoxyphenyl)-2-furancarboxylic acid hydrazide (Reference Example 8), and
3-(2-Phenethyloxyphenyl)-2-furancarboxylic acid hydrazide (Reference Example 9).

REFERENCE EXAMPLE 10

Preparation of 4-(4-methoxyphenyl)-3-phenyl-2-furancarboxylic acid hydrazide (1) A reaction and treatment was carried out in the same manner as in Reference Example 5(1) using ethyl 3,4-dibromo-2-furancarboxylate (1.0 g) and phenylboronic acid (0.45 g), thereby giving 0.45 g of a mixture composed of ethyl 4-bromo-3-phenyl-2-furancarboxylate and ethyl 3-bromo-4-phenyl-2-furancarboxylate.

The starting compound, i.e., ethyl 3,4-dibromo-2-furancarboxylate was prepared according to the method described in *Synth. Commun.* 998, 28, 1093-1096 and Reference Example 1.

(2) A reaction and treatment was carried out in the same manner as in Reference Example 5(1) using 4-methoxyphenylbronic acid (0.37 g) and the mixture (0.45 g) of ethyl 4-bromo-3-phenyl-2-furancarboxylate and ethyl 3-bromo-4-phenyl-2-furancarboxylate, thereby giving 0.3 g of ethyl 4-(4-methoxyphenyl)-3-phenyl-2-furancarboxylate.

(3) Hydrazine monohydrate (0.97 ml) was added to an ethanol solution (5 ml) of the 4-(4-methoxyphenyl) compound (0.3 g) obtained above and heated at reflux for 3 hours. After cooling, chloroform (50 ml) and water (30 ml) were added to the reaction solution, and the organic layer was separated. The solvent was evaporated under reduced pressure, thereby giving 0.33 g of the desired compound.

REFERENCE EXAMPLE 11

Preparation of 3-phenyl-4-(4-pyridyl)-2-furancarboxylic acid hydrazide (1) A reaction and treatment was carried out in the same manner as in Reference Example 5(1) using 4-pyridylboronic acid (0.94 g) and a mixture (0.7 g) of ethyl 4-bromo-3-phenyl-2-furancarboxylate and ethyl 3-bromo-4-phenyl-2-furancarboxylate as obtained by carring out a reaction and treatment in the same manner as in Reference Example 10(1). The product thus obtained was recrystallized from acetonitrile, giving 0.4 g of ethyl 3-phenyl-4-(4-pyridyl)-2-furancarboxylate.

(2) Hydrazine monohydrate (1.36 ml) was added to an ethanol solution (10 ml) of the 4-(4-pyridyl) compound and refluxed for 3 hours under heating. After evaporating the reaction solution under reduced pressure, water was added to the residue, and the thus-precipitated crystals were filtered, thereby giving 0.3 g of the desired compound.

REFERENCE EXAMPLE 12

Preparation of 3-(2-furyl)-2-furancarboxylic acid (1) A reaction and treatment was carried out in the same manner as in Reference Example 5(1) using the compound of Reference Example 1 (0.66 g) and 2-furylboronic acid (0.67 g), thereby giving 0.38 g of ethyl 3-(2-furyl)-2-furancarboxylate.

(2) An aqueous solution (2.76 ml) of 1 M sodium hydroxide was added to an ethanol solution (5 ml) of the 3-(2-furyl) compound and heated at reflux for 2 hours while stirring. After evaporating the solvent under reduced pressure, 1 M hydrochloric acid was added, and the thus-precipitated crystals were filtered, thereby giving 0.30 g of the desired compound.

REFERENCE EXAMPLE 13

Preparation of 3-(2-thienyl)-2-furancarboxylic acid hydrazide

A reaction and treatment was carried out in the same manner as in Reference Example 5(1) using the compound of Reference Example 1 (0.88 g) and 2-thienylboronic acid (1.02 g), thereby giving 0.91 g of ethyl 3-(2-thienyl)-2-furancarboxylate. This compound (0.88 g) was reacted with hydrazine monohydrate in the same manner as in Reference Example 10(3), thereby giving 0.62 of the desired compound.

REFERENCE EXAMPLE 14

Preparation of 3-phenyl-2-furancarboxylic acid hydrazide

A reaction and treatment was carried out in the same manner as in Reference Example 5(1) using the compound of Reference Example 1 (1.40 g) and phenylboronic acid (1.56 g), thereby giving 1.12 g of ethyl 3-phenyl-2-furancarboxylate. This compound (1.10 g) was reacted with hydrazine monohydrate in the same manner as in Reference Example 10(3), thereby giving 1.20 g of the desired compound.

$^1$H-NMR (DMSO-$d_6$, δ): 6.96 (d, J=1.5 Hz, 1H), 7.11 (d, J=8.8 Hz, 1H), 7.29-7.42 (m, 3H), 7.73 (d, J=6.8 Hz, 2H), 7.95 (d, J=1.5 Hz, 1H), 8.02 (dd, J=2.0, 8.8 Hz, 1H), 8.15 (d, J=2.0 Hz, 1H), 10.36 (s, 2H), 11.88 (br s, 1H)

REFERENCE EXAMPLE 15

Preparation of 3-phenoxybromobenzene

A mixture of 1,3-dibromobenzene (15.7 g), phenol (8.0 g), potassium hydroxide (3.8 g, mortar-ground) and copper powder (0.1 g) was heated at reflux for 18 hours at 210° C. After cooling, the reaction mixture was mixed with toluene and successively washed with 10% aqueous sodium hydroxide and water. The toluene was evaporated under reduced pressure. The residue was purified by silica gel column chromatography (eluent: hexane), thereby giving 6.1 g of the desired compound.

REFERENCE EXAMPLE 16

Preparation of 3-phenoxyphenylboronic acid

Under an argon atmosphere, butyl lithium (1.56 M, hexane solution: 16 ml) was added at −78° C. to an anhydrous THF solution (40 ml) of the compound of Reference Example 15 (6.0 g) and stirred at this temperature for 30 minutes. Boric acid triisopropyl ester (4.7 g) was added. The mixture was stirred at −78° C. for 30 minutes, and after raising the temperature to 25° C., the mixture was further stirred for 30 minutes. To the reaction solution, was then added 1 M hydrochloric acid (30 ml), and after 30 minutes of stirring at 25° C., the organic layer was separated and washed with saturated brine. The solvent was then evaporated under reduced pressure, thereby giving 4.6 g of the desired product.

REFERENCE EXAMPLE 17

Preparation of ethyl 3-(3-phenoxyphenyl)-2-furancarboxylate

Under an argon atmosphere, a mixture of the compound of Reference Example 1 (1.0 g), the compound of Reference Example 16 (2.0 g), tetrakis(triphenylphosphine) palladium (0.5 g) and cesium carbonate (3.0 g) was heated at reflux for 16 hours in a mixed solvent of THF (15 ml) and water (7 ml). After cooling, the reaction solution was diluted with water (30 ml) and extracted with ethyl acetate. The organic layer was successively washed with water and saturated brine. The residue was purified by silica gel column chromatography (eluent: ethyl acetate/hexane=1/15), thereby giving 1.3 g of the desired compound.

REFERENCE EXAMPLE 18

Preparation of 3-(3-phenoxyphenyl)-2-furancarboxylic acid hydrazide

Hydrazine monohydrate (2.0 ml) was added to an ethanol solution (2 ml) of the compound of Reference Example 17 (1.3 g), and heated at reflux for 5 hours. The reaction solution was diluted with water and extracted with chloroform. The chloroform layer was washed with water and concentrated under reduced pressure, thereby giving 1.4 g of the desired compound.

REFERENCE EXAMPLE 19

Preparation of 3-(2-phenoxyphenyl)-2-furancarboxylic acid hydrazide

A reaction and treatment was carried out in the same manner as in Reference Example 15 except that 1,3-dibromobenzene used in Reference Example 15 was replaced with 1,2-dibromobenzene, thereby giving 2-phenoxy bromobenzene. Using this compound, reactions and treatments were carried out in the same manner as in Reference Examples 16, 17 and 18, thereby giving the desired compound.

REFERENCE EXAMPLES 20 AND 21

Reactions and treatments were carried out in the same manner as in Reference Example 3 except that the 2,3,5,6-tetramethylbenzyl chloride used in Reference Example 3 was replaced with benzylbromide and phenethylbromide, respectively, thereby giving the 3-(3-benzyloxy)-2-furancarboxylic acid ester and the 3-(3-phenethyloxyphenyl)-2-furancarboxylic acid ester. Using these compounds, reactions and treatments were carried out in the same manner as in Reference Example 10(3), thereby giving the desired compounds: 3-(3-Benzyloxyphenyl)-2-furancarboxylic acid hydrazide (Reference Example 20),
3-(3-Phenethyloxyphenyl)-2-furancarboxylic acid hydrazide (Reference Example 21).

REFERENCE EXAMPLE 22

Preparation of 3-(2-benzyloxyphenyl)-2-furancarboxylic acid hydrazide

A reaction and treatment was carried out in the same manner as in Reference Example 18 except that the compound of Reference Example 17 used in Reference Example 18 was replaced with the compound of Reference Example 5(1), thereby giving the desired compound.

REFERENCE EXAMPLE 23

Preparation of 3-(2-biphenylyl)-2-furancarboxylic acid hydrazide

A reaction and treatment was carried out in the same manner as in Reference Example 17 except that the 3-phenoxyphenylboronic acid used in Reference Example 17 was replaced with 2-biphenylylboronic acid, thereby giving ethyl 3-(2-biphenylyl)-2-furancarboxylate. Using this compound, a reaction and treatment was conducted in the same manner as in Reference Example 11(2), thereby giving the desired compound.

REFERENCE EXAMPLE 24

Preparation of ethyl 3-(2-trifluoromethylsulfonyloxy)-2-furancarboxylate

Under an argon atmosphere, trifluoromethanesulfonic acid anhydride (1.2 ml) was added dropwise to pyridine (20 ml) solution of the compound of Reference Example 5 (1.3 g) while stirring under ice-cooling, and then stirred for 16 hours at 25° C. The reaction solution was poured into water and extracted with diethyl ether. The diethyl ether layer was successively washed with 1 M hydrochloric acid and saturated brine, and then concentrated under reduced pressure, thereby giving a crude product. This crude product was purified by silica gel column chromatography (eluent: ethyl acetate/hexane=1/20), thereby giving 1.0 g of the desired compound.

REFERENCE EXAMPLE 25

Preparation of 3-(2-benzylphenyl)-2-furancarboxylic acid hydrazide

Under an argon atmosphere, benzyl zinc bromide (0.5 M THF solution; 28 ml) was added dropwise at 25° C. to an anhydrous THF (20 ml) solution of the compound of Reference Example 24 (1.0 g) and tetrakis(triphenylphosphine) palladium (0.4 g), and stirred while heating for 34 hours. The reaction solution was concentrated under reduced pressure, and the residue was diluted with 5% hydrochloric acid and extracted with ethyl acetate. The organic layer was successively washed with water and saturated brine, and the solvent was evaporated under reduced pressure, thereby giving a crude product. This crude product was purified by silica gel column chromatography (eluent: ethyl acetate/hexane=1/20), thereby giving 0.65 g of ethyl 3-(2-benzylphenyl)-2-furancarboxylate.

Using this compound, a reaction and treatment was carried out in the same manner as in Reference Example 11(2), thereby giving the desired compound.

REFERENCE EXAMPLE 26

Preparation of 3-(2-hydroxyphenyl)-2-furancarboxylic acid hydrazide

A reaction and treatment was carried out in the same manner as in Reference Example 11(2) except that the compound of Reference Example 3 used in Reference Example 4 was replaced with the compound of Reference Example 5, thereby giving the desired compound.

REFERENCE EXAMPLE 27

Preparation of 3-(2-cyclohexylmethyloxyphenyl)-2-furancarboxylic acid hydrazide

A reaction and treatment was carried out in the same manner as in Reference Example 6 except that the 2,3,5,6-tetramethylbenzyl chloride used in Reference Example 6 was replaced with cyclohexylmethyl bromide, thereby giving the desired compound.

REFERENCE EXAMPLE 28

Preparation of 4-(2,3,5,6-tetramethylbenzyloxy)bromobenzene

In acetone (50 ml), a mixture of 4-bromophenol (7.8 g), 2,3,5,6-tetramethylbenzyl chloride (6.3 g) and potassium carbonate (6.5 g) was heated at reflux for 16 hours. The reaction solution was filtered, and the filtrate was concentrated under reduced pressure. The residue was dissolved in ethyl acetate, and successively washed with 3% aqueous sodium hydroxide solution, water and saturated brine. The solvent was evaporated under reduced pressure, thereby giving 8.7 g of the desired compound.

REFERENCE EXAMPLE 29

Preparation of 4-(2,3,5,6-tetramethylbenzyloxy)phenylboronic acid

A reaction and treatment was carried out in the same manner as in Reference Example 16 except that the compound of Reference Example 15 used in Reference Example 16 was replaced with the compound of Reference Example 28 (3.0 g), thereby giving 1.7 g of the desired compound.

REFERENCE EXAMPLE 30

Preparation of ethyl 3-[4-(2,3,5,6-tetramethylbenzyloxy)phenyl]-2-furancarboxylate Under an argon atmosphere, a mixture of the compound of Reference Example 29 (1.4 g), the compound of Reference Example 1 (0.7 g), tetrakis(triphenylphosphine)palladium (0.4 g) and cesium carbonate (1.6 g) was heated at reflux for 16 hours in a mixed solvent of THF (10 ml) and water (5 ml). After cooling, the reaction solution was diluted with water and extracted with ethyl acetate. The organic layer was successively washed with water and saturated brine, and concentrated under reduced pressure, thereby giving a crude compound. This crude compound was purified by silica gel column chromatography (eluent: ethyl acetate/hexane=1/15), thereby giving 1.0 g of the desired compound.

REFERENCE EXAMPLE 31

Preparation of 3-[4-(2,3,5,6-tetramethylbenzyloxy)phenyl]-2-furancarboxylic acid hydrazide Hydrazine monohydrate (2.6 g) was added to an ethanol (40 ml) solution of 1.0 g of the compound of Reference Example 30, and heated at reflux for 16 hours. The reaction solution was cooled, and the thus-precipitated crystals were filtered, washed with water and dried, thereby giving 0.9 g of the desired product.

REFERENCE EXAMPLE 32

Preparation of 3,4-diphenyl-2-furancarboxylic acid hydrazide

Ethanol (50 ml) was added to a mixture of methyl 3,4-diphenyl-2-furancarboxylate (14.00 g) and hydrazine monohydrate (7.33 ml), and heated at reflux while stirring overnight. After concentrating the reaction solution under reduced pressure and adding ethanol, the thus-precipitated crystals were filtered, thereby giving 13.80 g of the desired compound.

The starting compound, i.e., methyl 3,4-diphenyl-2-furancarboxylate, was prepared according to the method described in *Journal of the Pharmaceutical Society of Japan* 1974, 94, 1312-1321.

REFERENCE EXAMPLE 33

Preparation of 3,4-diphenyl-2-furancarboxylic acid

Methyl 3,4-diphenyl-2-furancarboxylate (10.00 g) and sodium hydroxide (1.73 g) in a mixed solution of ethanol (20 ml) and water (20 ml) were heated at reflux for 3 hours while stirring. After evaporating the solvent under reduced pressure, 1 M hydrochloric acid was added, and the thus-precipitated crystals were filtered, thereby giving 5.20 g of the desired compound.

REFERENCE EXAMPLE 34 AND 35

Reactions and treatments were carried out in the same manner as in Reference Example 33 except that methyl 3,4-diphenyl-2-furancarboxylate used in Reference Example 33 was replaced with the corresponding methyl ester compounds (prepared according to the method described in *Journal of the Pharmaceutical Society of Japan* 1974, 94, 1312-1321), thereby giving the following compounds:

3,4-Bis(4-methoxyphenyl)-2-furancarboxylic acid (Reference Example 34), and 3,4-Bis(4-methylphenyl)-2-furancarboxylic acid (Reference Example 35).

REFERENCE EXAMPLE 36

Preparation of 3,4-bis(4-chlorophenyl)-2-furancarboxylic acid hydrazide (1) In acetonitrile (10 ml), a mixture of 4-chlorophenylacetic acid (1.70 g), 4-chlorophenacyl bromide (2.33 g) and potassium carbonate (5.53 g) was heated at reflux while stirring for 2 hours. Toluene and water were added to the reaction mixture, and the thus-precipitated crystals were filtered and purified by silica gel column chromatography (eluent: ethyl acetate/hexane=1/5), thereby giving 1.37 g of 3,4-bis(4-chlorophenyl)-2(5H)-furanone.

(2) Diisobutyl aluminium hydride (1.0 M hexane solution: 5.4 ml) was added dropwise to a dichloromethane (10 ml) solution of the aforementioned furanone compound (1.70 g) at −78° C. After raising the temperature to 25° C., concentrated sulfuric acid (0.1 ml) was added and the mixture was stirred for 3 hours. The reaction solution was mixed with water, extracted with ethyl acetate, and dried over $MgSO_4$. The solvent was evaporated under reduced pressure. The residue was purified by silica gel column chromatography (eluent: ethyl acetate/hexane=1/20), thereby giving 1.00 g of 3,4-bis(4-chlorophenyl)furan.

(3) Butyllithium (1.60 M hexane solution: 2.37 ml) was added dropwise to a THF (10 ml) solution of diisopropylamine (0.54 ml) at 0° C. The aforementioned furan compound (1.00 g) in THF (10 ml) solution was further added dropwise thereto at −78° C., and the mixture was stirred for 30 minutes at −78° C. After introducing dry ice into the reaction solution and raising the temperature to 25° C., diethyl ether and 2 M hydrochloric acid were added. The organic layer was dried over $MgSO_4$, and the solvent was evaporated under reduced pressure. The residue was crystallized, thereby giving 0.80 g of 3,4-bis(4-chlorophenyl)-2-furancarboxylic acid.

(4) WSC (0.69 g) and 4-dimethylaminopyridine (0.03 g) were added to a methanol (10 ml) solution of the aforementioned carboxylic acid compound (0.80 g), and stirred overnight at 25° C. After evaporating the solvent under reduced pressure, ethyl acetate and water were added to the residue, and the organic layer was dried over $MgSO_4$. The solvent was evaporated under reduced pressure, and the residue was purified by silica gel column chromatography (eluent: ethyl acetate/hexane=1/10), thereby giving 0.60 g of methyl 3,4-bis(4-chlorophenyl)-2-furancarboxylate.

(5) This ester compound (0.38 g) was reacted with hydrazine monohydrate in the same manner as in Reference Example 31, thereby giving 0.15 g of the desired compound.

REFERENCE EXAMPLES 37 AND 38

Reactions and treatments were carried out in the same manner as in Reference Example 36 except that the 4-chlorophenylacetic acid used in Reference Example 36(1) was replaced with the appropriate phenylacetic acid derivatives to give the following compounds:
3,4-Bis(4-fluorophenyl)-2-furancarboxylic acid hydrazide (Reference Example 37), and
3,4-Bis(4-bromophenyl)-2-furancarboxylic acid hydrazide (Reference Example 38).

REFERENCE EXAMPLE 39

Preparation of 4-phenyl-3-vinyl-2-furancarboxylic acid hydrazide and
3-phenyl-4-vinyl-2-furancarboxylic acid hydrazide Butyllithium (1.60 M hexane solution; 7.00 ml) was added dropwise to a THF (6 ml) solution of diisopropylamine (1.56 ml) at 0° C. A THF (6 ml) solution of 3-phenyl-4-vinylfuran (1.90 g) was further added dropwise thereto at −78° C., and the mixture was stirred at this temperature for 1 hour. After introducing dry ice into the reaction solution and raising the temperature to 25° C., the reaction solution was diluted with diethyl ether and neutralized with 2 M hydrochloric acid. The organic layer was dried over $MgSO_4$, and the solvent was evaporated under reduced pressure.

After adding methanol (20 ml) to the residue, WSC (4.80 g) and 4-dimethylaminopyridine (0.09 g) were added and stirred at 25° C. for 0.5 hours. The solvent was evaporated under reduced pressure, and ethyl acetate and water were added. The organic layer was dried over $MgSO_4$. The solvent was evaporated under reduced pressure, and the residue was purified by silica gel column chromatography (eluent: ethyl acetate/hexane=1/30), thereby giving 0.72 g of methyl 4-phenyl-3-vinyl-2-furancarboxylate and 0.40 g of methyl 3-phenyl-4-vinyl-2-furancarboxylate.

The 4-phenyl compound (0.70 g) and 3-phenyl compound (0.40 g) were respectively reacted with hydrazine monohydrate in the same manner as in Reference Example 31, thereby giving 0.34 g of 4-phenyl-3-vinyl-2-furancarboxylic acid hydrazide and 0.20 g of 3-phenyl-4-vinyl-2-furancarboxylic acid hydrazide.

The starting compound, i.e., 3-phenyl-4-vinylfuran, was prepared from 3-phenyl-2-propyne-1-ol and vinylmagnesium chloride according to the method described in *Tetrahedron Lett.* 2000, 41, 17-20.

REFERENCE EXAMPLE 40

Preparation of 3-ethyl-4-phenyl-2-furancarboxylic acid hydrazide

An ethanol (10 ml) solution of methyl 4-phenyl-3-vinyl-2-furancarboxylate (0.20 g) was blended with 10% palladium carbon and hydrogenated for 3 hours at 25° C. while stirring. The catalyst was filtered off, and the filtrate was concentrated under reduced pressure, thereby giving 0.20 g of methyl 3-ethyl-4-phenyl-2-furancarboxylate. This compound was reacted with hydrazine monohydrate in the same manner as in Reference Example 31, thereby giving 0.12 g of the desired compound.

REFERENCE EXAMPLE 41

Preparation of 4-ethyl-3-phenyl-2-furancarboxylic acid hydrazide

A reaction and treatment was carried out in the same manner as in Reference Example 40 except that the methyl 4-phenyl-3-vinyl-2-furancarboxylate used in Reference Example 40 was replaced with methyl 3-phenyl-4-vinyl-2-furancarboxylate, thereby giving the desired compound.

REFERENCE EXAMPLE 42

Preparation of 3-(tert-butyldimethylsilyloxymethyl)-4-phenyl-2-furancarboxylic acid hydrazide and 4-(tert-butyl dimethylsilyloxymethyl)-3-phenyl-2-furancarboxylic acid hydrazide Butyllithium (1.60 M hexane solution: 40.00 ml) was added dropwise to a THF (10 ml) solution of 3-(tert-butyldimethylsilyloxymethyl)-4-phenylfuran (15.40 g) and tetramethylenediamine (9.69 ml) at −78° C., and stirred for 0.5 hours. After introducing dry ice into the reaction solution and raising the temperature to 25° C., the reaction solution was mixed with diethyl ether and neutralized with 2 M hydrochloric acid. The organic layer was dried over $MgSO_4$, and the solvent was evaporated under reduced pressure.

After adding methanol (20 ml) to the residue, WSC (12.26 g) and 4-dimethylaminopyridine (0.23 g) were added and stirred at 25° C. for 0.5 hours. The solvent was evaporated under reduced pressure, diethyl ether and water were added, and the organic layer was dried over MgSO$_4$. The solvent was evaporated under reduced pressure, and the residue was purified by silica gel column chromatography (eluent: 0%→3% ethyl acetate/hexane gradient), thereby giving 2.20 g of methyl 3-(tert-butyldimethylsilyloxymethyl)-4-phenyl-2-furancarboxylate and 1.74 g of methyl 4-(tert-butyldimethylsilyloxymethyl)-3-phenyl-2-furancarboxylate.

The 4-phenyl compound (0.16 g) and 3-phenyl compound (0.17 g) were respectively reacted with hydrazine monohydrate in the same manner as in Reference Example 31, thereby giving 0.16 g of 3-(tert-butyldimethylsilyloxymethyl)-4-phenyl-2-furancarboxylic acid hydrazide and 0.17 g of 4-(tert-butyldimethylsilyloxymethyl)-3-phenyl-2-furancarboxylic acid hydrazide.

The starting compound, i.e., 3-(tert-butyldimethylsilyloxymethyl)-4-phenylfuran, was prepared according to the method described in *Tetrahedron Lett.*, 1991, 32, 5881-5884, and *J. Org. Chem.*, 1997, 62, 8741-8749.

REFERENCE EXAMPLE 43

Preparation of methyl 4-hydroxymethyl-3-phenyl-2-furancarboxylate

Tetrabutylammonium fluoride (1 M THF solution: 7.62 ml) was added at 25° C. to a THF (10 ml) solution of methyl 4-(tert-butyldimethylsilyloxymethyl)-3-phenyl-2-furancarboxylate (2.20 g), and stirred for 0.5 hours. Chloroform and water were added to the reaction solution, the organic layer was dried over MgSO$_4$, and the solvent was evaporated under reduced pressure. The residue was purified by silica gel column chromatography (eluent: 0%→30% ethyl acetate/hexane gradient, thereby giving 1.00 g of the desired compound.

REFERENCE EXAMPLE 44

Preparation of 3-phenyl-4-phenylaminocarbonyloxymethyl-2-furancarboxylic acid hydrazide Phenyl isocyanato (0.21 ml) and ethyldiisopropylamine (0.33 ml) were added to a dichloromethane (10 ml) solution of the compound of Reference Example 43 (0.35 g), and heated at reflux for 6 hours while stirring. The thus-precipitated crystals were filtered, thereby giving methyl 3-phenyl-4-phenylaminocarbonyloxymethyl-2-furancarboxylate.

The product was dissolved in ethanol (5 ml), mixed with hydrazine monohydrate (1.00 ml), and stirred for 4 hours at 70° C. The solvent was evaporated under reduced pressure, thereby giving the desired compound.

REFERENCE EXAMPLES 45 AND 46

Reactions and treatments were carried out in the same manner as in Reference Example 44 using the appropriate methyl 3- or 4-hydroxymethyl-2-furancarboxylate derivatives and a cyanato compound, thereby giving the following compounds:

4-Phenethylaminocarbonyloxymethyl-3-phenyl-2-furancarboxylic acid hydrazide (Reference Example 45), and 4-Phenyl-3-phenylaminocarbonyloxymethyl-2-furancarboxylic acid hydrazide (Reference Example 46).

REFERENCE EXAMPLE 47

Preparation of 4-benzyloxymethyl-3-phenyl-2-furancarboxylic acid hydrazide

Sodium hydride (60%, 0.080 g) was added to a DMF (10 ml) solution of the compound of Reference Example 43 (0.35 g) and stirred for 0.5 hours. Benzyl bromide (0.22 ml) was further added thereto and stirred for 4 hours, and then ethyl acetate and water were added. The organic layer was dried over MgSO$_4$, and the solvent was evaporated under reduced pressure. The residue was dissolved in ethanol (5 ml), mixed with hydrazine monohydrate (1.00 ml), and stirred for 4 hours at 70° C. The solvent was evaporated under reduced pressure, thereby giving 0.15 g of the desired compound.

REFERENCE EXAMPLE 48

Preparation of 3-phenyl-4-piperidinomethyl-2-furancarboxylic acid hydrazide (1) Manganese dioxide (0.25 g) was added to a chloroform (10 ml) solution of the compound of Reference Example 43 (0.33 g), and stirred overnight at 25° C. The manganese dioxide was removed by filtration, and the filtrate was purified by silica gel column chromatography (eluent: ethyl acetate/hexane=1/20), thereby giving 0.22 g of methyl 4-formyl-3-phenyl-2-furancarboxylate.

(2) After adding piperidine (0.084 g) to a methanol (10 ml) solution of the above-obtained 4-formyl compound (0.25 g) and stirring for 0.5 hours at 25° C., sodium borohydride (0.082 g) was added and stirred for 5 hours. Chloroform and water were then added to the reaction solution, the organic layer was dried over MgSO$_4$, and the solvent was evaporated under reduced pressure, thereby giving 0.18 g of methyl 3-phenyl-4-piperidinomethyl-2-furancarboxylate.

(3) The above-obtained 4-piperidinomethyl compound (0.18 g) was mixed with hydrazine monohydrate (1.00 ml), and stirred for 4 hours at 70° C. The solvent was evaporated under reduced pressure, thereby giving 0.18 g of the desired compound.

REFERENCE EXAMPLE 49

Preparation of 4-phenyl-3-piperidinomethyl-2-furancarboxylic acid hydrazide

A reaction and treatment was carried out in the same manner as in Reference Example 43 except that methyl 4-(tert-butyldimethylsilyloxymethyl)-3-phenyl-2-furancarboxylate used in Reference Example 43 was replaced with methyl 3-(tert-butyldimethylsilyloxymethyl)-4-phenyl-2-furancarboxylate, thereby giving methyl 3-hydroxymethyl-4-phenyl-2-furancarboxylate. Using this product, a reaction and treatment was carried out in the same manner as in Reference Example 48, thereby giving the desired compound.

REFERENCE EXAMPLE 50

Preparation of 3-phenyl-4-(4-phenyl-1-butenyl)-2-furancarboxylic acid hydrazide

After adding hexamethyldisilazane potassium salt (0.5 M toluene solution: 2.3 ml) to a toluene (10 ml) solution of 3-phenylpropyl triphenylphosphonium bromide (0.52 g) at 0° C. and stirring for 1 hour, methyl 4-formyl-3-phenyl-2-furancarboxylate (0.22 g) was added and heated at reflux for 4 hours while stirring. Water was added to the reaction solution, the organic layer was dried over $MgSO_4$, and the solvent was evaporated under reduced pressure. The residue was purified by silica gel column chromatography (eluent: ethyl acetate/hexane=1/10), thereby giving methyl 3-phenyl-4-(4-phenyl-1-butenyl)-2-furancarboxylate. This product was reacted with hydrazine monohydrate in the same manner as in Reference Example 10(3), thereby giving the desired compound.

REFERENCE EXAMPLE 51

Preparation of 3-furancarboxylic acid hydrazide

Ethyl 3-furancarboxylate (7.0 g) and hydrazine monohydrate (4.8 ml) in ethanol (10 ml) were heated at reflux while stirring for 6 hours. The solvent was evaporated under reduced pressure, and the thus-precipitated crystals were recrystallized from ethanol, thereby giving 3.2 g of the desire compound.

REFERENCE EXAMPLE 52

Preparation of 5-bromo-3,4-diphenyl-2-furancarboxylic acid (1) Bromine (0.18 ml) was added to a dichloromethane (10 ml) solution of methyl 3,4-diphenyl-2-furancarboxylate (1.00 g) at 0° C., and stirred at this temperature for 4 hours. The reaction solution was diluted with chloroform, and successively washed with water, saturated aqueous sodium hydrogencarbonate solution, and saturated brine. The organic layer was dried over $MgSO_4$, and the solvent was evaporated under reduced pressure, thereby giving 1.28 g of methyl 5-bromo-3,4-diphenyl-2-furancarboxylate.

(2) To an ethanol (5 ml) solution of the above-obtained 5-bromo compound (0.71 g), 1 M aqueous sodium hydroxide solution (2.00 ml) was added and the mixture was heated at reflux for 2 hours while stirring. The solvent was evaporated under reduced pressure, 1 M hydrochloric acid was added, and the thus-precipitated crystals were filtered, thereby giving 0.69 g of the desired compound.

REFERENCE EXAMPLE 53

Preparation of 5-methoxy-3,4-diphenyl-2-furancarboxylic acid

Copper iodide (0.23 g) and sodium methoxide (28% methanol solution; 2.46 ml) were added to a methanol (5 ml) solution of the compound of Reference Example 52(1) (2.23 g), and the mixture was heated at reflux while stirring overnight. After removing solid matter by filtration and concentrating the filtrate under reduced pressure, the residue was diluted with chloroform and washed with water. The organic layer was dried over $MgSO_4$, and the solvent was evaporated under reduced pressure. The residue was purified by silica gel column chromatography (eluent: ethyl acetate/hexane=1/20), thereby giving 1.40 g of methyl 5-methoxy-3,4-diphenyl-2-furancarboxylate.

Using 0.92 g of this product, a reaction and treatment was carried out in the same manner as in Reference Example 52 (2), thereby giving 0.90 g of the desired compound.

REFERENCE EXAMPLE 54

Preparation of 3,4,5-triphenyl-2-furancarboxylic acid

Using the compound of Reference Example 52(1) (1.40 g) and phenylboronic acid (2.17 g), a reaction and treatment was carried out in the same manner as in Reference Example 2, thereby giving 0.92 g of methyl 3,4,5-triphenyl-2-furancarboxylate.

Using 0.70 g of this compound, a reaction and treatment was carried out in the same manner as in Reference Example 52(2), thereby giving 0.64 g of the desired compound.

REFERENCE EXAMPLE 55

Preparation of 5-bromo-3-phenyl-2-furancarboxylic acid

Bromine (1.29 ml) was added to a dichloromethane (40 ml) solution of ethyl 3-phenyl-2-furancarboxylate (3.60 g) at 0° C. and stirred overnight at 25° C. The reaction solution was diluted with chloroform and washed with saturated aqueous sodium hydrogencarbonate solution, 20% aqueous sodium thiosulphate solution, and saturated brine. The organic layer was dried over $MgSO_4$, and the solvent was evaporated under reduced pressure, thereby giving 3.50 g of ethyl 5-bromo-3-phenyl-2-furancarboxylate.

Using 0.20 g of this product, a reaction and treatment was carried out in the same manner as in Reference Example 52 (2), thereby giving 0.15 g of the desired compound.

REFERENCE EXAMPLE 56

Preparation of 3,5-diphenyl-2-furancarboxylic acid

Using ethyl 5-bromo-3-phenyl-2-furancarboxylate (1.18 g) and phenylboronic acid (0.98 g), a reaction and treatment was carried out in the same manner as in Reference Example 2, thereby giving 1.21 g of ethyl 3,5-diphenyl-2-furancarboxylate.

Using 0.88 g of this product, a reaction and treatment was carried out in the same manner as in Reference Example 52(2), thereby giving 0.70 g of the desired compound.

REFERENCE EXAMPLE 57

Preparation of 4-bromo-2-furancarboxylic acid tert-butyl ester (1) A mixture composed of 4,5-dibromo-2-furancarboxylic acid (20.00 g), DMF di-tert-butylacetal (71.08 ml) and toluene (100 ml) was stirred for 2 hours at 90° C. The reaction solution was diluted with toluene and washed with 10% aqueous citric acid solution and saturated brine. The organic layer was dried over $MgSO_4$, and the solvent was evaporated under reduced pressure. The residue was purified by silica gel column chromatography (eluent: ethyl acetate/hexane=1/20), thereby giving 20.10 g of tert-butyl 4,5-dibromo-2-furancarboxylate.

(2) Tert-butyllithium (1.51 M pentane solution: 30.48 ml) was added dropwise to a diethyl ether (100 ml) solution of the above-obtained tert-butyl ester compound (10.00 g) at −78° C. After confirming the completion of the reaction at −78° C., the reaction solution was poured into saturated aqueous ammonium chloride solution (200 ml), diluted with diethyl ether (100 ml), and mixed with 2 M hydrochloric acid. The organic layer was dried over $MgSO_4$, and the solvent was evaporated under reduced pressure. The residue was purified by silica gel column chromatography (eluent: 0%→10% ethyl acetate/hexane gradient), thereby giving 1.81 g of the desired compound.

REFERENCE EXAMPLES 58 TO 61

Using the compound of Reference Example 57 and the appropriate phenylboronic acids, reactions and treatments were carried out in the same manner as in Reference Example 5(1), thereby giving tert-butyl 4-phenyl-2-furancarboxylate derivatives. Using these products, reactions and treatments were carried out in the same manner as in Reference Example 10(3), thereby giving the following compounds:

4-Phenyl-2-furancarboxylic acid hydrazide (Reference Example 58), 4-(2-Benzyloxyphenyl)-2-furancarboxylic acid hydrazide (Reference Example 59), 4-(3-Benzyloxyphenyl)-2-furancarboxylic acid hydrazide (Reference Example 60), and 4-(4-Benzyloxyphenyl)-2-furancarboxylic acid hydrazide (Reference Example 61).

REFERENCE EXAMPLE 62

Preparation of 3-cyano-4-hydroxybenzoic acid

A mixture of methyl 3-cyano-4-methoxybenzoate (70 g) and pyridine hydrochloride (128.3 g) was stirred for 1 hour at 180° C. in an oil bath. Ice-water (1 L) was added to the reaction mixture, and the thus-precipitated crystals were filtered and recrystallized from ethyl acetate, thereby giving 48.1 g of the desired compound.

REFERENCE EXAMPLE 63

Preparation of 3-cyano-4-hydroxybenzoic acid pentafluorophenyl ester

WSC (75.2 g) was added to a THF (500 ml) solution of the compound of Reference Example 62 (48.1 g) and pentafluorophenol (58.9 g) at 0° C., and stirred overnight at 25° C. The reaction solution was diluted with ethyl acetate, washed with water, and dried over $MgSO_4$. The solvent was evaporated under reduced pressure, and the residue was purified by silica gel column chromatography (eluent: methanol/chloroform=1/10) and recrystallized from ethyl acetate, thereby giving 32.5 g of the desired compound.
$^1$H-NMR (DMSO-$d_6$, δ): 7.23 (d, 8.8 Hz, 1H), 8.37 (dd, J=2.0, 8.8 Hz, 1H), 9.01 (d, J=2.0 Hz, 1H), 12.61 (s, 1H)

REFERENCE EXAMPLE 64

Preparation of pentafluorophenyl 4-hydroxy-3-nitrobenzoate

WSC (7.9 g) was added to a THF (100 ml) solution of 4-hydroxy-3-nitrobenzoic acid (7.3 g). and pentafluorophenol (7.4 g) at 0° C., and stirred overnight at 25° C. Water (50 ml) was added to the reaction solution, the solvent was evaporated under reduced pressure, and the organic layer was extracted with ethyl acetate. After drying the organic layer over $MgSO_4$, the solvent was evaporated under reduced pressure, and the residue was purified by silica gel column chromatography (eluent: ethyl acetate/hexane=1/4), thereby giving 7.9 g of the desired compound.
$^1$H-NMR (CDCl$_3$, δ): 7.35 (d, 8.8 Hz, 1H), 8.37 (dd, J=2.2, 8.8 Hz, 1H), 9.01 (d, J=2.2 Hz, 1H), 11.06 (br s, 1H)

REFERENCE EXAMPLE 65

Preparation of 3-(tert-butoxycarbonylamino)-4-methoxybenzoic acid hydrazide (1) A reaction and treatment was conducted in the same manner as in Reference Example 1 except that the 3-bromo-2-furancarboxylic acid and ethanol used in Reference Example 1 were replaced with 3-(tert-butoxycarbonylamino)-4-methoxybenzoic acid (5.00 g) and methanol (0.76 ml), respectively, thereby giving 5.51 g of methyl 3-(tert-butoxycarbonylamino)-4-methoxybenzoate.

(2) This methyl ester compound (5.26 g) and hydrazine monohydrate (4.53 ml) in ethanol (10 ml) were heated at reflux for 4 hours while stirring. The solvent was evaporated under reduced pressure, and the thus-precipitated crystals were collected by filtration, thereby giving 4.50 g of the desired compound.

REFERENCE EXAMPLE 66

Preparation of 4-benzyloxy-3-methoxybenzoic acid (1) Benzyl bromide (3.59 ml) and potassium carbonate (5.69 g) were added to an acetone (50 ml) solution of methyl 4-hydroxy-3-methoxybenzoate (5.00 g), and heated at reflux for 4 hours. After removing solid matter by filtration and concentrating the filtrate under reduced pressure, the residue was dissolved in ethyl acetate, and washed with saturated aqueous sodium hydrogencarbonate solution and saturated brine. The organic layer was dried over $MgSO_4$, and the solvent was evaporated under reduced pressure, thereby giving 7.47 g of methyl 4-benzyloxy-3-methoxybenzoate.

(2) An aqueous 2 M sodium hydroxide solution (13.72 ml) was added to an ethanol (15 ml) solution of the above-obtained 4-benzyloxy compound (7.47 g), and heated at reflux for 2 hours. After evaporating the solvent under reduced pressure, 2M hydrochloric acid was added, and the thus-precipitated crystals were filtered, thereby giving 7.00 g of the desired compound.

REFERENCE EXAMPLE 67

Preparation of 4-methoxy-3-(N-methylsulfamoyl)benzoic acid (1) To chlorosulfonic acid (20.00 ml) was added 4-methoxybenzoic acid (4.56 g) at 25° C. and stirred for 3 hours. Water was added at 0° C. to the reaction mixture, and the precipitated crystals were filtered, thereby giving 3.39 g of 3-chlorosulfonyl-4-methoxybenzoic acid.

(2) This 3-chlorosulfonyl compound (1.00 g) was added at 25° C. to a 40% aqueous methylamine solution (10.00 ml) and stirred overnight. After adding 2 M hydrochloric acid to the reaction solution, the thus-precipitated crystals were collected by filtration, thereby giving 0.92 g of the desired compound.

REFERENCE EXAMPLE 68

Preparation of 4-methoxy-3-phenylbenzoic acid (1) A reaction was carried out in the same manner as in Reference Example 1 except that the 3-bromo-2-furancarboxylic acid used in Reference Example 1 was replaced with 3-bromo-4-methoxybenzoic acid (4.62 g). The crude product was purified by silica gel column chromatography (eluent: ethyl acetate/hexane=1/10), thereby giving 4.65 g of ethyl 3-bromo-4-methoxybenzoate.

(2) Using 2.59 g of this ethyl ester compound and phenylboronic acid (2.44 g), a reaction and treatment was conducted in the same manner as in Reference Example 5(1), thereby giving 2.51 g of ethyl 4-methoxy-3-phenylbenzoate.

(3) An ethanol (10 ml) solution of the above-obtained 3-phenyl compound (2,31 g) was mixed with a 1 M aqueous sodium hydroxide solution (10.80 ml) and heated at reflux for 2 hours while stirring. After evaporating the solvent under reduced pressure, 1 M hydrochloric acid was added, and the thus-precipitated crystals were collected by filtration, thereby giving 1.93 g of the desired compound.

REFERENCE EXAMPLE 69

Preparation of 4-phenyl-3-[3-(2,3,5,6-tetramethylbenzyloxy)phenyl]-2-furancarboxylic acid hydrazide and 3-phenyl-4-[3-(2,3,5,6-tetramethylbenzyloxy)phenyl]-2-furancarboxylic acid hydrazide (1) A reaction and treatment was carried out in the same manner as in Reference Example 5(1) using ethyl 3,4-dibromo-2-furancarboxylate (2.00 g) and 3-benzyloxyphenylboronic acid (1.80 g). The residue was purified by silica gel column chromatography (eluent: ethyl acetate/hexane=1/20), thereby giving 1.70 g of a mixture of ethyl 3-(3-benzyloxyphenyl)-4-bromo-2-furancarboxylate and ethyl 4-(3-benzyloxyphenyl)-3-bromo-2-furancarboxylate and 0.26 g of ethyl 3,4-bis(3-benzyloxyphenyl)-2-furancarboxylate.

(2) A reaction and treatment was carried out in the same manner as in Reference Example 5(1) using phenylboronic acid (0.37 g) and 0.80 g of the above-obtained mixture composed of ethyl 3-(3-benzyloxyphenyl)-4-bromo-2-furancarboxylate and ethyl 4-(3-benzyloxyphenyl)-3-bromo-2-furancarboxylate. The residue was purified by silica gel column chromatography (eluent: ethyl acetate/hexane=1/20), thereby giving 0.65 g of a mixture of ethyl 3-(3-benzyloxyphenyl)-4-phenyl-2-furancarboxylate and ethyl 4-(3-benzyloxyphenyl)-3-phenyl-2-furancarboxylate.

(3) A reaction and treatment was carried out in the same manner as in Reference Example 40 using the above-obtained mixture (0.65 g) of ethyl 3-(3-benzyloxyphenyl)-4-phenyl-2-furancarboxylate and ethyl 4-(3-benzyloxyphenyl)-3-phenyl-2-furancarboxylate, thereby giving 0.50 g of a mixture composed of ethyl 3-(3-hydroxyphenyl)-4-phenyl-2-furancarboxylate and ethyl 4-(3-hydroxyphenyl)-3-phenyl-2-furancarboxylate.

(4) A reaction and treatment was carried out in the same manner as in Reference Example 3 using the above-obtained mixture (0.50 g) of ethyl 3-(3-hydroxyphenyl)-4-phenyl-2-furancarboxylate and ethyl 4-(3-hydroxyphenyl)-3-phenyl-2-furancarboxylate. The residue was purified by silica gel column chromatography (eluent: ethyl acetate/hexane=1/20), thereby giving 0.23 g of ethyl 4-phenyl-3-[3-(2,3,5,6-tetramethylbenzyloxy)phenyl]-2-furancarboxylate and 0.09 g of ethyl 3-phenyl-4-[3-(2,3,5,6-tetramethylbenzyloxy)phenyl]-2-furancarboxylate.

(5) Using the above-obtained ethyl 4-phenyl-3-[3-(2,3,5,6-tetramethylbenzyloxy)phenyl]-2-furancarboxylate (0.23 g) and ethyl 3-phenyl-4-[3-(2,3,5,6-tetramethylbenzyloxy)phenyl]-2-furancarboxylate (0.09 g), reactions and treatments were carried out in the same manner as in Reference Example 11(2), thereby giving 0.21 g of 4-phenyl-3-[3-(2,3,5,6-tetramethylbenzyloxy)phenyl]-2-furancarboxylic acid hydrazide and 0.08 g of 3-phenyl-4-[3-(2,3,5,6-tetramethylbenzyloxy)phenyl]-2-furancarboxylic acid hydrazide, respectively.

REFERENCE EXAMPLE 70

Preparation of 3-[3-(4-pyridylmethyloxy)phenyl]-2-furancarboxylic acid hydrazide A reaction and treatment was carried out in the same manner as in Reference Example 3 except that the 2,3,5,6-tetramethylbenzyl chloride used in Reference Example 3 was replaced with 4-pyridylmethyl bromide, thereby giving 3-[3-(4-pyridylmethyloxy)phenyl]-2-furancarboxylic acid 4-pyridylmethyl ester. Using this product, a reaction and treatment was carried out in the same manner as in Reference Example 11(2), thereby giving the desired compound.

REFERENCE EXAMPLE 71

Preparation of 3-(3-acetylaminophenyl)-2-furancarboxylic acid hydrazide (1) A reaction and treatment was carried out in the same manner as in Reference Example 5(1) except that the 2-benzyloxyphenylboronic acid used in Reference Example 5(1) was replaced with 3-aminophenylboronic acid, thereby giving ethyl 3-(3-aminophenyl)-2-furancarboxylate.

(2) Acetic anhydride (0.40 g) was added to a mixture of the above-obtained 3-(3-aminophenyl) compound (0.60 g) and pyridine (4 ml) at 0° C., and stirred for 3 hours at 25° C. The reaction solution was poured into cooled 1 M hydrochloric acid and diluted with ethyl acetate. After washing the organic layer with water and drying it over $MgSO_4$, the solvent was evaporated under reduced pressure, thereby giving 0.65 g of ethyl 3-(3-acetylaminophenyl)-2-furancarboxylate.

(3) Hydrazine monohydrate (1.00 g) was added to an ethanol (2 ml) solution of 0.36 g of the above-obtained 3-(3-acetylaminophenyl) compound and heated at reflux for 3 hours. After cooling, ethyl acetate (50 ml) and water (10 ml) were added to the reaction solution, and the organic layer was separated and concentrated under reduced pressure, thereby giving 0.28 g of the desired compound.

REFERENCE EXAMPLE 72

Preparation of 3-(3-benzoylaminophenyl)-2-furancarboxylic acid hydrazide (1) A reaction and treatment was carried out in the same manner as in Reference Example 71(2) except that the acetic anhydride used in Reference Example 71(2) was replaced with benzoyl chloride, thereby giving 0.20 g of ethyl 3-(3-benzoylaminophenyl)-2-furancarboxylate.

(2) Using this 3-(3-benzoylaminophenyl) compound (0.20 g), a reaction and treatment was carried out in the same manner as in Reference Example 71(3), thereby giving 0.20 g of the desired compound.

REFERENCE EXAMPLE 73

Preparation of 3-[3-(N-acetyl-N-benzylamino)phenyl]-2-furancarboxylic acid hydrazide Sodium hydride (60%, 0.053 g) was added to a DMF (15 ml) solution of the compound of Reference Example 71(2) (0.30 g) at 0° C. and stirred for 30 minutes. Benzyl bromide (0.23 g) was then further added and stirred overnight at 25° C. The reaction solution was poured into water and diluted with ethyl acetate, and the organic layer was washed with water and dried over $MgSO_4$. The solvent was evaporated under reduced pressure, and the residue was purified by silica gel column chromatography (eluent: ethyl acetate/hexane=1/2), thereby giving ethyl 3-[3-(N-acetyl-N-benzylamino)phenyl]-2-furancarboxylate.

Using this compound, a reaction and treatment was carried out in the same manner as in Reference Example 71(3), thereby giving 0.35 g of the desired compound.

REFERENCE EXAMPLE 74

Preparation of 3-(3-benzyloxycarbonylaminophenyl)-2-furancarboxylic acid hydrazide (1) Benzyl chloroformate (0.41 g) was added to a pyridine (15 ml) solution of the compound of Reference Example 71(1) (0.50 g) at 0° C. and stirred for 3 hours at 25° C. The reaction solution was poured into 1 M hydrochloric acid and diluted with ethyl acetate. The organic layer was washed with water and dried over $MgSO_4$, and the solvent was evaporated under reduced pressure. The residue was purified by silica gel column chromatography (eluent: ethyl acetate/hexane=1/4), thereby giving 0.58 g of ethyl 3-(3-benzyloxycarbonylaminophenyl)-2-furancarboxylate.

(2) Using this 3-(3-benzyloxycarbonylaminophenyl) compound (0.58 g), a reaction and treatment was carried out in the same manner as in Reference Example 71(3), thereby giving 0.45 g of the desired compound.

REFERENCE EXAMPLE 75

Preparation of 3,4-bis(3-benzyloxyphenyl)-2-furancarboxylic acid hydrazide

A reaction and treatment was carried out in the same manner as in Reference Example 11(2) using ethyl 3,4-bis(3-benzyloxyphenyl)-2-furancarboxylate (0.25 g) as obtained in Reference Example 69(1), thereby giving 0.17 g of the desired compound.

REFERENCE EXAMPLE 76

Preparation of 3,4-bis[3-(2,3,5,6-tetramethylbenzyloxy)phenyl]-2-furancarboxylic acid hydrazide A reaction and treatment was carried out in the same manner as in Reference Example 28 except that the 4-bromophenol used in Reference Example 28 was replaced with 3-bromophenol, thereby giving 3-(2,3,5,6-tetramethylbenzyloxy)bromobenzene. Using this compound, a reaction and treatment was carried out in the same manner as in Reference Example 69(1), thereby giving ethyl 3,4-bis[3-(2,3,5,6-tetramethylbenzyloxy)phenyl]-2-furancarboxylate. Using this compound, a reaction and treatment was carried out in the same manner as in Reference Example 11(2), thereby giving the desired compound.

REFERENCE EXAMPLE 77

Preparation of 3-[3-(2-hydroxy-2-phenylethoxy)phenyl]-2-furancarboxylic acid hydrazide (1) A reaction and treatment was carried out in the same manner as in Reference Example 5 except that the 2-benzyloxyphenylboronic acid used in Reference Example 5 was replaced with 3-benzyloxyphenylboronic acid, thereby giving ethyl 3-(3-hydroxyphenyl)-2-furancarboxylate.

(2) A reaction and treatment was carried out in the same manner as in Reference Example 6 except that the compound of Reference Example 5 and the 2,3,5,6-tetramethylbenzyl chloride used in Reference Example 6 were replaced with the above-obtained compound and bromoacetophenone, respectively, thereby giving ethyl 3-[3-(2-oxo-2-phenylethoxy)phenyl]-2-furancarboxylate.

(3) Sodium borohydride (0.025 g) was added to a mixture of the above-obtained 3-[3-(2-oxo-2-phenylethoxy)phenyl] compound (0.20 g) and methanol (20 ml) at 0° C., and stirred for 1 hour. The solvent was evaporated under reduced pressure, and ethyl acetate and 1 M hydrochloric acid were added to the residue. After washing the organic layer with water and drying it over $MgSO_4$, the solvent was evaporated under reduced pressure, thereby giving 0.17 g of ethyl 3-[3-(2-hydroxy-2-phenylethoxy)phenyl]-2-furancarboxylate.

(4) Hydrazine monohydrate (0.97 ml) was added to an ethanol (5 ml) solution of the above-obtained 3-[3-(2-hydroxy-2-phenylethoxy)phenyl] compound (0.17 g) and heated at reflux for 3 hours. After cooling, ethyl acetate (50 ml) and water (10 ml) were added to the reaction solution, and the organic layer was separated and concentrated under reduced pressure, thereby giving 0.16 g of the desired compound.

REFERENCE EXAMPLE 78

Preparation of 3-(4-phenoxyphenyl)-2-furancarboxylic acid hydrazide

A reaction and treatment was carried out in the same manner as in Reference Example 15 except that the 1,3-dibromobenzene used in Reference Example 15 was replaced with 1,4-dibromobenzene, thereby giving 4-phenoxy bromobenzene. Using this compound, reactions and treatments were carried out in the same manner as in Reference Examples 16, 17 and 18, thereby giving the desired compound.

REFERENCE EXAMPLE 79

Preparation of 3-(4-benzyloxyphenyl)-2-furancarboxylic acid hydrazide

A reaction and treatment was carried out in the same manner as in Reference Example 17 except that the 3-phenoxyphenylboronic acid used in Reference Example 17 was replaced with 4-benzyloxyphenylboronic acid, thereby giving ethyl 3-(4-benzyloxyphenyl)-2-furancarboxylate. Using this compound, a reaction and treatment was carried out in the same manner as in Reference Example 18, thereby giving the desired compound.

REFERENCE EXAMPLE 80

Preparation of 4-acetoxy-3-nitrobenzoic acid

Acetic anhydride (550 ml) was added to a mixture of 4-hydroxy-3-nitrobenzoic acid (100 g) and pyridine (119.82 ml), and stirred for 3 hours at 25° C. The reaction solution was poured into a cooled hydrochloric acid solution, and the thus-precipitated crystals were filtered and washed with cold water. The crystals were recrystallized from ethyl acetate/hexane, thereby giving 85.45 g of the desired compound.

REFERENCE EXAMPLE 81

Preparation of 3-[3-(2-methylbenzyloxy)phenyl]-2-furancarboxylic acid hydrazide

Cesium carbonate (2.51 g), potassium iodide (0.11 g) and 2-methylbenzyl chloride (1.09 ml) were added to an acetone solution (10 ml) of an ethyl ester (1.40 g) obtained by a reaction and treatment carried out in the same manner as in Reference Example 1 using the compound of Reference Example 2, and heated at reflux. After filtering the reaction solution, the solvent in the filtrate was evaporated under reduced pressure, and the residue was purified by silica gel column chromatography (eluent: ethyl acetate/hexane=1/10), thereby giving 1.40 g of ethyl 3-[3-(2-methylbenzyloxy)phenyl]-2-furancarboxylate. This product (1.40 g) was dissolved in ethanol (2 ml), and hydrazine monohydrate (1.69 ml) was added thereto and heated at reflux for 5 hours. After evaporating the solvent in the reaction solution under reduced pressure, the residue was diluted with ethyl acetate and washed with saturated brine. The organic layer was dried over $MgSO_4$, and the solvent was evaporated under reduced pressure, thereby giving 1.40 g of the desired compound.

REFERENCE EXAMPLE 82

Preparation of 3-[3-(3-methylsulfonylamidebenzyloxy)phenyl]-2-furancarboxylic acid hydrazide (1) A reaction and treatment was carried out in the same manner as in Reference Example 81 except that the 2-methylbenzyl chloride used in Reference Example 81 was replaced with 3-nitrobenzyl bromide, thereby giving ethyl 3-[3-(3-nitrobenzyloxy)phenyl]-2-furancarboxylate.

(2) A mixture of ethyl 3-[3-(3-nitrobenzyloxy)phenyl]-2-furancarboxylate (2.21 g), reduced iron (1.75 g), ammonium chloride (0.67 g), ethanol (30 ml) and water (10 ml) was heated at reflux for 1 hour. After filtering the reaction solution through celite, the solvent in the filtrate was evaporated under reduced pressure. The residue was purified by silica gel column chromatography (eluent: ethyl acetate/hexane=1/3), thereby giving 1.60 g of ethyl 3-[3-(2-aminobenzyloxy)phenyl)-2-furancarboxylate.

(3) Methylsulfonyl chloride (0.41 ml) was added dropwise to a mixed solution of ethyl 3-[3-(3-aminobenzyloxy)phenyl]-2-furancarboxylate (1.60 g), dichloromethane (10 ml) and pyridine (0.60 ml) under ice-cooling. One hour later, the reaction solution was diluted with dichloromethane, and successively washed with 1 M hydrochloric acid, saturated aqueous sodium hydrogen carbonate solution and saturated brine. After drying the organic layer over $MgSO_4$, the solvent was evaporated under reduced pressure, thereby giving 1.73 g of ethyl 3-[3-(3-methylsulfonylamidebenzyloxy)phenyl]-2-furancarboxylate.

(4) Ethyl 3-[3-(3-methylsulfonylamidebenzyloxy)phenyl]-2-furancarboxylate (1.73 g) was dissolved in ethanol (2 ml), mixed with hydrazine monohydrate (2.09 ml) and heated at reflux for 5 hours. After evaporating the solvent in the reaction solution under reduced pressure, the residue was diluted with ethyl acetate and washed with saturated brine. The organic layer was dried over $MgSO_4$, and the solvent was evaporated under reduced pressure, thereby giving 1.50 g of the desired compound.

REFERENCE EXAMPLE 83

Preparation of 3-[3-(2-methoxy-5-pyridylmethyloxy)phenyl]-2-furancarboxylic acid hydrazide (1) A reaction and treatment was carried out in the same manner as in Reference Example 82 except that the 2-methylbenzyl chloride of Reference Example 81 was replaced with 2-chloro-5-pyridylmethyl chloride, thereby giving ethyl 3-[3-(2-chloro-5-pyridylmethyloxy)phenyl]-2-furancarboxylate.

(2) A mixture of this ester (1.5 g) and sodium methoxide (28% methanol solution; 20 ml) was heated at reflux overnight. The solvent was evaporated under reduced pressure, and water and ethyl acetate were added to the residue. The organic layer was washed with water and saturated brine, and dried over $MgSO_4$. The solvent was evaporated under reduced pressure, thereby giving 3-[3-(2-methoxy-5-pyridylmethyloxy)phenyl]-2-furancarboxylic acid.

(3) This carboxylic acid was reacted and treated in the same manner as in Reference Example 1 to prepare an ethyl ester. This ethyl ester was subjected to reaction and treatment in the same manner as in Reference Example 10(3), thereby giving the desired compound.

REFERENCE EXAMPLE 84

Preparation of 3-(3-methanesulfonyloxyphenyl)-2-furancarboxylic acid hydrazide

Methanesulfonyl chloride (0.73 ml) was added to a mixture of the compound of Reference Example 2 (1.49 g), dichloromethane (10 ml) and triethylamine (1.34 ml) under ice-cooling, and stirred overnight. The reaction solution was diluted with dichloromethane, and successively washed with 1 M hydrochloric acid, saturated aqueous sodium hydrogen carbonate solution and saturated brine. After drying over $MgSO_4$, the solvent was evaporated under reduced pressure. The residue was purified by silica gel column chromatography (eluent: 0%→10% ethyl acetate/hexane gradient), thereby giving 1.40 g of ethyl 3-(3-methanesulfonyloxyphenyl)-2-furancarboxylate. Using this compound, a reaction and treatment was carried out in the same manner as in Reference Example 10(3), thereby giving 1.40 g of the desired compound.

REFERENCE EXAMPLE 85

Preparation of 4-acetoxy-3-trifluoromethylbenzoic acid

A reaction and treatment was carried out in the same manner as in Reference Example 62 except that the methyl 3-cyano-4-methoxybenzoate used in Reference Example 62 was replaced with methyl 4-methoxy-3-trifluoromethyl benzoate, thereby giving 4-hydroxy-3-trifluoromethylbenzoic acid. Using this compound, a reaction and treatment was carried out in the same manner as in Reference Example 80, thereby giving the desired compound.

REFERENCE EXAMPLE 86

Preparation of 4-acetoxy-3-tert-butyloxycarbonyl benzoic acid (1) A mixture of dimethyl 4-hydroxyisophthalate (10 g) and pyridine (100 ml) was heated at reflux overnight. After cooling, 6 M hydrochloric acid was added to the reaction solution. The thus-precipitated crystals were filtered, thereby giving 9.15 g of methyl 3-carboxy-4-hydroxybenzoate.

(2) A mixture of methyl 3-carboxy-4-hydroxybenzoate (3.92 g), N,N-dimethylformamide di-tert-butyl acetal (19.19 ml) and toluene (50 ml) was heated at reflux for 1 hour. After cooling, the reaction solution was diluted with toluene, washed with 10% citric acid solution and dried over $MgSO_4$. The solvent was evaporated under reduced pressure, and the residue was purified by silica gel column chromatography (eluent: ethyl acetate/hexane=1/20), thereby giving 4.00 g of methyl 3-tert-butyloxycarbonyl-4-hydroxy-benzoate.

(3) To a mixture of 1.00 g of the methyl 3-tert-butyloxycarbonyl-4-hydroxybenzoate and dioxane (10 ml) was added a 1 M aqueous sodium hydroxide solution (16 ml) at 25° C. and stirred overnight. The reaction solution was neutralized with 1 M hydrochloric acid, extracted with ethyl acetate, and dried over $MgSO_4$. The solvent was evaporated under reduced pressure, thereby giving 0.78 g of 3-tert-butyloxycarbonyl-4-hydroxybenzoic acid.

(4) Using this 3-tert-butyloxycarbonyl-4-hydroxybenzoic acid, a reaction and treatment was carried out in the same manner as in Reference Example 80, thereby giving the desired compound.

REFERENCE EXAMPLE 87

Preparation of ethyl 3-(4-hydroxyphenyl)-2-furancarboxylate

Using 4-hydroxyphenylboronic acid pinacol cyclic ester, a reaction and treatment was carried out in the same manner as in Reference Example 2, thereby giving 3-(4-hydroxyphenyl)-2-furancarboxylic acid. A reaction and treatment was further carried out in the same manner as in Reference Example 1, thereby giving the desired compound.

REFERENCE EXAMPLE 88

Preparation of 3-(3-phenethyloxyphenyl)-2-furancarboxylic acid hydrazide

Diisopropyl azodicarboxylate (1.26 ml) was added dropwise to a mixture of an ethyl ester (0.90 g) obtained by a reaction and treatment with the compound of Reference Example 2 carried out in the same manner as in Reference Example 1, phenethyl alcohol (0.72 ml), triphenylphosphine (1.26 g) and anhydrous THF (40 ml) at 0° C., and stirred at 25° C. Three hours later, the solvent in the reaction solution was evaporated under reduced pressure. The residue was purified by silica gel column chromatography (eluent: 0%→25% ethyl acetate/hexane gradient), thereby giving 1.34 g of ethyl 3-(3-phenoxyphenyl)-2-furancarboxylate. Using this compound, a reaction and treatment was carried out in the same manner as in Reference Example 10(3), thereby giving 1.29 g of the desired compound.

REFERENCE EXAMPLE 89

Preparation of 3-[4-(phenylaminocarbonylmethyloxy)phenyl]-2-furancarboxylic acid hydrazide (1) Using the compound of Reference Example 87 and 2-chloro-N-phenylacetamide, an alkylation reaction and treatment was carried out in the same manner as in Reference Example 81, thereby giving ethyl 3-[4-(phenylaminocarbonylmethyloxy)phenyl]-2-furancarboxylate.

(2) Using this compound, a reaction and treatment was carried out in the same manner as in Reference Example 52(2), thereby giving the desired carboxylic acid.

(3) A mixed solution of this carboxylic acid (1.2 g), tert-butoxycarbonyl hydrazide (0.56 g), WSC (1.05 g) and dichloromethane (20 ml) was stirred at 25° C. for 1 hour. The reaction solution was then washed with saturated brine and dried over $MgSO_4$. The solvent was evaporated under reduced pressure, and the residue was purified by silica gel column chromatography (eluent: 0%→70% ethyl acetate/hexane gradient), thereby giving 1.2 g of condensate.

(4) A mixture of 0.6 g of this condensate and 4 M hydrogen chloride/ethyl acetate (14 ml) was stirred overnight at 25° C., and neutralized by saturated aqueous sodium hydrogencarbonate solution. The organic layer was washed with saturated brine and dried over $MgSO_4$. The solvent was evaporated under reduced pressure, thereby giving 0.5 g of the desired compound.

REFERENCE EXAMPLE 90

Preparation of 3-[4-(phenylcarbonylmethyloxy)phenyl]-2-furancarboxylic acid hydrazide Using the compound of Reference Example 87 and 2-bromoacetophenone, a reaction and treatment was conducted in the same manner as in Reference Example 89, thereby giving the desired product.

EXAMPLE 1

Preparation of 3-[3-(2,3,5,6-tetramethylbenzyloxy) phenyl]-2-furancarboxylic acid 2-(3-cyano-4-hydroxybenzoyl)hydrazide (a) A mixture of 3-cyano-4-hydroxybenzoic acid pentafluorophenyl ester (compound of Reference Example 63; 0.45 g) and 3-[3-(2,3,5,6-tetramethylbenzyloxy)phenyl]-2-furancarboxylic acid hydrazide (compound of Reference Example 4; 0.50 g) in DMF (5 ml) was stirred at 70° C. overnight. The reaction solution was then diluted with ethyl acetate, washed with 1 M hydrochloric acid and water, and dried over $MgSO_4$. The solvent was evaporated under reduced pressure, and the residue was purified by silica gel column chromatography (eluent: 0%→10% methanol/chloroform gradient) and recrystallized from ethyl acetate, thereby giving 0.31 g of the desired compound. Melting point: 210-211° C.

(b) A mixture composed of the compound of Reference Example 4 (1.09 g) and the compound of Reference Example 63 (0.99 g) in ethyl acetate (15 ml) was heated at reflux while stirring overnight. The thus-precipitated crystals were filtered, and recrystallized from methanol/ethyl acetate, thereby giving 1.25 g of the desired compound. Melting point: 210-211° C.

$^1$H-NMR (DMSO-$d_6$, δ): 2.16 (s, 6H), 2.18 (s, 6H), 5.07 (s, 2H), 6.97 (s, 1H), 7.00-7.05 (m, 2H), 7.09 (d, J=8.8 Hz, 1H), 7.31-7.37 (m, 2H), 7.45-7.49 (m, 1H), 7.95 (d, J=1.8 Hz, 1H), 8.00 (dd, J=2.2, 8.8 Hz, 1H), 8.13 (d, J=2.2 Hz, 1H), 10.35 (s, 1H), 10.38 (s, 1H), 11.83 (br s, 1H)

EXAMPLE 2

Preparation of 3-(3-phenoxyphenyl)-2-furancarboxylic acid 2-(3-cyano-4-hydroxybenzoyl)hydrazide A mixture of 3-(3-phenoxyphenyl)-2-furancarboxylic acid hydrazide (compound of Reference Example 18, 0.58 g) and the compound of Reference Example 63 (0.65 g) in ethyl acetate (15 ml) was heated overnight at reflux while stirring. The reaction solution was then washed with water and dried over $MgSO_4$. The solvent was evaporated under reduced pressure, and the residue was recrystallized from ethyl acetate/hexane, thereby giving 0.38 g of the desired compound. Melting point: 227-228° C.

$^1$H-NMR (DMSO-$d_6$, δ): 6.93-7.07 (m, 4H), 7.08-7.17 (m, 2H), 7.32-7.46 (m, 3H), 7.48-7.58 (m, 2H), 7.97 (s, 1H), 8.03 (dd, J=2.2, 9.0 Hz, 1H), 8.16 (d, J=2.2 Hz, 1H), 10.39 (s, 1H), 10.40 (s, 1H), 11.88 (br s, 1H)

EXAMPLE 3

Preparation of 3-(3-benzyloxyphenyl)-2-furancarboxylic acid 2-(3-cyano-4-hydroxybenzoyl)hydrazide A reaction and treatment was carried out in the same manner as in Example 2 except that the compound of Reference Example 18 used in Example 2 was replaced with the of Reference Example 20 (0.41 g), thereby giving 0.15 g of the desired compound. Melting point: 190-195° C. (Recrystallized from methanol/ethyl acetate)

EXAMPLE 4

Preparation of 3-(3-phenethyloxyphenyl)-2-furancarboxylic acid 2-(3-cyano-4-hydroxybenzoyl)hydrazide A reaction and treatment was carried out in the same manner as in Example 2 except that the compound of Reference Example 18 used in Example 2 was replaced with the compound of Reference Example 21 (0.44 g), thereby giving 0.19 g of the desired compound. Melting point: 131-134° C. (Recrystallized from ethyl acetate/hexane)

$^1$H-NMR (DMSO-$d_6$, δ): 3.04 (t, J=7.0 Hz, 2H), 4.21 (t, J=7.0 Hz, 2H), 6.90-6.95 (m, 1H), 7.00 (d, J=1.8 Hz, 1H), 7.12 (d, J=9.0 Hz, 1H), 7.20-7.36 (m, 7H), 7.42-7.44 (m, 1H), 7.95 (d, J=1.8 Hz, 1H), 8.02 (dd, J=2.2, 9.0 Hz, 1H), 8.16 (d, J=2.2 Hz, 1H), 10.36 (s, 1H), 10.39 (s, 1H), 11.88 (br s, 1H)

EXAMPLE 5

Preparation of 3-(2-benzyloxyphenyl)-2-furancarboxylic acid 2-(3-cyano-4-hydroxybenzoyl)hydrazide A mixture of the compound of Reference Example 22 (1.00 g), 3-cyano-4-hydroxybenzoic acid (compound of Reference Example 62, 0.65 g) and WSC (0.93 g) in dichloromethane (70 ml) was stirred at 25° C. for 2 hours. The reaction solution was poured into 1 M hydrochloric acid, and chloroform (100 ml) was added thereto. The precipitate was filtered off, and the organic layer was concentrated under reduced pressure. The residue was washed with 1 M hydrochloric acid and recrystallized from ethyl acetate/hexane, thereby giving 0.20 g of the desired compound. Melting point: 118-120° C.

$^1$H-NMR (DMSO-$d_6$, δ): 5.11 (s, 1H), 6.79 (d, J=1.7 Hz, 1H), 6.89-6.97 (m, 1H), 7.06-7.15 (m, 2H), 7.35-7.41 (m, 7H), 7.88 (d, J=1.7 Hz, 1H), 8.00 (dd, J=2.2, 8.8 Hz, 1H), 8.13 (d, J=2.2 Hz, 1H), 10.25 (s, 1H), 10.31 (s, 1H), 11.87 (br s, 1H)

EXAMPLE 6

Preparation of 3-(2-biphenylyl)-2-furancarboxylic acid 2-(3-cyano-4-hydroxybenzoyl)hydrazide A mixture of the compound of Reference Example 23 (0.28 g) and the compound of Reference Example 63 (0.33 g) in DMF (5 ml) was stirred overnight at 70° C. in an oil bath. The reaction solution was diluted with ethyl acetate, washed with water and dried over $MgSO_4$. The solvent was evaporated under reduced pressure, and the residue was recrystallized from methanol/chloroform, thereby giving 0.31 g of the desired compound. Melting point: 159-162° C.

$^1$H-NMR (DMSO-$d_6$, δ): 6.10 (d, J=1.3 Hz, 1H), 7.11 (d, J=8.8 Hz, 1H), 7.08-7.47 (m, 9H), 7.70 (d, J=1.3 Hz, 1H), 8.02 (dd, J=1.8, 8.8 Hz, 1H), 8.15 (d, J=1.8 Hz, 1H), 10.27 (s, 1H), 10.34 (s, 1H), 11.87 (br s, 1H)

EXAMPLE 7

Preparation of 3-(2-hydroxyphenyl)-2-furancarboxylic acid 2-(3-cyano-4-hydroxybenzoyl)hydrazide A reaction and treatment was carried out in the same manner as in Example 6 except that the compound of Reference Example 23 used in Example 6 was replaced with the compound of Reference Example 26 (0.22 g), thereby giving 0.26 g of the desired compound. Melting point: 135-140° C. (Recrystallized from methanol/chloroform)

EXAMPLE 8

Preparation of 3-(2-benzylphenyl)-2-furancarboxylic acid 2-(3-cyano-4-hydroxybenzoyl)hydrazide A reaction and treatment was carried out in the same manner as in Example 2 except that the compound of Reference Example 18 used in Example 2 was replaced with 3-(2-benzylphenyl)-2-furancarboxylic acid hydrazide (compound of Reference Example 25, 0.29 g), thereby giving 0.35 g of the desired compound. Melting point: 175-176° C. (Recrystallized from methanol/ethyl acetate/chloroform)

$^1$H-NMR (DMSO-$d_6$, δ): 3.89 (s, 2H), 6.55 (d, J=1.8 Hz, 1H), 7.08-7.30 (m, 8H), 7.91 (d, J=1.8 Hz, 1H), 8.01 (dd, J=2.0, 8.8 Hz, 1H), 8.14 (d, J=2.0 Hz, 1H), 10.33 (s, 2H), 11.87 (br s, 1H)

EXAMPLE 9

Preparation of 3-[2-(2,3,5,6-tetramethylbenzyloxy) phenyl]-2-furancarboxylic acid 2-(3-cyano-4-hydroxybenzoyl)hydrazide In ethyl acetate (10 ml), a mixture composed of 3-[2-(2,3,5,6-tetramethylbenzyloxy)phenyl]-2-furancarboxylic acid hydrazide (compound of Reference Example 6, 0.36 g) and the compound of Reference Example 63 (0.33 g) was heated at reflux overnight while stirring. The thus-precipitated crystals were filtered and recrystallized from ethyl acetate, thereby giving 0.18 g of the desired compound. Melting point: 215-217° C.

$^1$H-NMR (DMSO-$d_6$, δ): 2.13 (s, 6H), 2.18 (s, 6H), 5.05 (s, 2H), 6.58 (d, J=1.7 Hz, 1H), 6.92-7.00 (m, 2H), 7.10 (d, J=8.8 Hz, 1H), 7.30-7.41 (m, 3H), 7.78 (d, J=1.7 Hz, 1H), 8.00 (dd, J=2.2, 8.8 Hz, 1H), 8.13 (d, J=2.2 Hz, 1H), 10.20 (s, 1H), 10.29 (s, 1H), 11.87 (br s, 1H)

EXAMPLE 10

Preparation of 3-(2-isopropoxyphenyl)-2-furancarboxylic acid 2-(3-cyano-4-hydroxybenzoyl)hydrazide A reaction and treatment was carried out in the same manner as in Example 2 except that the compound of Reference Example 18 used in Example 2 was replaced with the compound of Reference Example 7, thereby giving 0.17 g of the desired compound. Melting point: 128-130° C. (Recrystallized from ethyl acetate)

EXAMPLE 11

Preparation of 3-(2-propoxyphenyl)-2-furancarboxylic acid 2-(3-cyano-4-hydroxybenzoyl)hydrazide A mixture of the compound of Reference Example 8 (0.29 g) and the compound of Reference Example 63 (0.33 g) in ethyl acetate (10 ml) was heated at reflux overnight while stirring. The reaction solution was diluted with ethyl acetate, washed with water, and dried over MgSO$_4$. The solvent was evaporated under reduced pressure, and the residue was purified by silica gel column chromatography (eluent: 0%→10% methanol/chloroform gradient), thereby giving 0.36 g of the desired compound. Melting point: 114-117° C. (Recrystallized from ethyl acetate/diethyl ether)

EXAMPLE 12

Preparation of 3-(2-phenethyloxyphenyl)-2-furancarboxylic acid 2-(3-cyano-4-hydroxybenzoyl)hydrazide A mixture composed of the compound of Reference Example 9 (0.16 g) and the compound of Reference Example 63 (0.17 g) in DMF (5 ml) was stirred overnight at 70° C. in an oil bath. The reaction solution was diluted with ethyl acetate, washed with water and dried over MgSO$_4$. The solvent was evaporated under reduced pressure, and the residue was purified by silica gel column chromatography (eluent: 0%→80% ethyl acetate/hexane gradient), thereby giving 0.01 g of the desired compound. HPLC retention time: 10.39 minutes.

EXAMPLE 13

Preparation of 3-(2-phenoxyphenyl)-2-furancarboxylic acid 2-(3-cyano-4-hydroxybenzoyl)hydrazide A reaction and treatment was carried out in the same manner as in Example 1(a) except that the compound of Reference Example 4 used in Example 1(a) was replaced with the compound of Reference Example 19 (0.29 g), thereby giving 0.19 g of the desired compound. Melting point: 134-135° C. (Recrystallized from chloroform)

$^1$ H-NMR (DMSO-$d_6$, δ): 6.73 (d, J=1.7 Hz, 1H), 6.89-6.96 (m, 3H), 7.03-7.20 (m, 3H), 7.27-7.39 (m, 3H), 7.50 (d, J=7.5 Hz, 1H), 7.85 (d, J=1.7 Hz, 1H), 8.02 (dd, J=1.8, 8.8 Hz, 1H), 8.16 (d, J=1.8 Hz, 1H), 10.31 (s, 1H), 10.34 (s, 1H), 11.87 (br s, 1H)

EXAMPLE 14

Preparation of 3-(2-cyclohexylmethyloxyphenyl)-2-furancarboxylic acid 2-(3-cyano-4-hydroxybenzoyl) hydrazide A reaction and treatment was carried out in the same manner as in Example 1(a) except that the compound of Reference Example 4 used in Example 1(a) was replaced with the compound of Reference Example 27, thereby giving 0.16 g of the desired compound. Melting point: 142-143° C. (Recrystallized from ethyl acetate/diethyl ether)

EXAMPLE 15

Preparation of 3-[4-(2,3,5,6-tetramethylbenzyloxy) phenyl]-2-furancarboxylic acid 2-(3-cyano-4-hydroxybenzoyl)hydrazide A mixture of 3-[4-(2,3,5,6-tetramethylbenzyloxy)phenyl]-2-furancarboxylic acid hydrazide (compound of Reference Example 31, 0.50 g) and the compound of Reference Example 63 (0.45 g) in ethyl acetate (10 ml) was heated at reflux overnight while stirring. The thus-precipitated crystals were collected by filtration and recrystallized from methanol/ethyl acetate, thereby giving 0.56 g of the desired compound. Melting point: 183-186° C.

$^1$H-NMR (DMSO-$d_6$, δ): 2.18 (s, 3H), 2.20 (s, 3H), 5.09 (s, 2H), 6.96 (d, J=1.8 Hz, 1H), 6.99 (s, 1H), 7.07 (d, J=8.8 Hz, 2H), 7.12 (d, J=8.8 Hz, 1H), 7.76 (d, J=8.8 Hz, 2H), 7.94 (d,

J=1.8 Hz, 1H), 8.04 (dd, J=2.2, 8.8 Hz, 1H), 8.17 (d, J=2.2 Hz, 1H), 10.32 (s, 1H), 10.37 (s, 1H), 11.88 (br s, 1H)

EXAMPLE 16

Preparation of 3-(4-phenoxyphenyl)-2-furancarboxylic acid 2-(3-cyano-4-hydroxybenzoyl)hydrazide A reaction and treatment was carried out in the same manner as in Example 2 except that the compound of Reference Example 18 used in Example 2 was replaced with 3-(4-phenoxyphenyl)-2-furancarboxylic acid hydrazide (compound of Reference Example 78(1), 0.58 g), thereby giving 0.21 g of the desired compound. Melting point: 199-200° C. (Recrystallized from ethyl acetate/hexane)

EXAMPLE 17

Preparation of 3-(4-benzyloxyphenyl)-2-furancarboxylic acid 2-(3-cyano-4-hydroxybenzoyl)hydrazide A mixture of 3-(4-benzyloxyphenyl)-2-furancarboxylic acid hydrazide (compound of Reference Example 79, 0.44 g) and the compound of Reference Example 63 (0.50 g) in ethyl acetate (10 ml) was heated at reflux overnight while stirring. Water was added to the reaction solution, and the thus-precipitated crystals were collected by filtration and recrystallized from ethyl acetate, thereby giving 0.29 g of the desired compound. Melting point: 208-209° C.
$^1$H-NMR (DMSO-$d_6$, δ): 5.13 (s, 2H), 6.94 (d, J=1.8 Hz, 1H), 7.01 (d, J=8.8 Hz, 2H), 7.11 (d, J=8.6 Hz, 1H), 7.30-7.48 (m, 5H), 7.73 (d, J=8.8 Hz, 2H), 7.91 (d, J=1.8 Hz, 1H), 8.02 (dd, J=2.0, 9.0 Hz, 1H), 8.15 (d, J=2.0 Hz, 1H), 10.30 (s, 1H), 10.35 (s, 1H), 11.87 (br s, 1H)

EXAMPLE 18

Preparation of 3,4-diphenyl-2-furancarboxylic acid 2-(3-cyano-4-hydroxybenzoyl)hydrazide A mixture of 3,4-diphenyl-2-furancarboxylic acid hydrazide (compound of Reference Example 32, 5.2 g) and the compound of Reference Example 63 (6.1 g) in ethyl acetate (10 ml) was heated at reflux overnight while stirring. The thus-precipitated crystals were collected by filtration and recrystallized from ethyl acetate/diisopropyl ether, thereby giving 5.1 g of the desired compound. Melting point: 178-179° C.
$^1$H-NMR (DMSO-$d_6$, δ): 7.06-7.14 (m, 2H), 7.18-7.33 (m, 11H), 8.00 (dd, J=2.2, 8.8 Hz, 1H), 8.13 (d, J=2.2 Hz, 1H), 8.22 (s, 1H), 10.34 (s, 1H), 10.38(s, 1H), 11.86 (br s, 1H)

EXAMPLE 19

Preparation of 3,4-diphenyl-2-furancarboxylic acid 2-(4-hydroxy-3-nitrobenzoyl)hydrazide A mixture composed of the compound of Reference Example 32 (2.8 g) and 4-hydroxy-3-nitrobenzoic acid pentafluorophenyl ester (compound of Reference Example 64, 3.5 g) in ethyl acetate (15 ml) was heated at reflux overnight while stirring. The thus-precipitated crystals were collected by filtration and recrystallized from ethanol/ethyl acetate, thereby giving 3.2 g of the desired compound. Melting point: 214-217° C.
$^1$H-NMR (DMSO-$d_6$, δ): 7.09-7.14 (m, 2H), 7.19-7.33 (m, 9H), 8.04 (dd, J=2.1, 8.8 Hz, 1H), 8.22 (s, 1H), 8.44 (d, J=2.1 Hz, 1H), 10.41 (s, 1H), 10.49 (s, 1H), 11.75 (br s, 1H)

EXAMPLE 20

Preparation of 3-[3-(2,3,5,6-tetramethylbenzyloxy)phenyl]-2-furancarboxylic acid 2-(4-hydroxy-3-nitrobenzoyl)hydrazide A mixture of 3-[3-(2,3,5,6-tetramethylbenzyloxy)phenyl]-2-furancarboxylic acid hydrazide (compound of Reference Example 3, 0.36 g) and the compound of Reference Example 64 (0.35 g) in ethyl acetate (15 ml) was heated at reflux overnight while stirring. The reaction solution was diluted with ethyl acetate, washed with water, and dried over MgSO$_4$. The solvent was evaporated under reduced pressure, and the residue was purified by silica gel column chromatography (eluent: 0%→50% ethyl acetate/hexane gradient) and recrystallized from ethyl acetate/hexane, thereby giving 0.25 g of the desired compound. Melting point: 140-142° C.
$^1$H-NMR (DMSO-$d_6$, δ): 2.17 (s, 6H), 2.19 (s, 6H), 5.08 (s, 2H), 6.98 (s, 1H), 7.03 (d, J=1.8 Hz, 1H), 7.03-7.07 (m, 1H), 7.22 (d, J=8.7 Hz, 1H), 7.30-7.37 (m, 2H), 7.47-7.52 (m, 1H), 7.96 (d, J=1.8 Hz, 1H), 8.05 (dd, J=2.2, 8.7 Hz, 1H), 8.46 (d, J=2.2 Hz, 1H), 10.40 (s,1H), 10.54 (s, 1H), 11.75 (br s, 1H)

EXAMPLE 21

Preparation of 3,4-diphenyl-2-furancarboxylic acid 2-(3-furoyl)hydrazide

To a mixture of the compound of Reference Example 32 (0.56 g), ethyldiisopropylamine (0.78 ml) and dichloromethane (10 ml) was added 3-furancarboxylic acid chloride (0.45 ml) dropwise at 0° C., and the mixture was then stirred overnight at 25° C. The reaction solution was diluted with chloroform, successively washed with saturated aqueous sodium hydrogencarbonate solution, 1 M hydrochloric acid, water and saturated brine, and then dried over MgSO$_4$. The solvent was evaporated under reduced pressure, and the residue was purified by silica gel column chromatography (eluent: methanol/chloroform=1/50), thereby giving 0.43 g of the desired compound. Melting point: 180-183° C. (Recrystallized from ethyl acetate/diisopropyl ether)

EXAMPLES 22 and 23

Reactions and treatments were carried out in the same manner as in Example 21 except that the 3-furancarboxylic acid chloride used in Example 21 was replaced with the appropriate carboxylic acid chlorides to give the following compounds:
3,4-Diphenyl-2-furancarboxylic acid 2-(2-thenoyl)hydrazide (melting point: 132-135° C., recrystallized from ethyl acetate/diisopropyl ether, Example 22), and
3,4-Diphenyl-2-furancarboxylic acid 2-nicotinoyl hydrazide (melting point: 182-185° C., recrystallized from ethyl acetate/diisopropyl ether, Example 23)

EXAMPLE 24

Preparation of 3,4-diphenyl-2-furancarboxylic acid 2-(3-thenoyl)hydrazide

Triethylamine (0.55 ml) was added dropwise to a mixture of the compound of Reference Example 32 (0.56 g), 3-thiophenecarboxylic acid (0.26 g), BOP reagent (0.88 g) and DMF (10 ml) at 0° C., and the mixture was stirred overnight at 25° C. After water was added, the reaction solution was diluted with ethyl acetate. The organic layer was then successively washed with saturated aqueous sodium hydrogencarbonate solution, 20% aqueous citric acid solution and saturated brine, and dried over $MgSO_4$. The solvent was evaporated under reduced pressure, and the residue was purified by silica gel column chromatography (eluent: methanol/chloroform=1/10), thereby giving 0.70 g of the desired compound. Melting point: 195-197° C. (Recrystallized from ethyl acetate/diisopropyl ether)

EXAMPLES 25-28

Reactions and treatments were carried out in the same manner as in Example 24 except that the 3-thiophenecarboxylic acid used in Example 24 was replaced with the appropriate carboxylic acid compounds, thereby giving the following compounds:

3,4-Diphenyl-2-furancarboxylic acid 2-(isonicotinoyl)hydrazide, melting point: 115-120° C. (recrystallized from ethyl acetate/diisopropyl ether, Example 25);

3,4-Diphenyl-2-furancarboxylic acid 2-(2-pyridinecarbonyl)hydrazide, melting point: 190-192° C. (recrystallized from ethyl acetate/diisopropyl ether, Example 26);

3,4-Diphenyl-2-furancarboxylic acid 2-(3-pyrrolecarbonyl)hydrazide, HPLC retention time: 7.02 minutes (Example 27); and 3,4-Diphenyl-2-furancarboxylic acid 2-(5-indolecarbonyl)hydrazide, HPLC retention time: 9.68 minutes (Example 28).

EXAMPLE 29

Preparation of 3,4-diphenyl-2-furancarboxylic acid 2-(2-nitro-4-thenoyl)hydrazide Ethyldiisopropylamine (0.70 ml) was added dropwise to a mixture of the compound of Reference Example 32 (0.56 g), 2-nitro-4-thiophenecarboxylic acid (0.34 g), PyBOP reagent (1.41 g) and DMF (10 ml) at 0° C., and the mixture was stirred overnight at 25° C. After water was added, the reaction solution was diluted with ethyl acetate. The organic layer was washed with saturated aqueous sodium hydrogencarbonate solution and 1 M hydrochloric acid, and dried over $MgSO_4$. The solvent was evaporated under reduced pressure, and the residue was purified by silica gel column chromatography (eluent: 0%→80% ethyl acetate/hexane gradient), thereby giving 0.26 g of the desired compound. Melting point: 170-172° C. (Recrystallized from isopropyl alcohol)

EXAMPLE 30

Preparation of 3,4-diphenyl-2-furancarboxylic acid 2-(4-hydroxy-3-iodobenzoyl)hydrazide A reaction and treatment was carried out in the same manner as in Example 29 except that the 2-nitro-4-thiophenecarboxylic acid used in Example 29 was replaced with 4-hydroxy-3-iodobenzoic acid, thereby giving the desired compound. Melting point: 171-174° C. (Recrystallized from ethyl acetate/hexane)

$^1$H-NMR (DMSO-$d_6$, δ): 6.94 (d, J=8.4 Hz, 1H), 6.80-7.14 (m, 2H), 7.19-7.34 (m, 8H), 7.75 (dd, J=2.0, 8.4 Hz, 2H), 8.22 (s, 1H), 8.23 (d, J=2.0 Hz, 1H), 10.24 (s, 1H), 10.31 (s, 1H), 11.87 (br s, 1H)

EXAMPLE 31

Preparation of 3,4-diphenyl-2-furancarboxylic acid 2-(3-fluoro-4-methoxybenzoyl)hydrazide Triethylamine (1.12 ml) was added dropwise to a mixture of the compound of Reference Example 32 (1.11 g), 3-fluoro-4-methoxybenzoic acid (0.68 g), BOP reagent (1.77 g) and DMF (10 ml) at 0° C., and the mixture was stirred at 25° C. overnight. The reaction solution was mixed with water. The thus-precipitated crystals were filtered, washed with water, and purified by silica gel column chromatography (eluent: 0%→5% methanol/chloroform gradient), thereby giving 1.38 g of the desired compound. Melting point: 110-112° C. (Recrystallized from ethyl acetate).

EXAMPLE 32

Preparation of 3,4-diphenyl-2-furancarboxylic acid 2-(3-fluoro-4-hydroxybenzoyl)hydrazide Boron tribromide (1 M dichloromethane solution: 6.00 ml) was added dropwise to a mixture of the compound of Example 31 (0.86 g) and dichloromethane (20 ml) at 0° C., and the mixture was stirred at 25° C. overnight. Water was added to the reaction solution. The thus-precipitated crystals were collected by filtration, purified by silica gel column chromatography (eluent: ethyl acetate/hexane=1/3), and recrystallized from ethanol, thereby giving 0.64 g of the desired compound. Melting point: 243-245° C.

EXAMPLES 33-36

Reactions and treatments were carried out in the same manner as in Example 31 except that the 3-fluoro-4-methoxybenzoic acid used in Example 31 was replaced with the appropriate 4-methoxybenzoic acid derivatives, thereby giving the following compounds:

3,4-Diphenyl-2-furancarboxylic acid 2-(3-chloro-4-methoxybenzoyl)hydrazide, melting point: 203-207° C. (recrystallized from methanol/chloroform, Example 33);

3,4-Diphenyl-2-furancarboxylic acid 2-(3-bromo-4-methoxybenzoyl)hydrazide, melting point: 243-245° C. (recrystallized from ethanol, Example 34);

3,4-Diphenyl-2-furancarboxylic acid 2-(4-methoxybenzoyl)hydrazide, melting point: 210-213° C. (recrystallized from DMF/water, Example 35); and 3,4-Diphenyl-2-furancarboxylic acid 2-(4-methoxy-3-trifluoromethylbenzoyl)hydrazide, melting point: 197-199° C. (recrystallized from ethyl acetate/hexane, Example 36).

EXAMPLES 37-39

Reactions and treatments were carried out in the same manner as in Example 32 except that the compound of Example 31 used in Example 32 was replaced with the compounds of Examples 33, 34 and 35, respectively, thereby giving the following compounds:

3,4-Diphenyl-2-furancarboxylic acid 2-(3-chloro-4-hydroxybenzoyl)hydrazide, melting point: 197-199° C. (recrystallized from ethyl acetate/hexane, Example 37);

3,4-Diphenyl-2-furancarboxylic acid 2-(3-bromo-4-hydroxybenzoyl)hydrazide, melting point: 208-210° C. (recrystallized from ethanol, Example 38); and 3,4-Diphenyl-2-furancarboxylic acid 2-(4-hydroxybenzoyl)hydrazide, melting point: 267-268° C. (recrystallized from ethanol, Example 39).

EXAMPLE 40

Preparation of 3,4-diphenyl-2-furancarboxylic acid 2-[3-(tert-butoxycarbonylamino)-4-methoxybenzoyl]hydrazide Triethylamine (5.95 ml) was added dropwise to a mixture of 3,4-diphenyl-2-furancarboxylic acid (compound of Reference Example 33, 3.76 g), 3-(tert-butoxycarbonylamino)-4-methoxybenzoic acid hydrazide (compound of Reference Example 65, 4.00 g), BOP reagent (9.43 g) and DMF (40 ml) at 0° C., and the mixture was stirred overnight at 25° C. After adding water thereto, the reaction solution was diluted with chloroform. The organic layer was then successively washed with saturated aqueous sodium hydrogencarbonate solution and saturated brine, and dried over $MgSO_4$. The solvent was evaporated under reduced pressure, and the residue was purified by silica gel column chromatography (eluent: chloroform), thereby giving 6.42 g of the desired compound. Melting point: 137-141° C. (Recrystallized from ethyl acetate/hexane)

EXAMPLES 41

Preparation of 3,4-diphenyl-2-furancarboxylic acid 2-(3-amino-4-methoxybenzoyl)hydrazide Trifluoroacetic acid (8.00 ml) was added dropwise to a mixture of the compound of Example 40 (4.81 g) and dichloromethane (10 ml) at 25° C., and the mixture was stirred overnight. The reaction solution was diluted with chloroform and neutralized with 1 M aqueous sodium hydroxide solution. The thus-precipitated crystals were collected by filtration, thereby giving 3.85 g of the desired compound. HPLC retention time: 3.36 minutes.

EXAMPLE 42

Preparation of 3,4-diphenyl-2-furancarboxylic acid 2-(3-amino-4-hydroxybenzoyl)hydrazide A reaction and treatment was carried out in the same manner as in Example 32 except that the compound of Example 31 used in Example 32 was replaced with the compound of Example 41 (1.00 g), thereby giving 0.93 g of the desired compound. Melting point: 268-270° C. (Recrystallized from methanol)

EXAMPLE 43

Preparation of 3,4-diphenyl-2-furancarboxylic acid 2-(4-hydroxy-3-trifluoromethylbenzoyl)hydrazide A mixture of the compound of Example 36 (0.50 g) and pyridine hydrochloride (5.00 g) was stirred for 0.5 hours at 150° C. in an oil bath. The reaction solution was diluted with ethyl acetate, washed with 1 M hydrochloric acid, and dried over $MgSO_4$. The solvent was evaporated under reduced pressure, and the residue was purified by silica gel column chromatography (eluent: chloroform), thereby giving 0.10 g of the desired compound. Melting point: 142-143° C. (Recrystallized from chloroform).

EXAMPLE 44

Preparation of 3,4-bis(4-chlorophenyl)-2-furancarboxylic acid 2-(3-cyano-4-hydroxybenzoyl)hydrazide A mixture of 3,4-bis(4-chlorophenyl)-2-furancarboxylic acid hydrazide (compound of Reference Example 36, 0.092 g) and the compound of Reference Example 63 (0.11 g) in DMF (5 ml) was stirred overnight at 70° C. The reaction solution was diluted with ethyl acetate, washed with water, and dried over $MgSO_4$. The solvent was evaporated under reduced pressure, and the residue was purified by silica gel column chromatography (eluent: 1:20 methanol/chloroform), and recrystallized from ethyl acetate/hexane, thereby giving 0.054 g of the desired compound. Melting point: 190-191° C. (Recrystallized from ethyl acetate)

EXAMPLES 45 AND 46

Reactions and treatments were carried out in the same manner as in Example 44 except that the compound of Reference Example 36 used in Example 44 was replaced with the compounds of Reference Examples 37 and 38, respectively, thereby giving the following compounds:

3,4-Bis(4-fluorophenyl)-2-furancarboxylic acid 2-(3-cyano-4-hydroxybenzoyl)hydrazide, melting point: 243-245° C. (recrystallized from ethyl acetate, Example 45); and 3,4-Bis(4-bromophenyl)-2-furancarboxylic acid 2-(3-cyano-4-hydroxybenzoyl)hydrazide, melting point: 188-190° C. (recrystallized from ethyl acetate/hexane, Example 46).

EXAMPLE 47

Preparation of 4-phenyl-3-vinyl-2-furancarboxylic acid 2-(3-cyano-4-hydroxybenzoyl)hydrazide A mixture of 4-phenyl-3-vinyl-2-furancarboxylic acid hydrazide (compound of Reference Example 39, 0.20 g) and the compound of Reference Example 63 (0.32 g) in DMF (5 ml) was stirred at 70° C. for 3 hours. The reaction solution was diluted with ethyl acetate, washed with water, and dried over $MgSO_4$. The solvent was evaporated under reduced pressure, and the residue was recrystallized from ethyl acetate, thereby giving 0.17 g of the desired compound. Melting point: 170-174° C.

EXAMPLES 48-50

Reactions and treatments were carried out in the same manner as in Example 47 except that the 4-phenyl-3-vinyl-2-furancarboxylic acid hydrazide used in Example 47 was replaced with appropriate 2-furancarboxylic acid hydrazide compounds, thereby giving the following compounds:

3-Phenyl-4-vinyl-2-furancarboxylic acid 2-(3-cyano-4-hydroxybenzoyl)hydrazide, melting point: 175-177° C. (recrystallized from ethyl acetate, Example 48);

3-Ethyl-4-phenyl-2-furancarboxylic acid 2-(3-cyano-4-hydroxybenzoyl)hydrazide, melting point: 190-192° C. (recrystallized from ethyl acetate/hexane, Example 49); and 4-Ethyl-3-phenyl-2-furancarboxylic acid 2-(3-cyano-4-hydroxybenzoyl)hydrazide, melting point: 186-188° C. (recrystallized from ethyl acetate/hexane, Example 50).

EXAMPLE 51

Preparation of 4-hydroxymethyl-3-phenyl-2-furancarboxylic acid 2-(3-cyano-4-hydroxybenzoyl)hydrazide (1) A mixture of 4-(tert-butyldimethylsilyloxymethyl)-3-phenyl-2-furancarboxylic-acid hydrazide (compound of Reference Example 42, 0.17 g) and the compound of Reference Example 63 (0.17 g) in DMF (5 ml) was stirred at 70° C. for 3 hours. The reaction solution was diluted with diethyl ether, washed with water, and dried over MgSO$_4$. The solvent was evaporated under reduced pressure, thereby giving 0.17 g of 4-(tert-butyldimethylsilyloxymethyl)-3-phenyl-2-furancarboxylic acid 2-(3-cyano-4-hydroxybenzoyl)hydrazide.

(2) Tetrabutylammonium fluoride (1 M THF solution: 3.5 ml) was added to a THF (10 ml) solution of the tert-butyldimethylsilyloxymethyl compound obtained above at 25° C., and stirred for 1 hour. Chloroform and water were added to the reaction solution, the organic layer was dried over MgSO$_4$, and the solvent was evaporated under reduced pressure. The residue was purified by silica gel column chromatography (eluent: methanol/chloroform=1/25), thereby giving 0.070 g of the desired compound. HPLC retention time: 2.08 minutes.

EXAMPLE 52

Preparation of 3-hydroxymethyl-4-phenyl-2-furancarboxylic acid 2-(3-cyano-4-hydroxybenzoyl)hydrazide A reaction and treatment was carried out in the same manner as in Example 51 except that the 4-(tert-butyldimethylsilyloxymethyl)-3-phenyl-2-furancarboxylic acid used in Example 51 was replaced with 3-(tert-butyldimethylsilyloxymethyl)-4-phenyl-2-furancarboxylic acid hydrazide, thereby giving the desired compound. HPLC retention time: 2.76 minutes.

EXAMPLE 53

Preparation of 4-(phenylaminocarbonyloxymethyl)-3-phenyl-2-furancarboxylic acid 2-(3-cyano-4-hydroxybenzoyl)hydrazide A mixture of 4-(phenylaminocarbonyloxymethyl)-3-phenyl-2-furancarboxylic acid hydrazide (compound of Reference Example 44), the compound of Reference Example 63 (0.50 g) and DMF (5 ml) was stirred at 70° C. for 3 hours. The reaction solution was diluted with ethyl acetate, washed with water, and dried over MgSO$_4$. The solvent was evaporated under reduced pressure, and the residue was purified by silica gel column chromatography (eluent: 0%→4% methanol/chloroform gradient), thereby giving 0.030 g of the desired compound. HPLC retention time: 6.28 minutes.

EXAMPLES 54-59

Reactions and treatments were carried out in the same manner as in Example 53 using the compound of Reference Example 63 in conjunction with the compounds of Reference Example 45, 46, 47, 48, 49 or 50, respectively, thereby giving the following compounds:

4-(Phenethylaminocarbonyloxymethyl)-3-phenyl-2-furancarboxylic acid 2-(3-cyano-4-hydroxybenzoyl)hydrazide, HPLC retention time: 6.18 minutes (Example 54);

3-(Phenylaminocarbonyloxymethyl)-4-phenyl-2-furancarboxylic acid 2-(3-cyano-4-hydroxybenzoyl)hydrazide, HPLC retention time: 7.64 minutes (Example 55);

4-Benzyloxymethyl-3-phenyl-2-furancarboxylic acid 2-(3-cyano-4-hydroxybenzoyl)hydrazide, HPLC retention time: 8.20 minutes (Example 56);

3-Phenyl-4-piperidinomethyl-2-furancarboxylic acid 2-(3-cyano-4-hydroxybenzoyl)hydrazide, HPLC retention time: 3.38 minutes (Example 57);

4-Phenyl-3-piperidinomethyl-2-furancarboxylic acid 2-(3-cyano-4-hydroxybenzoyl)hydrazide, HPLC retention time: 1.70 minutes (Example 58); and 3-Phenyl-4-(4-phenyl-1-butenyl)-2-furancarboxylic acid 2-(3-cyano-4-hydroxybenzoyl)hydrazide, HPLC retention time: 25.99 minutes (Example 59).

EXAMPLE 60

Preparation of 3-(2-thienyl)-2-furancarboxylic acid 2-(3-cyano-4-hydroxybenzoyl)hydrazide A reaction and treatment was carried out in the same manner as in Example 1(b) using the compound of Reference Example 13 (0.62 g) and the compound of Reference Example 63 (0.99 g). The thus prepared was recrystallized from methanol/chloroform, thereby giving 0.22 g of the desired compound. Melting point: 258-259° C.

EXAMPLE 61

Preparation of 3-phenyl-2-furancarboxylic acid 2-(3-cyano-4-hydroxybenzoyl)hydrazide A mixture of the compound of Reference Example 14 (0.40 g) and the compound of Reference Example 63 (0.66 g) in ethyl acetate (10 ml) was heated at reflux while stirring overnight. The thus-precipitated crystals were collected by filtration and recrystallized from methanol/ethyl acetate, thereby giving 0.28 g of the desired compound. Melting point: 216-217° C.

$^1$H-NMR (DMSO-d$_6$, δ): 6.96 (d, J=1.5 Hz, 1H), 7.11 (d, J=8.8 Hz, 1H), 7.29-7.42 (m, 3H), 7.73 (d, J=6.8 Hz, 2H), 7.95 (d, J=1.5 Hz, 1H), 8.02 (dd, J=2.0, 8.8 Hz, 1H), 8.15 (d, J=2.0 Hz, 1H), 10.36 (s, 2H), 11.88 (br s, 1H)

EXAMPLE 62

Preparation of 4-(4-methoxyphenyl)-3-phenyl-2-furancarboxylic acid 2-(3-cyano-4-hydroxybenzoyl) hydrazide A mixture of 4-(4-methoxyphenyl)-3-phenyl-2-furancarboxylic acid hydrazide (compound of Reference Example 10, 0.31 g) and the compound of Reference Example 63 (0.33 g) in ethyl acetate (10 ml) was heated at reflux while stirring overnight. The thus-precipitated crystals were collected by filtration and recrystallized from ethyl acetate/diisopropyl ether, thereby giving 0.31 g of the desired compound. Melting point: 146-148° C.

$^1$H-NMR (DMSO-d$_6$, δ): 3.39 (s, 3H), 6.85-6.96 (m, 2H), 7.70-7.34 (m, 8H), 8.02 (dd, J=2.4, 8.8 Hz, 1H), 8.02 (s, 1H), 8.15 (d, J=8.8 Hz, 1H), 10.34 (s, 1H), 10.36 (s, 1H), 11.86 (br s, 1H)

EXAMPLE 63

Preparation of 3-phenyl-4-(4-pyridyl)-2-furancarboxylic acid 2-(3-cyano-4-hydroxybenzoyl)hydrazide A mixture of 3-phenyl-4-(4-pyridyl)-2-furancarboxylic acid hydrazide (compound of Reference Example 11, 0.28 g) and the compound of Reference Example 63 (0.33 g in ethyl acetate (10 ml) was heated at reflux while stirring overnight. The thus-precipitated crystals were collected by filtration and recrystallized from ethyl acetate, thereby giving 0.02 g of the desired compound. Melting point: 179-181° C.

EXAMPLE 64

Preparation of 4-phenyl-2-furancarboxylic acid 2-(3-cyano-4-hydroxybenzoyl)hydrazide A mixture of the compound of Reference Example 58 (0.12 g) and the compound of Reference Example 63 (0.19 g) in ethyl acetate (10 ml) was heated at reflux while stirring overnight. The thus-precipitated crystals were collected by filtration, thereby giving 0.06 g of the desired compound. HPLC retention time: 3.31 minutes.

EXAMPLES 65-67

Reactions and treatments were carried out in the same manner as in Example 64 except that the compound of Reference Example 58 used in Example 64 was replaced with the compounds of Reference Example 59, 60 or 61, respectively, thereby giving the following compounds:

4-(2-Benzyloxyphenyl)-2-furancarboxylic acid 2-(3-cyano-4-hydroxybenzoyl)hydrazide, HPLC retention time: 9.48 minutes (Example 65);

4-(3-Benzyloxyphenyl)-2-furancarboxylic acid 2-(3-cyano-4-hydroxybenzoyl)hydrazide, HPLC retention time: 9.17 minutes (Example 66); and 4-(4-Benzyloxyphenyl)-2-furancarboxylic acid 2-(3-cyano-4-hydroxybenzoyl)hydrazide, HPLC retention time: 9.10 minutes (Example 67).

EXAMPLE 68

Preparation of 3,4-diphenyl-2-furancarboxylic acid 2-(4-benzyloxy-3-methoxybenzoyl)hydrazide A reaction and treatment was carried out in the same manner as in Example 24 except that the 3-thiophenecarboxylic acid used in Example 24 was replaced with 4-benzyloxy-3-methoxybenzoic acid (1.11 g), thereby giving 2.10 g of the desired compound. Melting point: 203-204° C. (Recrystallized from DMF/water)

EXAMPLE 69

Preparation of 3,4-diphenyl-2-furancarboxylic acid 2-(4-hydroxy-3-methoxybenzoyl)hydrazide A mixture of the compound of Example 68 (0.80 g), dioxane (100 ml), methanol (10 ml) and 10% palladium carbon (0.16 g) was hydrogenated at 40° C. with stirred for 6 hours. The reaction solution was filtered, and the filtrate was concentrated under reduced pressure. The residue was purified by silica gel column chromatography (eluent: methanol/chloroform=1/9) and recrystallized from ethanol, thereby giving 0.40 g of the desired compound. Melting point: 216-220° C.

EXAMPLE 70

Preparation of 3,4-diphenyl-2-furancarboxylic acid 2-(4-methoxy-3-methylsulfonylaminobenzoyl)hydrazide Methylsulfonyl chloride (0.28 ml) was added to a mixture of the compound of Example 41 (0.85 g), triethylamine (0.41 ml) and dioxane (30 ml) at 0° C., allowed to be warmed to 25° C. and stirred overnight. The reaction solution was diluted with ethyl acetate, washed with water and dried over $MgSO_4$. The solvent was evaporated under reduced pressure, and the residue was purified by silica gel column chromatography (eluent: chloroform), thereby giving 0.95 g of the desired compound. Melting point: 180-182° C. (Recrystallized from ethyl acetate/hexane).

EXAMPLE 71

Preparation of 3,4-diphenyl-2-furancarboxylic acid 2-(4-hydroxy-3-methylsulfonylaminobenzoyl)hydrazide Boron tribromide (1 M dichloromethane solution; 5.10 ml) was added to a dichloromethane (10 ml) solution of the compound of Example 70 (0.86 g) at 0° C. and stirred at 25° C. for 3 hours. The reaction solution was mixed with 2 M aqueous sodium hydroxide solution, stirred for 0.3 hours, and mixed with 2 M hydrochloric acid and chloroform. The organic layer was washed with saturated brine and dried over $MgSO_4$. The solvent was evaporated under reduced pressure, and the residue was purified by silica gel column chromatography (eluent: 0→15% methanol/chloroform gradient) and recrystallized from isopropyl alcohol, thereby giving 0.29 g of the desired compound. Melting point: 230-231° C.

EXAMPLE 72

Preparation of 3,4-diphenyl-2-furancarboxylic acid 2-(3-acetylamino-4-hydroxybenzoyl)hydrazide Acetyl chloride (0.17 ml) was added to a mixture of the compound of Example 42 (0.83 g), ethyldiisopropylamine (1.05 ml) and dioxane (10 ml) at 0° C., allowed to be warmed to 25° C. and stirred for 9 days. The solvent was evaporated under reduced pressure. The residue was diluted with ethyl acetate and washed with 1 M hydrochloric acid and saturated brine. The organic layer was dried over $MgSO_4$, and the solvent was evaporated under reduced pressure. The residue was purified by silica gel column chromatography (eluent: chloroform) and recrystallized from ethyl acetate/hexane, thereby giving 0.25 g of the desired compound. Melting point: 233-235° C.

EXAMPLE 73

Preparation of 3,4-diphenyl-2-furancarboxylic acid 2-(4-methoxy-3-methylsulfamoylbenzoyl)hydrazide A reaction and treatment was carried out in the same manner as in Example 24 using the compound of Reference Example 32 (0.56 g) and 4-methoxy-3-(N-methylsulfamoyl) benzoic acid (the compound of Reference Example 67, 0.49 g), thereby giving 0.50 g of the desired compound. Melting point: 239-241° C. (Recrystallized from ethyl acetate/hexane)

EXAMPLE 74

Preparation of 3,4-diphenyl-2-furancarboxylic acid 2-(4-hydroxy-3-methylsulfamoylbenzoyl)hydrazide Boron tribromide (1 M dichloromethane solution; 2.37 ml) was added to a dichloromethane (10 ml) solution of the compound of Example 73 (0.40 g) at 0° C., and stirred at 25° C. for 3 hours. The reaction solution was mixed with 2 M aqueous sodium hydroxide solution, stirred for 0.3 hours, and mixed with 2 M hydrochloric acid and chloroform. The organic layer was washed with saturated brine and dried over $MgSO_4$. The solvent was evaporated under reduced pressure, and the residue was purified by silica gel column chromatography (eluent: 0→15% methanol/chloroform gradient) and recrystallized from methanol/ethyl acetate, thereby giving 0.29 g of the desired compound. Melting point: 119-120° C.

EXAMPLES 75-78

Reactions and treatments were carried out in the same manner as in Example 24 using the compound of Reference Example 32 and the appropriate 4-methoxybenzoic acid derivatives, thereby giving the following compounds:

3,4-Diphenyl-2-furancarboxylic acid 2-(3,4-dimethoxybenzoyl)hydrazide, melting point: 181-184° C. (recrystallized from methanol/chloroform, Example 75);

3,4-Diphenyl-2-furancarboxylic acid 2-(2,4-dimethoxybenzoyl)hydrazide, melting point: 240-242° C. (recrystallized from methanol/chloroform, Example 76);

3,4-Diphenyl-2-furancarboxylic acid 2-(3,5-dichloro-4-methoxybenzoyl)hydrazide, melting point: 229-230° C. (recrystallized from ethyl acetate/hexane, Example 77); and 3,4-Diphenyl-2-furancarboxylic acid 2-(4-methoxy-3-phenylbenzoyl)hydrazide (Example 78).

EXAMPLES 79-82

Reactions and treatments were carried out in the same manner as in Example 74 except that the compound of Example 73 used in Example 74 was replaced with the compounds of 75, 76, 77 or 78, respectively, thereby giving the following compounds:

3,4-Diphenyl-2-furancarboxylic acid 2-(3,4-dihydroxybenzoyl)hydrazide, melting point: 242-244° C. (recrystallized from isopropyl alcohol, Example 79);

3,4-Diphenyl-2-furancarboxylic acid 2-(2,4-dihydroxybenzoyl)hydrazide, melting point: 285-288° C. (recrystallized from methanol, Example 80);

3,4-Diphenyl-2-furancarboxylic acid 2-(3,5-dichloro-4-hydroxybenzoyl)hydrazide, melting point: 261-263° C. (recrystallized from ethanol, Example 81); and 3,4-Diphenyl-2-furancarboxylic acid 2-(4-hydroxy-3-phenylbenzoyl)hydrazide, melting point: 217-218° C. (recrystallized from isopropyl alcohol, Example 82).

EXAMPLE 83

Preparation of 3,4-diphenyl-2-furancarboxylic acid 2-(3-tert-butyl-4-hydroxybenzoyl)hydrazide Triethylamine (0.28 ml) was added dropwise to a mixture of the compound of Reference Example 32 (0.28 g), 3-tert-butyl-4-hydroxybenzoic acid (0.19 g), PyBOP reagent (0.52 g) and DMF (10 ml) at 0° C., and stirred overnight at 25° C. After water was added, the reaction solution was diluted with ethyl acetate. The organic layer was washed with saturated brine and dried over $MgSO_4$. The solvent was evaporated under reduced pressure, and the residue was purified by silica gel column chromatography (eluent: 0→50% ethyl acetate/hexane gradient), thereby giving 0.08 g of the desired compound. Melting point: 244-247° C. (Recrystallized from ethyl acetate/hexane)

EXAMPLE 84

Preparation of 3,4-bis(4-methoxyphenyl)-2-furancarboxylic acid (3-furoyl)hydrazide Triethylamine (1.67 ml) was added dropwise to a mixture of the compound of Reference Example 34 (1.29 g), 3-furancarboxylic acid hydrazide (compound of Reference Example 51, 0.80 g), BOP reagent (2.65 g) and DMF (10 ml) at 0° C., and stirred overnight at 25° C. After water was added, the reaction solution was diluted with ethyl acetate. The organic layer was washed with saturated brine and dried over $MgSO_4$. The solvent was evaporated under reduced pressure, and the residue was purified by silica gel column chromatography (eluent: methanol/chloroform=1/9), thereby giving 1.27 g of the desired compound. Melting point: 100-102° C. (Recrystallized from ethyl acetate/hexane)

EXAMPLES 85-90

Reactions and treatments were carried out in the same manner as in Example 84 except that the compound of Reference Example 34 used in Example 84 was replaced with the appropriate 2-furancarboxylic acid compounds, thereby giving the following compounds:

5-Bromo-3,4-diphenyl-2-furancarboxylic acid (3-furoyl) hydrazide, melting point: 110-115° C. (recrystallized from ethyl acetate/hexane, Example 85);

5-Methoxy-3,4-diphenyl-2-furancarboxylic acid (3-furoyl)hydrazide, melting point: 189-191° C. (recrystallized from ethyl acetate/hexane, Example 86);

3,4,5-Triphenyl-2-furancarboxylic acid (3-furoyl)hydrazide, melting point: 210-212° C. (recrystallized from ethyl acetate, Example 87);

5-Bromo-3-phenyl-2-furancarboxylic acid (3-furoyl)hydrazide, melting point: 190-191° C. (recrystallized from ethyl acetate/diisopropyl ether, Example 88);

3,5-Diphenyl-2-furancarboxylic acid (3-furoyl)hydrazide, melting point: 213-214° C. (recrystallized from ethanol, Example 89); and 3-(2-Furyl)-2-furancarboxylic acid (3-furoyl)hydrazide, melting point: 210-213° C. (recrystallized from ethanol, Example 90).

EXAMPLE 91

Preparation of 3,4-bis(4-methylphenyl)-2-furancarboxylic acid (3-furoyl)hydrazide Triethylamine (0.096 ml) was added dropwise to a mixture of the compound of Reference Example 35 (0.10 g), the compound of Reference Example 51 (0.042 g), BOP reagent (0.15 g) and DMF (10 ml) at 0° C., and stirred overnight at 25° C. After water was added to the reaction solution, the thus-precipitated crystals were filtered and purified by silica gel column chromatography (eluent: methanol/chloroform=1/9), thereby giving 0.05 g of the desired compound. Melting point: 180-181° C. (Recrystallized from ethanol)

EXAMPLE 92

Preparation of 3,4-bis(4-hydroxyphenyl)-2-furancarboxylic acid (3-furoyl)hydrazide Boron tribromide (1 M dichloromethane solution: 12.00 ml) was added dropwise to a dichloromethane (5 ml) solution of the compound of Example 84 (0.86 g) at 0° C., and stirred overnight at 25° C. After water was added to the reaction solution, the thus-precipitated crystals were filtered and purified by silica gel column chromatography (eluent: methanol/chloroform=1/9), thereby giving 0.40 g of the desired compound. Melting point: 168-172° C. (Recrystallized from ethyl acetate)

EXAMPLE 93

Preparation of 5-hydroxy-3,4-diphenyl-2-furancarboxylic acid (3-furoyl)hydrazide A reaction and treatment was carried out in the same manner as in Example 32 using the compound of Example 86 (0.44 g), boron tribromide (1 M dichloromethane solution, 3.27 ml) and dichloromethane (5 ml). The compound thus prepared was recrystallized from ethyl acetate/hexane, thereby giving 0.13 g of the desired compound. Melting point: 195-198° C.

EXAMPLE 94

Preparation of 3,4-diphenyl-2-furancarboxylic acid 2-(4-acetoxy-3-cyanobenzoyl)hydrazide Acetyl chloride (0.080 ml) was added to a mixture of the compound of Example 18 (0.42 g), 4-dimethylaminopyridine (0.013 g), triethylamine (0.17 ml) and dichloromethane (5 ml) at 0° C., and stirred for 0.5 hours at this temperature. The reaction solution was diluted with ethyl acetate, washed with water and dried over MgSO$_4$. The solvent was evaporated under reduced pressure, and the residue was recrystallized from ethyl acetate/hexane, thereby giving 0.26 g of the desired compound. Melting point: 131-133° C.

EXAMPLE 95

Preparation of 3,4-diphenyl-2-furancarboxylic acid 2-(4-benzoyloxy-3-cyanobenzoyl)hydrazide A reaction and treatment was carried out in the same manner as in Example 94 except that the acetyl chloride used in Example 94 was replaced with benzoyl chloride (0.38 ml). The compound thus obtained was purified by silica gel column chromatography (eluent: 0%→50% ethyl acetate/hexane gradient), thereby giving 1.10 g of the desired compound. Melting point: 163-167° C. (Recrystallized from ethyl acetate/hexane)

EXAMPLE 96

Preparation of 3,4-diphenyl-2-furancarboxylic acid 2-(3-cyano-4-pivaloyloxybenzoyl)hydrazide A reaction and treatment was carried out in the same manner as in Example 94 except that the acetyl chloride used in Example 94 was replaced with pivaloyl chloride (0.41 ml). The compound thus obtained was purified by silica gel column chromatography (eluent: 0%→70% ethyl acetate/hexane gradient), thereby giving 0.93 g of the desired compound. Melting point: 152-154° C. (recrystallized from ethyl acetate/hexane).

EXAMPLE 97

Preparation of 3,4-diphenyl-2-furancarboxylic acid 2-[4-(2-hydroxyethoxy)-3-cyanobenzoyl]hydrazide A mixture of the compound of Example 18 (0.42 g), ethylene carbonate (0.088 g), tetraethylammonium iodide (0.026 g) and DMF (10 ml) was stirred at 100° C. for 2 hours. The solvent was evaporated under reduced pressure, and the residue was purified by silica gel column chromatography (eluent: 50%→90% ethyl acetate/hexane gradient), thereby giving 0.26 g of the desired compound. HPLC retention time: 6.31 minutes.

EXAMPLE 98

Preparation of 4-phenyl-3-[3-(2,3,5,6-tetramethylbenzyloxy)phenyl]-2-furancarboxylic acid 2-(3-cyano-4-hydroxybenzoyl)hydrazide A reaction and treatment was carried out in the same manner as in Example 53 using 3-[3-(2,3,5,6-tetramethylbenzyloxy)phenyl]-4-phenyl-2-furancarboxylic acid hydrazide (compound of Reference Example 69, 0.21 g) and the compound of Reference Example 63 (0.19 g), thereby giving 0.08 g of the desired compound. Melting point: 207-209° C. (Recrystallized from ethyl acetate/hexane)

$^1$H-NMR (DMSO-d$_6$, δ): 2.08 (s, 6H), 2.16 (s, 6H), 4.87 (s, 2H), 6.83-6.90 (m, 2H), 6.90-7.00 (m, 2H), 7.09 (d, J=8.9 Hz, 1H), 7.13-7.19 (m, 2H), 7.25 (d, J=8.6 Hz, 1H), 7.25-7.35 (m, 3H), 7.99 (dd, J=2.0, 8.9 Hz, 1H), 8.12 (d, J=2.0 Hz, 1H), 8.20 (s, 1H), 10.36 (s, 2H), 11.86 (br s, 1H)

EXAMPLE 99

Preparation of 3-phenyl-4-[3-(2,3,5,6-tetramethylbenzyloxy)phenyl]-2-furancarboxylic acid 2-(3-cyano-4-hydroxybenzoyl)hydrazide A reaction and treatment was carried out in the same manner as in Example 53 using 3-phenyl-4-[3-(2,3,5,6-tetramethylbenzyloxy)phenyl]-2-furancarboxylic acid hydrazide (compound of Reference Example 69, 0.08 g) and the compound of Reference Example 63 (0.07 g), thereby giving 0.045 g of the desired compound. Melting point: 242-247° C. (Recrystallized from ethyl acetate)

$^1$H-NMR (DMSO-d$_6$, δ): 2.08 (s, 6H), 2.18 (s, 6H), 4.77 (s, 2H), 6.72 (s, 1H), 6.78 (d, J=7.7 Hz, 1H), 6.88-6.92 (m, 1H), 6.96 (s, 1H), 7.09 (d, J=8.8 Hz, 1H), 7.19 (d, J=7.9 Hz, 1H), 7.22-7.36 (m, 5H), 7.45-7.49 (m, 1H), 7.95 (d, J=1.8 Hz, 1H), 7.99 (dd, J=2.2, 8.8 Hz, 1H), 8.12 (d, J=2.2 Hz, 1H), 8.28 (s, 1H), 10.33 (s, 1H), 10.37 (s, 1H), 11.85 (br s, 1H)

EXAMPLE 100

Preparation of 4-phenyl-3-[3-(2,3,5,6-tetramethylbenzyloxy)phenyl]-2-furancarboxylic acid 2-(4-hydroxy-3-nitrobenzoyl)hydrazide A reaction and treatment was carried out in the same manner as in Example 53 using 4-phenyl-3-[3-(2,3,5,6-tetramethylbenzyloxy)phenyl]-2-furancarboxylic acid hydrazide (1.00 g) and the compound of Reference Example 64 (0.84 g), thereby giving 0.08 g of the desired compound. Melting point: 130-132° C. (Recrystallized from acetonitrile)

$^1$H-NMR (DMSO-$d_6$, δ): 2.08 (s, 6H), 2.16 (s, 6H), 4.88 (s, 2H), 6.85-6.91 (m, 2H), 6.93-7.00 (m, 2H), 7.14-7.32 (m, 7H), 8.04 (dd, J=2.0, 8.7 Hz, 1H), 8.21 (s, 1H), 8.44 (d, J=2.0 Hz, 1H), 10.40 (s, 1H), 10.52 (s, 1H), 11.75 (br s, 1H)

EXAMPLE 101

Preparation of 3-(3-benzyloxyphenyl)-2-furancarboxylic acid 2-(4-hydroxy-3-nitrobenzoyl)hydrazide A reaction and treatment was carried out in the same manner as in Example 53 using the compound of Reference Example 20 (0.80 g) and the compound of Reference Example 64 (0.91 g), thereby giving 0.80 g of the desired compound. Melting point: 171-173° C. (Recrystallized from chloroform)

$^1$H-NMR (DMSO-$d_6$, δ): 5.11 (s, 2H), 6.95-7.02 (m, 2H), 7.23 (d, J=8.7 Hz, 1H), 7.26-7.50 (m, 9H), 7.95 (d, J=1.8 Hz, 1H), 8.06 (dd, J=2.2, 8.7 Hz, 1H), 8.46 (d, J=2.2 Hz, 1H), 10.39 (s, 1H), 10.54 (s, 1H), 11.75 (br s, 1H)

EXAMPLE 102

Preparation of 3-[3-(4-pyridylmethyloxy)phenyl]-2-furancarboxylic acid 2-(3-cyano-4-hydroxybenzoyl)hydrazide A mixture of 3-[3-(4-pyridylmethyloxy)phenyl]-2-furancarboxylic acid hydrazide (compound of Reference Example 70; 0.77 g), the compound of Reference Example 63 (0.82 g) and DMF (4 ml) was stirred overnight at 70° C. The reaction solution was diluted with ethyl acetate and washed with water. The thus-precipitated crystals were filtered and dissolved in 30% methanolic hydrogen chloride. After distilling off the solvent under reduced pressure, acetone was added to the residue. The solid matter thus prepared was collected by filtration and washed with ethanol, thereby giving 0.40 g of the desired hydrochloride. HPLC retention time: 1.50 minutes.

$^1$H-NMR (DMSO-$d_6$, δ): 5.46 (s, 2H), 6.99 (d, J=1.7 Hz, 1H), 7.00-7.05 (m, 1H), 7.16 (d, J=8.7 Hz, 1H), 7.30-7.40 (m, 2H), 7.53 (s, 1H), 7.94-8.00 (m, 3H), 8.03 (dd, J=2.0, 8.7 Hz, 1H), 8.16 (d, J=2.0 Hz, 1H), 8.84 (d, J=6.4 Hz, 2H), 10.38 (s, 1H), 10.41 (s, 1H), 11.97 (br s, 1H)

EXAMPLES 103-109

Reactions and treatments were carried out in the same manner as in Example 1(b) using the corresponding hydrazide compounds, thereby giving the following compounds:

3-(3-Benzoylaminophenyl)-2-furancarboxylic acid 2-(3-cyano-4-hydroxybenzoyl)hydrazide, HPLC retention time: 3.79 minutes (Example 103), 3-[3-(N-Acetyl-N-benzylamino)phenyl]-2-furancarboxylic acid 2-(3-cyano-4-hydroxybenzoyl)hydrazide, melting point: 221-222° C. (recrystallized from ethanol/ethyl acetate, Example 104), 3-(3-Acetylaminophenyl)-2-furancarboxylic acid 2-(3-cyano-4-hydroxybenzoyl)hydrazide (compound of Reference Example 71), HPLC retention time: 2.13 minutes (Example 105), 3-(3-Benzyloxycarbonylaminophenyl)-2-furancarboxylic acid 2-(3-cyano-4-hydroxybenzoyl)hydrazide, melting point: 179-181° C. (recrystallized from ethanol, Example 106), 3-(3-Butoxyphenyl)-2-furancarboxylic acid 2-(3-cyano-4-hydroxybenzoyl)hydrazide, melting point: 186-188° C. (recrystallized from ethanol, Example 107), 3-[3-(2-Hydroxy-2-phenylethoxy)phenyl]-2-furancarboxylic acid 2-(3-cyano-4-hydroxybenzoyl)hydrazide, HPLC retention time: 4.32 minutes (Example 108), and 3,4-Bis [3-(2,3,5,6-tetramethylbenzyloxy)phenyl]-2-furancarboxylic acid 2-(3-cyano-4-hydroxybenzoyl)hydrazide, Melting point (recrystallized from ethyl acetate/diisopropyl ether, Example 109).

EXAMPLE 110

Preparation of 3-(3-aminophenyl)-2-furancarboxylic acid 2-(3-cyano-4-hydroxybenzoyl)hydrazide A mixture composed of the compound of Example 106 (0.50 g), ethanol (30 ml), methanol (30 ml) and 5% palladium carbon (0.05 g) was hydrogenated while stirring at 25° C. for 6 hours. The catalyst was filtered off, and the filtrate was concentrated under reduced pressure. The residue was dissolved in 10% aqueous sodium carbonate solution and acidified with acetic acid. The thus-precipitated crystals were purified by silica gel column chromatography (eluent: methanol/chloroform=1/9), thereby giving 0.09 g of the desired compound. HPLC retention time: 1.42 minutes.

EXAMPLE 111

Preparation of 3-(4-pyridyl)-2-furancarboxylic acid 2-(3-cyano-4-hydroxybenzoyl)hydrazide A reaction and treatment was carried out in the same manner as in Example 6 except that the compound of Reference Example 23 used in Example 6 was replaced with 3-(4-pyridyl)-2-furancarboxylic acid hydrazide (prepared according to the method described in Reference Example 14 using 4-pyridylboronic acid), thereby giving the desired compound. Melting point: 280° C. (Recrystallized from methanol).

EXAMPLES 112-114

Reactions and treatments were carried out in the same manner as in Example 20 using the appropriate hydrazide compounds, thereby giving the following compounds:

3-(4-Pyridyl)-2-furancarboxylic acid 2-(4-hydroxy-3-nitrobenzoyl)hydrazide, melting point: 237° C. (recrystallized from methanol, Example 112), 3-[4-(2,3,5, 6-Tetramethylbenzyloxy)phenyl]-2-furancarboxylic acid 2-(4-hydroxy-3-nitrobenzoyl)hydrazide, melting point: 203-204° C. (recrystallized from ethyl acetate/acetonitrile, Example 113), and 3,4-Bis[3-(2,3,5,6-tetramethylbenzyloxy)phenyl]-2-furancarboxylic acid 2-(4-hydroxy-3-nitrobenzoyl)hydrazide, melting point: 174-175° C. (recrystallized from methanol, Example 114).

EXAMPLE 115

Preparation of 3,4-bis(3-benzyloxyphenyl)-2-furancarboxylic acid 2-(3-cyano-4-hydroxybenzoyl)hydrazide A reaction and treatment was carried out in the same manner as in Example 1(a) except that the compound of Reference Example 4 used in Example 1(a) was replaced with the compound of Reference Example 75, thereby giving the desired compound. Melting point: 171-174° C. (recrystallized from ethyl acetate/hexane)

EXAMPLE 116

Preparation of 3,4-diphenyl-2-furancarboxylic acid 2-(4-acetoxy-3-nitrobenzoyl)hydrazide A reaction and treatment was carried out in the same manner as in Example 94 except that the compound of Example 18 used in Example 94 was replaced with the compound of Example 19, thereby giving the desired compound. HPLC retention time: 15.15 minutes.

EXAMPLES 117 and 118

Reactions and treatments were carried out in the same manner as in Example 31 except that the 3-fluoro-4-methoxybenzoic acid used in Example 31 was replaced with appropriate 4-methoxybenzoic acid derivatives, thereby giving the following compounds:

3,4-Diphenyl-2-furancarboxylic acid 2-(3-cyano-4-methoxybenzoyl)hydrazide, melting point: 220-225° C. (recrystallized from ethanol, Example 117), and 3,4-Diphenyl-2-furancarboxylic acid 2-(4-methoxy-3-nitrobenzoyl)hydrazide, melting point: 150-158° C. (recrystallized from DMF/water, Example 118).

EXAMPLE 119

Preparation of 3-[3-(2-methylbenzyloxy)phenyl]-2-furancarboxylic acid 2-(4-hydroxy-3-nitrobenzoyl) hydrazide A reaction and treatment was carried out in the same manner as in Example 20 using the compound of Reference Example 81, thereby giving the desired compound.

EXAMPLES 120-134

Reactions and treatments were carried out in the same manner as in Reference Example 81 except that the 2-methylbenzyl chloride used in Reference Example 81 was replaced with appropriate aryl halide derivatives to thereby give hydrazide derivatives. Using these hydrazide derivatives, reactions and treatments were carried out in the same manner as in Example 119, thereby giving the compounds shown in Table 5:

TABLE 5

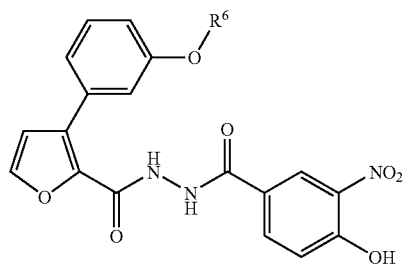

| Example | $R^6$ |
|---|---|
| 120 | 4-(methylsulfonyl)benzyl |
| 121 | 3-methoxybenzyl |
| 122 | 4-fluorobenzyl |
| 123 | 3-methylbenzyl |
| 124 | 3-pyridylmethyl |
| 125 | 2-pyridylmethyl |
| 126 | 4-methylbenzyl |
| 127 | 3,5-dimethylbenzyl |
| 128 | 3,4-dimethylbenzyl |
| 129 | 2,3-dimethylbenzyl |

TABLE 5-continued

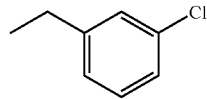

| Example | R⁶ |
|---|---|
| 130 | 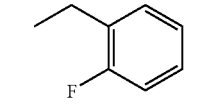 |
| 131 | 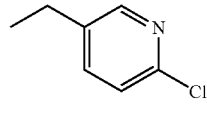 |
| 132 | 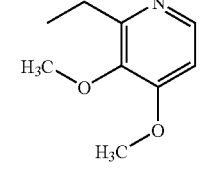 |
| 133 | 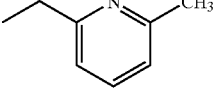 |
| 134 | 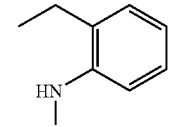 |

EXAMPLE 135

Preparation of 3-[3-(2-methylbenzyloxy)phenyl]-2-furancarboxylic acid 2-(3-cyano-4-hydroxybenzoyl)hydrazide A reaction and treatment was carried out in the same manner as in Example 1(b) using the compound of Reference Example 81, thereby giving the desired compound.

EXAMPLE 136

Preparation of 3-[3-(4-methylsulfonylbenzyloxy)phenyl]-2-furancarboxylic acid 2-(3-cyano-4-hydroxybenzoyl)hydrazide A reaction and treatment was carried out in the same manner as in Reference Example 81 except that the 2-methylbenzyl chloride used in Reference Example 81 was replaced with 4-methylsulfonylbenzyl bromide, thereby giving a hydrazide derivative. Using this hydrazide derivative, a reaction and treatment was carried out in the same manner as in Example 119, thereby giving the desired compound.

EXAMPLE 137

Preparation of 3-[3-(3-methylsulfonylaminobenzyloxy)phenyl]-2-furancarboxylic acid 2-(4-hydroxy-3-nitrobenzoyl)hydrazide A reaction and treatment was carried out in the same manner as in Example 119 except that the 3-[3-(2-methylbenzyloxy)phenyl]-2-furancarboxylic acid hydrazide used in Example 119 was replaced with the compound of Reference Example 82, thereby giving the desired compound.

EXAMPLES 138-141

Reactions and treatments were carried out in the same manner as in Reference Example 82 except that the 3-nitrobenzyl bromide used in Reference Example 82 was replaced with appropriate halogenated nitrobenzyl derivatives to thereby giving hydrazide derivatives. Using these hydrazide derivatives, reactions and treatments were conducted in the same manner as in Example 119, thereby giving the compounds shown in Table 6:

TABLE 6

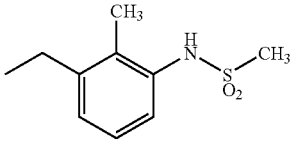

| Example | R⁶ |
|---|---|
| 138 | 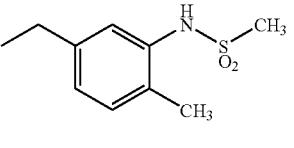 |
| 139 | 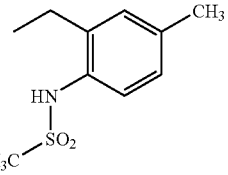 |
| 140 | |
| 141 | |

EXAMPLES 142

Preparation of 3-(4-butylphenyl)-2-furancarboxylic acid 2-(4-hydroxy-3-nitrobenzoyl)hydrazide A reaction and treatment was carried out in the same manner as in Reference Example 14 except that the phenylboronic acid used in Reference Example 14 was replaced with 4-butylphenylboronic acid, thereby giving 3-(4-butylphenyl)-2-furancarboxylic acid hydrazide. This 3-(4-butylphenyl)-2-furancarboxylic acid hydrazide (1.62 g), 4-acetoxy-3-nitrobenzoic acid (compound of Reference Example 80, 1.66 g), WSC (1.50 g) and DMF (25 ml) were stirred at 25° C. for 2 hours. The reaction solution was diluted with chloroform and successively washed with water, 20% citric acid solution, aqueous saturated sodium hydrogencarbonate solution and saturated brine. The organic layer was dried over MgSO$_4$, and the solvent was evaporated under reduced pressure. After dissolving the residue in ethanol (15 ml), 2 M aqueous sodium hydroxide solution (16 ml) was added at 25° C. and stirred for 2 hours. The reaction solution was neutralized with hydrochloric acid solution and extracted with ethyl acetate. The organic layer was dried over MgSO$_4$, and the solvent was evaporated under reduced pressure. The residue was recrystallized from acetonitrile, thereby giving 1.80 g of the desired compound.

EXAMPLES 143-163

Reactions and treatments were carried out in the same manner as in Reference Example 14 using the appropriate boronic acid derivatives to thereby give various hydrazide derivatives. Using these hydrazide derivatives, reactions and treatments were carried out in the same manner as in Example 142, thereby giving the compounds shown in Table 7:

TABLE 7

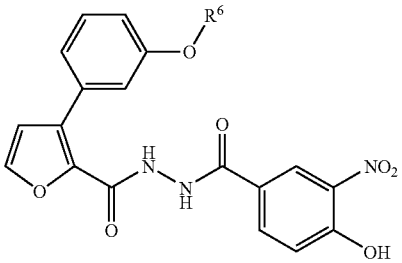

| Example | R$^1$ |
|---|---|
| 143 | Ph |
| 144 | 3-OH-Ph |
| 145 | 3-CH$_3$-Ph |
| 146 | 4-CH$_3$-Ph |
| 147 | 2-CH$_3$-Ph |
| 148 | 2-CH$_3$O-Ph |
| 149 | 4-CH$_3$O-Ph |
| 150 | 3,4-(CH$_3$)$_2$-Ph |
| 151 | 3,4,5-(CH$_3$)$_3$-Ph |
| 152 | 3-CH(CH$_3$)$_2$-Ph |
| 153 | 4-CH(CH$_3$)$_2$-Ph |
| 154 | 4-F-Ph |
| 155 | 4-CH$_3$CO-Ph |
| 156 | 4-CH$_3$CH$_2$-Ph |
| 157 | 2-CH$_3$-4-CH$_3$O-Ph |
| 158 | 4-CH$_3$(CH$_2$)$_4$CH$_2$-Ph |
| 159 | 4-CH$_3$CH$_2$(CH$_2$)$_3$O-Ph |
| 160 | 4-CH$_3$CH$_2$CH$_2$-Ph |
| 161 | 4-CH$_3$CH$_2$(CH$_2$)$_2$O-Ph |
| 162 | 4-CH$_3$CH$_2$(CH$_2$)$_3$-Ph |
| 163 | 4-CH$_3$CH$_2$CH$_2$O-Ph |

EXAMPLE 164

Preparation of 3-[3-(2-methoxy-5-pyridylmethyloxy)phenyl]-2furancarboxylic acid 2-(4-hydroxy-3-nitrobenzoyl)hydrazide A reaction and treatment was carried out in the same manner as in Reference Example 20 using the compound of Reference Example 83, thereby giving the desired compound.

EXAMPLES 165-171

Reactions and treatments were carried out in the same manner as in Example 142 using the appropriate hydrazide derivatives synthesized from suitable pyridylmethyl derivatives, thereby giving the compounds shown in Table 8:

TABLE 8

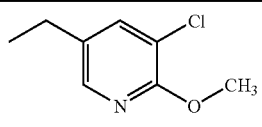

| Example | R$^6$ |
|---|---|
| 165 | 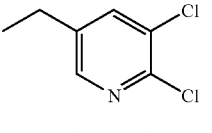 |
| 166 | 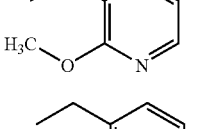 |
| 167 | 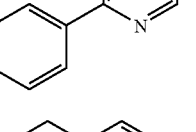 |
| 168 | 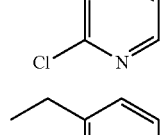 |
| 169 | 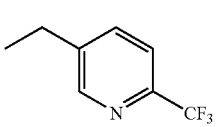 |
| 170 |  |
| 171 |  |

EXAMPLE 172

Preparation of 3-(3-methanesulfonyloxyphenyl)-2-furancarboxylic acid 2-(4-hydroxy-3-nitrobenzoyl) hydrazide A reaction and treatment was carried out in the same manner as in Reference Example 20 using the compound of Reference Example 84, thereby giving the desired compound.

EXAMPLES 173 and 174

Reactions and treatments were carried out in the same manner as in Example 20 using hydrazide derivatives synthesized with the sulfonyl chloride derivative of Reference Example 84, thereby giving the compounds shown in Table 9:

TABLE 9

| Example | $R^6$ |
|---|---|
| 173 | Ph |
| 174 | Bn |

EXAMPLES 175-187

Reactions and treatments were carried out in the same manner as in Reference Example 81 except that the 2-methylbenzyl chloride used in Reference Example 81 was replaced with appropriate halides to thereby give various hydrazide derivatives. Using these hydrazide derivatives, reactions and treatments were carried out in the same manner as in Example 142, thereby giving the compounds shown in Table 10:

TABLE 10

| Example | $R^6$ |
|---|---|
| 175 | 2-methoxybenzyl |
| 176 | 4-methoxybenzyl |
| 177 | 3-fluorobenzyl |
| 178 | 3-carbamoylbenzyl |
| 179 | 2-acetamidobenzyl |
| 180 | 2-methylbutyl |
| 181 | n-butyl |
| 182 | n-pentyl |
| 183 | isobutyl |
| 184 | n-hexyl |
| 185 | n-heptyl |
| 186 | cyclobutylmethyl |
| 187 | cyclobutyl |

EXAMPLES 188-192

A reaction and treatment was carried out in the same manner as in Reference Example 24 except that the compound of Reference Example 5 used in Reference Example 24 was replaced with the compound of Reference Example 77(1), thereby giving ethyl 3-(3-trifluoromethylsulfonyloxy)-2-furancarboxylate. Using this compound and various zinc bromides or zinc chlorides, reactions and treatments were carried out in the same manner as in Reference Example 25, thereby giving various hydrazide derivatives. Using these hydrazide derivatives, reactions and treatments were conducted in the same manner as in Example 142, thereby giving the compounds shown in Table 11:

TABLE 11

| Example | -(X)m-R$^6$ |
|---|---|
| 188 | ~~~CH$_3$ (n-hexyl) |
| 189 | CH$_2$-phenyl (benzyl) |
| 190 | isobutyl (CH$_2$CH(CH$_3$)CH$_3$) |
| 191 | CH$_2$CH$_2$CH(CH$_3$)$_2$ (isopentyl) |
| 192 | n-pentyl |

EXAMPLE 193

Preparation of 3-phenyl-2-furancarboxylic acid 2-(4-hydroxy-3-trifluoromethylbenzoyl)hydrazide A reaction and treatment was carried out in the same manner as in Example 142 using the compound of Reference Example 85 and the compound of Reference Example 14, thereby giving the desired compound.

EXAMPLE 194

Preparation of 3-phenyl-2-furancarboxylic acid 2-(3-tert-butyloxycarbonyl-4-hydroxybenzoyl)hydrazide A reaction and treatment was carried out in the same manner as in Example 142 using the compound of Reference Example 86 and the compound of Reference Example 14, thereby giving the desired product.

EXAMPLE 195

Preparation of 3-phenyl-2-furancarboxylic acid 2-(3-carboxy-4-hydroxybenzoyl)hydrazide The compound of Example 194 (0.2 g) was mixed with 4 M hydrochloric acid/ethyl acetate and stirred overnight at 25° C. After distilling off the solvent under reduced pressure, the residue was recrystallized from ethyl acetate/hexane, thereby giving 0.14 g of the desired compound.

EXAMPLES 196-206

Using corresponding halides of either ethyl 3-(3-hydroxyphenyl)-2-furancarboxylate obtained by the reaction and treatment carried out in the same manner as in Reference Example 1 or the compound of Reference Example 87, the compound of Reference example 2 was converted into various hydrazide derivatives by a reaction and treatment carried out in the same manner as in Reference Example 81, and then reactions and treatments were carried out in the same manner as in Example 142, thereby giving the compounds shown in Tables 12 and 13:

TABLE 12

| Example | R$^6$ |
|---|---|
| 196 | CH$_2$CH=C(CH$_3$)CH$_3$ |
| 197 | CH$_2$C(=CH$_2$)CH$_3$ |
| 198 | CH$_2$CH=CHCH$_3$ |
| 199 | CH$_2$CH=CH$_2$ |
| 200 | CH$_2$C≡CCH$_3$ |
| 201 | CH$_2$CH=CHCH$_2$CH$_3$ |
| 202 | CH$_2$CH$_2$CH=CHCH$_3$ |

TABLE 12-continued

[Structure: 3-substituted phenyl-furan hydrazide with R⁶O group, NO₂ and OH on benzoyl]

| Example | R⁶ |
|---|---|
| 203 | 1-ethylnaphthalene group |
| 204 | 2-ethylnaphthalene group |

TABLE 13

[Structure: 4-substituted phenyl-furan hydrazide with O—R⁶ group, NO₂ and OH on benzoyl]

| Example | R⁶ |
|---|---|
| 205 | –CH₂CH=C(CH₃)CH₃ (prenyl-type) |
| 206 | –CH₂C(=CH₂)CH₂CH₃ type |

EXAMPLES 207 and 208

Reactions and treatments were carried out in the same manner as in Reference Example 14 using the appropriate boronic acid derivatives to thereby give hydrazide derivatives. Using these hydrazide derivatives, reactions and treatments were conducted in the same manner as in Example 142, thereby giving the compounds shown in Table 14:

TABLE 14

[Structure: 3-R¹-furan-2-carbohydrazide with 4-hydroxy-3-nitrobenzoyl]

| Example | R¹ |
|---|---|
| 207 | 5-methylindole (NH) |
| 208 | 1,5-dimethylindole (N-CH₃) |

EXAMPLE 209

Preparation of 3-(3-phenethyloxyphenyl)-2-furancarboxylic acid 2-(4-hydroxy-3-nitrobenzoyl)hydrazide A reaction and treatment was carried out in the same manner as in Example 142 using the compound of Reference Example 88, thereby giving the desired compound.

EXAMPLE 210

Preparation of 3-(4-benzylphenyl)-2-furancarboxylic acid 2-(4-hydroxy-3-nitrobenzoyl)hydrazide A reaction and treatment was carried out in the same manner as in Reference Example 24 using the compound of Reference Example 87, thereby giving ethyl 3-(4-trifluoromethylsulfonyloxy)-2-furancarboxylate. Using this compound and benzyl zinc bromide, a reaction and treatment was carried out in the same manner as in Reference Example 25 to prepare various hydrazine derivatives. Using these hydrazide derivatives, a reaction and treatment was carried out in the same manner as in Example 142, thereby giving the desired compound.

EXAMPLES 211-216

After carring out reactions and treatments in the same manner as in Reference Example 81 using halides corresponding to ethyl 3-(4-hydroxyphenyl)-2-furancarboxylate (compound of Reference Example 87) to give various hydrazide derivatives, reactions and treatments were carried out in the same manner as in Example 142, thereby giving the compounds shown in Table 15.

Using the compounds of Reference Examples 89 and 90, reactions and treatments were carried out in the same manner as in Example 142, thereby giving the compounds shown also in Table 15.

TABLE 15

[Structure: furan with 3-(4-OR⁶-phenyl) substituent, 2-carbohydrazide linked to 4-hydroxy-3-nitrobenzoyl]

| Example | R⁶ |
|---|---|
| 211 | 4-methylbenzyl (–CH₂–C₆H₄–CH₃, para) |
| 212 | n-hexyl (–(CH₂)₅–CH₃) |
| 213 | 2-methylbenzyl |
| 214 | 3-methylbenzyl |
| 215 | –CH₂–C(=O)–NH–phenyl |
| 216 | –CH₂–CH₂–C(=O)–phenyl |

EXAMPLES 217-221

Reactions and treatments were carried out in the same manner as in Reference Example 14 using the appropriate boronic acid derivatives to thereby give various hydrazide derivatives. Using these hydrazide derivatives, reactions and treatments were carried out in the same manner as in Example 142, thereby giving the compounds shown in Table 16:

TABLE 16

[Structure: furan with 3-R¹ substituent, 2-carbohydrazide linked to 4-hydroxy-3-nitrobenzoyl]

| Example | R¹ |
|---|---|
| 217 | 6-methylnaphthalen-2-yl |
| 218 | 3'-methylbiphenyl-3-yl |
| 219 | 4-(ethylthio)phenyl (–C₆H₄–S–CH₂CH₃) |
| 220 | 6-ethoxynaphthalen-2-yl |
| 221 | 5-methylquinolin-8-yl |

EXAMPLE 222

Preparation of 5-bromo-3-phenyl-2-furancarboxylic acid 2-(4-hydroxy-3-nitrobenzoyl)hydrazide After carrying out a reaction and treatment in the same manner as in Reference Example 10(3) using ethyl 5-bromo-3-phenyl-2-furancarboxylate as produced in Reference Example 55 to prepare a hydrazine derivative, another reaction and treatment was conducted in the same manner as in Example 142, thereby giving the desired compound.

EXAMPLES 223 and 224

After carring out reactions and treatments in the same manner as in Reference Example 81 using halides corresponding to ethyl 3-(3-hydroxyphenyl)-2-furancarboxylate (compound of Reference Example 77(1)) to give hydrazide derivatives, reactions and treatments were carried out in the same manner as in Example 142, thereby giving the compounds shown in Table 17.

TABLE 17

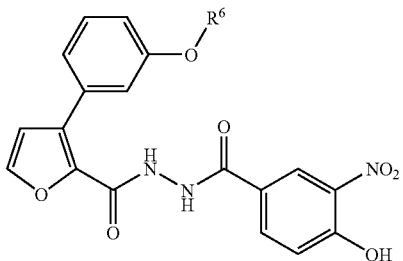

| Example | R[6] |
|---|---|
| 223 | 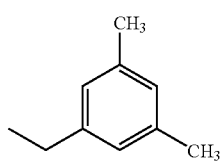 |
| 224 | 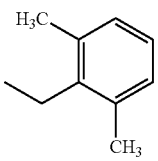 |

EXAMPLES 225-238

A reaction and treatment was carried out in the same manner as in Reference Example 24 using ethyl 3-(3-hydroxyphenyl)-2-furancarboxylate (compound of Reference Example 77(1)), thereby giving ethyl 3-(3-trifluoromethylsulfonyloxy)-2-furancarboxylate. Using this compound and various zinc bromides or zinc chlorides, reactions and treatments were carried out in the same manner as in Reference Example 25 to prepare various hydrazine derivatives. Using these hydrazide derivatives, reactions and treatments were carried out in the same manner as in Example 142, thereby giving the compounds shown in Table 18.

TABLE 18

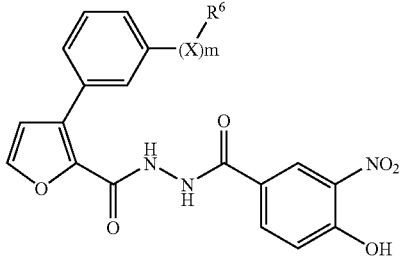

| Example | -(X)m-R[6] |
|---|---|
| 225 | 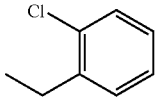 |

TABLE 18-continued

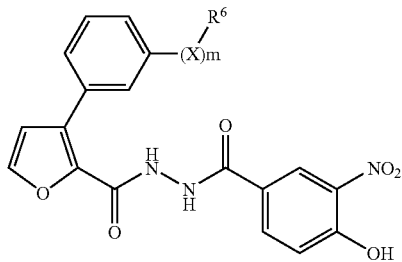

| Example | -(X)m-R[6] |
|---|---|
| 226 | 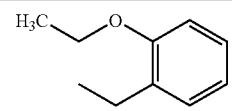 |
| 227 | 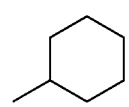 |
| 228 | 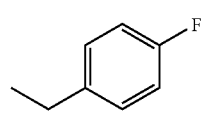 |
| 229 | 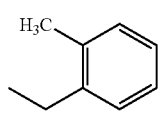 |
| 230 | 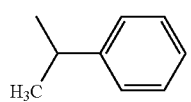 |
| 231 | 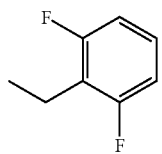 |
| 232 | 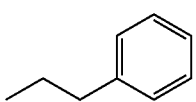 |
| 233 | 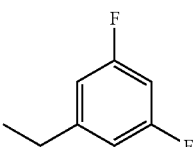 |
| 234 | 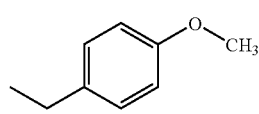 |
| 235 | 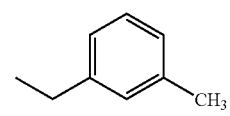 |

TABLE 18-continued

[Structure: furan with R6-(X)m-phenyl substituent, connected via hydrazide linkage to 3-NO2-4-OH-benzoyl group]

| Example | -(X)m-R6 |
|---------|----------|
| 236 | [4-cyanobenzyl with ethyl] |
| 237 | [pentyl-CH3 chain] |
| 238 | [α-methylstyrene, H2C=C(Ph)-] |

EXAMPLES 239-248

(1) Reactions and treatments were carried out in the same manner as in Reference Example 14 using suitable boronic acid derivatives, thereby giving various hydrazide derivatives.

(2) Using 4-hydroxyfluorobenzoic acid and 4-hydroxy-3-chlorobenzoic acid, reactions and treatments were carried out in the same manner as in Reference Example 80, thereby giving various benzoic acid derivatives.

(3) Using the various hydrazide derivatives obtained in (1), the various benzoic acid derivatives obtained in (2) or 4-acetoxy-3-trifluoromethylbenzoic acid (compound of Reference Example 85), reactions and treatments were carried out in the same manner as in Example 142, thereby giving the compounds shown in Table 19.

TABLE 19

[Structure: R6-phenyl-furan-C(O)-NH-NH-C(O)-phenyl(R4)(OH)]

| Example | R6 | R4 |
|---------|-----|-----|
| 239 | $CH_3$ | Cl |
| 240 | $CH_3$ | $CF_3$ |
| 241 | $CH_3CH_2CH_2$ | F |
| 242 | $CH_3CH_2CH_2$ | $CF_3$ |
| 243 | $CH_3CH_2(CH_2)_3O$ | F |
| 244 | $CH_3CH_2(CH_2)_3O$ | $CF_3$ |

TABLE 19-continued

[Same structure as Table 19]

| Example | R6 | R4 |
|---------|-----|-----|
| 245 | $PhCH_2-O$ | $NO_2$ |
| 246 | $PhCH_2-O$ | $CF_3$ |

EXAMPLES 247 and 248

Reactions and treatments were carried out in the same manner as in Reference Example 25 using ethyl 5-bromo-3-phenyl-2-furancarboxylate as produced in Reference Example 55 and various zinc bromides or zinc chlorides, thereby giving hydrazide derivatives. Using these hydrazide derivatives, reactions and treatments were carried out in the same manner as in Example 142, thereby giving the compounds shown in Table 20.

TABLE 20

[Structure: 3-phenyl-furan with R3 at 5-position, connected via hydrazide to 3-NO2-4-OH-benzoyl]

| Example | R3 |
|---------|-----|
| 247 | [2-methoxy-6-ethylphenyl, $H_3C-O-$] |
| 248 | [n-hexyl, $-CH_2CH_2CH_2CH_2CH_2CH_3$] |

The melting points, results of HPLC analysis (Rt: retention time) and NMR spectra of the compounds of Examples 119-248 are shown in Tables 21, 22 and 23, respectively.

TABLE 21

| Ex. | Melting point (° C.) | Solvent for recrystallization* |
|-----|---------------------|-------------------------------|
| 119 | 114-115 | a |
| 120 | 114-117 | a |
| 121 | 155-163 | b |
| 122 | 143-149 | a |
| 123 | 144-145 | c |
| 124 | 100-101 | d |

TABLE 21-continued

| Ex. | Melting point (° C.) | Solvent for recrystallization* |
|---|---|---|
| 125 | 138-142 | c |
| 126 | 159-161 | e |
| 127 | 131-132 | a |
| 128 | 172-173 | e |
| 129 | 157-162 | a |
| 130 | 147-150 | a |
| 131 | 105-107 | a |
| 132 | 185-187 | d |
| 134 | 211-214 | a |
| 135 | 178-180 | c |
| 136 | 235-237 | e |
| 139 | 193-194 | f |
| 140 | 201-202 | f |
| 141 | 218-219 | f |
| 142 | 190-193 | a |
| 143 | 154-156 | a |
| 145 | 126-128 | a |
| 146 | 180-182 | a |
| 147 | 172-175 | a |
| 148 | 92-95 | i |
| 149 | 184-186 | a |
| 150 | 127-129 | a |
| 151 | 238-240 | a |
| 152 | 182-183 | a |
| 153 | 194-196 | a |
| 154 | 169-171 | a |
| 155 | 182-184 | a |
| 156 | 189-191 | a |
| 157 | 114-116 | a |
| 158 | 144-146 | a |
| 159 | 156-157 | a |
| 160 | 174-176 | a |
| 161 | 155-156 | a |
| 162 | 163-165 | a |
| 163 | 155-157 | a |
| 164 | 180-181 | a |
| 165 | 165-167 | a |
| 166 | 228-230 | g |
| 167 | 98-101 | a |
| 168 | 194-196 | a |
| 169 | 173-175 | a |
| 170 | 218-220 | a |
| 171 | 223-229 | i |
| 172 | 170-171 | a |
| 173 | 174-175 | a |
| 175 | 180-181 | d |
| 176 | 172-174 | d |
| 177 | 120-122 | c |
| 180 | 122-124 | a |
| 181 | 135-138 | a |
| 182 | 96-99 | a |
| 183 | 98-100 | a |
| 184 | 124-126 | a |
| 185 | 141-144 | a |
| 186 | 154-156 | a |
| 187 | 150-153 | d |
| 188 | 87-89 | a |
| 189 | 160-162 | h |
| 190 | 167-169 | a |
| 191 | 100-102 | a |
| 192 | 107-109 | a |
| 193 | 117-121 | a |
| 194 | 147-154 | c |
| 195 | 250-251 | c |
| 196 | 84-85 | a |
| 197 | 127-129 | f |
| 198 | 113-115 | j |
| 199 | 126-131 | i |
| 200 | 108-110 | a |
| 201 | 94-96 | a |
| 202 | 88-90 | a |
| 203 | 152-153 | a |
| 204 | 198-199 | a |
| 205 | 120-122 | a |
| 206 | 152-154 | c |
| 207 | 129-131 | i |
| 208 | 185-187 | a |
| 209 | 90-94 | a |
| 210 | 154-157 | a |
| 211 | 184-185 | a |
| 212 | 154-156 | a |
| 213 | 177-179 | a |
| 214 | 162-164 | a |
| 215 | 218-220 | j |
| 217 | 135-139 | a |
| 218 | 143-147 | a |
| 219 | 178-182 | a |
| 220 | 194-195 | a |
| 221 | 249-253 | a |
| 222 | 174-176 | a |
| 223 | 178-180 | a |
| 224 | 100-101 | a |
| 225 | 97-99 | a |
| 226 | 87-89 | a |
| 227 | 135-138 | a |
| 228 | 173-175 | a |
| 229 | 135-138 | a |
| 231 | 145-147 | a |
| 230 | 147-149 | a |
| 232 | 149-152 | k |
| 233 | 110-112 | a |
| 234 | 102-104 | a |
| 235 | 149-151 | a |
| 236 | 139-141 | a |
| 237 | 119-121 | a |
| 238 | 149-150 | a |
| 239 | 240-242 | a |
| 240 | 120-123 | a |
| 241 | 102-105 | a |
| 242 | 112-114 | a |
| 243 | 103-106 | a |
| 244 | 177-178 | a |
| 245 | 163-164 | a |
| 246 | 204-205 | a |
| 247 | 162-164 | a |
| 248 | 148-150 | a |

*a: acetonitrile, b: ethanol/ethyl acetate, c: ethyl acetate/hexane, d: ethanol, e: ethyl acetate, f: water/ethanol, g: methanol/chloroform, h: methanol/acetonitrile, i: 1 M aqueous sodium hydroxide solution/1 M hydrochloric acid, j: methanol, k: ethanol/acetonitrile/ethyl acetate

TABLE 22

| Example | $R_t$ (min) |
|---|---|
| 133 | 2.00 |
| 137 | 3.69 |
| 138 | 3.63 |
| 144 | 2.42 |
| 174 | 3.67 |
| 178 | 2.44 |
| 179 | 2.95 |

TABLE 23

| Example | $^1$H-NMR(DMSO-$d_6$, δ) |
|---|---|
| 215 | 5.61(s, 2H), 6.92-7.10(m, 3H), 7.23(d, J=8.6Hz, 1H), 7.50-7.60(m, 2H), 7.62-7.66(m, 3H), 7.92(d, J=1.8Hz, 1H), 7.99-8.09(m, 3H), 8.46(d, J=2.0Hz, 1H), 10.33(s, 1H), 10.50(s, 1H), 11.74(br s, 1H) |

INDUSTRIAL APPLICABILITY

Since the compounds of the present invention (I), and prodrugs, physiologically acceptable salts, hydrates and solvates thereof exhibit a potent antagonistic activity on glucagon receptor and have low toxicity, they can be used in the prevention and/or treatment of symptoms and diseases in which glucagon is involved, such as hyperglycemia, abnormal glucose tolerance, insulin resistance syndrome, syndrome X, type I diabetes, type II diabetes, hyperlipidemia, hypertriglyceridemia, hyperlipoproteinemia, hypercholesterolemia, arteriosclerosis, glucagonoma, acute pancreatitis, cardiovascular disorders, hypertension, cardiac hypertrophy, gastrointestinal disorders, obesity, diabetes caused by obesity, diabetic complications (cataracts, retinopathy, karatopathy, neuropathy, nephropathy, etc.) and other such symptoms and diseases.

The invention claimed is:

1. A 2-furancarboxylic acid hydrazide compound represented by Formula (I) below, or a physiologically acceptable salt thereof:

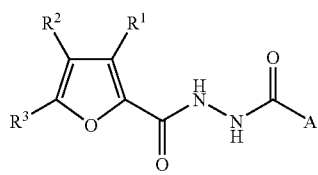

wherein A is a group represented by Formula (a) below, or a substituted or unsubstituted heteroaryl group other than 2-furyl group:

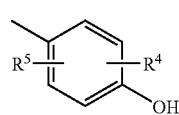

wherein either $R^4$ or $R^5$ represents a hydrogen atom, a halogen atom, a trifluoromethyl group, a hydroxy group, a $C_{1-6}$ alkyl group, a $C_{2-6}$ alkenyl group, a $C_{2-6}$ alkynyl group, a $C_{1-6}$ alkoxy group, a trifluoromethoxy group, a trifluoroethoxy group, a $C_{1-2}$ alkylsulfonyl group, a cyano group, a nitro group, an amino group, a mono- or di-substituted amino group, a $C_{1-6}$ alkoxycarbonylamino group, a carbamoyl group, a mono- or di-substituted carbamoyl group, a sulfamoyl group, a mono- or di-substituted sulfamoyl group, a $C_{1-6}$ alkylsulfonylamino group, an aryl group, a heteroaryl group, a $C_{1-6}$ alkoxycarbonyl group, an arylmethyloxycarbonyl group, a carboxyl group, a 5-tetrazolyl group, a sulfo group (—$SO_2OH$) or a fluorosulfonyl group, and the other represents a hydrogen atom or a halogen atom, either $R^1$ or $R^2$ represents a group: -D-(X)m-$R^6$, an aryl group or a heteroaryl group, and the other represents a group: -E-(Y)n-$R^7$, a hydrogen atom, a halogen atom, a $C_{1-10}$ alkyl group, a $C_{3-7}$ cycloalkyl group, a $C_{2-10}$ alkenyl group, a $C_{2-10}$ alkynyl group, an aryl group or a heteroaryl group, with the alkyl group, the alkenyl group and the alkynyl group being optionally substituted by 1 to 3 atoms or groups selected from halogen, hydroxy (this hydroxy itself being optionally acylated, carbamated or etherified), disubstituted amino, aryl and heteroaryl, $R^3$ is a hydrogen atom, a halogen atom, a hydroxy group, a $C_{1-6}$ alkyl group, a $C_{1-6}$ alkoxy group, an aryl group, a heteroaryl group or an aryl-substituted $C_{1-4}$ alkyl group, D and E are the same or different, and independently represent an arylene group, X and Y are the same or different, and independently represent —O—, —S—, —SO—, —$SO_2$—, —$OSO_2$—, —$NR^8$—, —CO—, —CH=CH—, —C≡C—, —CONH—, —NHCO—, —NHCOO—, —$OCH_2CONH$— or —$OCH_2CO$—, $R^6$ and $R^7$ are the same or different, and independently represent a $C_{1-10}$ alkyl group, a $C_{2-10}$ alkenyl group, a $C_{2-10}$ alkynyl group, a $C_{3-7}$ cycloalkyl group, a $C_{3-7}$ cycloalkyl-substituted $C_{1-4}$ alkyl group, an aryl group, a heteroaryl group, an aryl-substituted $C_{1-4}$ alkyl group or a heteroaryl-substituted $C_{1-4}$ alkyl group, with the alkyl moiety of the aryl-substituted $C_{1-4}$ alkyl group or the heteroaryl-substituted $C_{1-4}$ alkyl group being optionally substituted by hydroxy, $R^8$ is a hydrogen atom or a $C_{1-10}$ alkylcarbonyl group, and m and n are independently 0 or 1, provided that the aryl group, the aryl moiety, the heteroaryl group, the heteroaryl moiety and the arylene group are optionally substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or disubstituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl).

2. A 2-furancarboxylic acid hydrazide compound represented by Formula (I0) below, or a physiologically acceptable salt thereof:

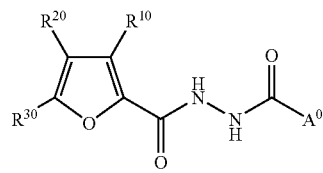

wherein $A^0$ is a group represented by Formula (a0) below, or a heteroaryl group other than 2-furyl group optionally substituted by halogen, trifluoromethyl, trifluoromethoxy, trifluoroethoxy, cyano, nitro or $C_{1-3}$ alkylsulfonyl:

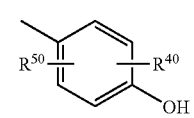

wherein $R^{40}$ is a hydrogen atom, a halogen atom, a trifluoromethyl group, a hydroxy group, a $C_{1-6}$ alkyl group, a $C_{2-6}$ alkenyl group, a $C_{2-6}$ alkynyl group, a $C_{1-6}$ alkoxy group, a trifluoromethoxy group, a trifluoroethoxy group, a $C_{1-2}$ alkylsulfonyl group, a cyano group, a nitro group, an amino group, a monoor disubstituted amino group, a $C_{1-6}$ alkoxycarbonylamino group, a carbamoyl group, a mono- or disubstituted carbamoyl group, a sulfamoyl group, a mono- or di-substituted sulfamoyl group, a $C_{2-6}$ alkylsulfonylamino group, an aryl group, a heteroaryl group, a $C_{1-6}$ alkoxycarbonyl group, an arylmethyloxycarbonyl group, a carboxyl group, a 5-tetrazolyl group, a sulfo group ($-SO_2OH$) or a fluorosulfonyl group, $R^{50}$ is a hydrogen atom or a halogen atom, either $R^{10}$ or $R^{20}$ is a group: $-D^0-(X^0)m^0-R^{60}$; or an aryl group or a heteroaryl group optionally substituted by 1 to 4 atoms or groups selected from halogen, hydroxy, hydroxy $C_{1-3}$ alkyl, trifluoromethyl, trifluoromethoxy, trifluoroethoxy, cyano, nitro, amino, disubstituted amino, carbamoyl, sulfamoyl, $C_{1-3}$ alkylsulfonylamino and methylenedioxy, and the other is a group: $-E^0-(Y^0)n^0-R^{70}$; a hydrogen atom; a halogen atom; a $C_{1-10}$ alkyl group, a $C_{2-10}$ alkenyl group or a $C_{2-10}$ alkynyl group optionally substituted by 1 to 3 atoms or groups selected from halogen, hydroxy, $C_{1-6}$ alkylcarbonyloxy, arylcarbonyloxy, aryl-substituted $C_{1-4}$ alkylcarbonyloxy, $C_{1-6}$ alkylaminocarbonyloxy, arylaminocarbonyloxy, aryl-substituted $C_{1-4}$ alkylaminocarbonyloxy, $C_{1-6}$ alkyloxy, aryl-substituted $C_{1-4}$ alkyloxy, disubstituted amino, aryl and heteroaryl; a $C_{3-7}$ cycloalkyl group; an aryl group or a heteroaryl group optionally substituted by 1 to 4 atoms or groups selected from halogen, hydroxy, hydroxy $C_{1-3}$ alkyl, trifluoromethyl, trifluoromethoxy, trifluoroethoxy, cyano, nitro, amino, disubstituted amino, carbamoyl, sulfamoyl, $C_{1-3}$ alkylsulfonylamino and methylenedioxy, $R^{30}$ is a hydrogen atom; a halogen atom; a hydroxy group; a $C_{1-6}$ alkyl group; a $C_{1-6}$ alkoxy group; an aryl group or a heteroaryl group optionally substituted by 1 to 4 atoms or groups selected from the group consisting of halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl); or an aryl-substituted $C_{1-4}$ alkyl group wherein the aryl moiety may be substituted by 1 to 4 atoms or groups selected from the group consisting of halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl), $D^0$ and $E^0$ are the same or different, and independently represent an arylene group optionally substituted by 1 to 3 atoms or groups selected from halogen, $C_{1-6}$ alkyl, $C_{1-6}$ alkoxy, trifluoromethyl, trifluoromethoxy and trifluoroethoxy, $X^0$ and $Y^0$ are the same or different, and independently represent —O—, —S—, —SO—, —SO$_2$—, —OSO$_2$—, —NR$^{80}$—, —CO—, —CH=CH—, —C≡C—, —CONH—, —NHCO—, —NHCOO—, —OCH$_2$CONH— or —OCH$_2$CO—, $R^{60}$ and $R^{70}$ are the same or different, and independently represent a $C_{1-10}$ alkyl group; a $C_{2-10}$ alkenyl group; a $C_{2-10}$ alkynyl group; a $C_{3-7}$ cycloalkyl group; a $C_{3-7}$ cycloalkyl-substituted $C_{1-4}$ alkyl group; an aryl group or a heteroaryl group optionally substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl); or an aryl- or heteroaryl-substituted $C_{1-4}$ alkyl group wherein the alkyl moiety may be substituted by hydroxy and the aryl moiety or the heteroaryl moiety may be substituted by 1 to 4 atoms or groups selected from halogen, hydroxy, $C_{1-6}$ alkyl, hydroxy $C_{1-3}$ alkyl, $C_{1-6}$ alkoxy, trifluoromethyl, trifluoromethoxy, trifluoroethoxy, cyano, nitro, amino, mono- or di-substituted amino, carbamoyl, sulfamoyl, $C_{1-6}$ alkylsulfonyl, $C_{1-3}$ alkylsulfonylamino, $C_{1-3}$ alkylcarbonylamino, methylenedioxy and aryl (this aryl itself being optionally substituted by halogen or trifluoromethyl), $R^{80}$ is a hydrogen atom or a $C_{1-10}$ alkylcarbonyl group, and $m^0$ and $n^0$ are independently 0 or 1.

3. The 2-furancarboxylic acid hydrazide compound according to claim 2 wherein $A^0$ is a group represented by Formula (a0), or a physiologically acceptable salt thereof.

4. The 2-furancarboxylic acid hydrazide compound, or a physiologically acceptable salt thereof according to claim 3, wherein $A^0$ is represented by Formula (b0) below:

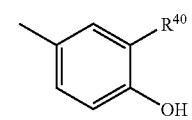

(b0)

wherein $R^{40}$ is a halogen atom, a trifluoromethyl group, a $C_{2-6}$ alkynyl group, a trifluoromethoxy group, a trifluoroethoxy group, a $C_{1-2}$ alkylsulfonyl group, a cyano group, a nitro group, a $C_{1-4}$ alkoxycarbonylamino group, a carbamoyl group, a mono- or di-substituted carbamoyl group, a sulfamoyl group, a mono- or di-substituted sulfamoyl group, a $C_{1-4}$ alkylsulfonylamino group, a $C_{1-4}$ alkoxycarbonyl group, an arylmethyloxycarbonyl group, a carboxyl group, a 5-tetrazolyl group, a sulfo group ($-SO_2OH$) or a fluorosulfonyl group, either $R^{10}$ or $R^{20}$ is a group: $-D^0-(X^0)m^0-R^{60}$; or a phenyl group or an indolyl group optionally substituted by halogen or hydroxy, and the other is a group: $-E^0-(Y^0)n^0-R^{70}$, a hydrogen atom, a halogen atom, a $C_{1-10}$ alkyl group, a $C_{2-10}$ alkenyl group, a $C_{2-10}$ alkynyl group, or a phenyl group optionally substituted by halogen or hydroxy, $R^{30}$ is a hydrogen atom, $D^0$ and $E^0$ are phenylene groups, $X^0$ and $Y^0$ are the same or different, and independently represent —O—, —S—, —CH=CH—, —OCH$_2$CONH— or —OCH$_2$CO—, $R^{60}$ and $R^{70}$ are the same or different, and independently represent a $C_{1-10}$ alkyl group, a $C_{2-10}$ alkenyl group, a $C_{2-10}$ alkynyl group, a phenyl $C_{1-4}$ alkyl group, a naphthylmethyl group, a thienylmethyl group or a pyridylmethyl group whose cyclic moiety may be substituted by 1 to 4 atoms or groups selected from halogen, $C_{1-4}$ alkyl, hydroxymethyl, $C_{1-3}$ alkoxy, trifluoromethyl, trifluoromethoxy, nitro, disubstituted amino, carbamoyl, sulfamoyl, methylsulfonylamino, $C_{1-3}$ alkylcarbonylamino, methylenedioxy and phenyl (this phenyl itself being optionally substituted by halogen or trifluoromethyl), and $m^0$ and $n^0$ are independently 0 or 1.

5. A 2-furancarboxylic acid hydrazide compound represented by Formula (Ia) below, or a physiologically acceptable salt thereof:

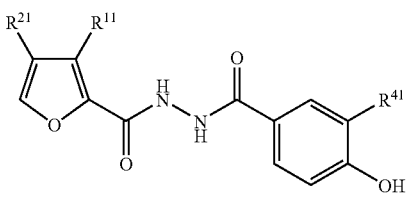

(Ia)

wherein $R^{41}$ is a halogen atom, a trifluoromethyl group, an ethynyl group, a methylsulfonyl group, a cyano group, a nitro group, a tert-butoxycarbonyl group or a carbamoyl group, $R^{11}$ is a halogen atom; a vinyl group; an ethynyl group; or a phenyl group or an indolyl group optionally substituted by a group: —$X^1$—$R^{61}$, $C_{1-10}$ alkyl, halogen or hydroxy, when $R^{11}$ is a halogen atom; a vinyl group; an ethynyl group, $R^{21}$ represents a phenyl group optionally substituted by a group: —$Y^1$—$R^{71}$, $C_{1-10}$ alkyl, halogen or hydroxy, and when $R^{11}$ is a phenyl group or an indolyl group optionally substituted by a group: —$X^1$—$R^{61}$, $C_{1-10}$ alkyl, halogen or hydroxy, $R^{21}$ is a hydrogen atom; a halogen atom; a vinyl group; an ethynyl group; or a phenyl group optionally substituted by a group: —$Y^1$—$R^{71}$, $C_{1-10}$ alkyl, halogen or hydroxy, wherein $X^1$ and $Y^1$ are the same or different, and independently represent —O—, —S—, —CH=CH—, —OCH$_2$CONH— or —OCH$_2$CO—, $R^{61}$ and $R^{71}$ are the same or different, and independently represent a $C_{1-10}$ alkyl group, a $C_{2-10}$ alkenyl group, a $C_{2-10}$ alkynyl group, a phenyl $C_{1-4}$ alkyl group, a naphthylmethyl group or a pyridylmethyl group whose cyclic moiety may be substituted by 1 to 4 atoms or groups selected from halogen, $C_{1-4}$ alkyl, hydroxymethyl, $C_{1-3}$ alkoxy, trifluoromethyl, trifluoromethoxy, nitro, disubstituted amino, carbamoyl, sulfamoyl, methylsulfonylamino, $C_{1-3}$ alkylcarbonylamino, methylenedioxy and phenyl (this phenyl itself being optionally substituted by halogen or trifluoromethyl).

6. The 2-furancarboxylic acid hydrazide compound, or a physiologically acceptable salt thereof according to claim 5, wherein $R^{41}$ is a cyano or nitro group.

7. The 2-furancarboxylic acid hydrazide compound, or a physiologically acceptable salt thereof according to claim 6, wherein $R^{11}$ is a phenyl group or an indolyl group optionally substituted by a group: —$X^1$—$R^{61}$, $C_{1-10}$ alkyl, halogen or hydroxy, $R^{21}$ is a hydrogen atom or a phenyl group optionally substituted by $C_{1-10}$ alkyl, halogen or hydroxy, $X^1$ and $R^{61}$ are the same as defined in claim 5, and $X^1$ is bound to the 3- or 4-position of the phenyl group.

8. A 2-furancarboxylic acid hydrazide compound, or a physiologically acceptable salt thereof according to claim 6, wherein $R^{11}$ is a phenyl group optionally substituted by hydroxy, $C_{1-6}$ alkyl or $C_{1-6}$ alkoxy, $R^{21}$ is a phenyl group optionally substituted by a group: —$Y^1$—$R^{71}$, $Y^1$ and $R^{71}$ are the same as defined in claim 5, and $Y^1$ is bound to the 3- or 4-position of the phenyl group.

9. A 2-furancarboxylic acid hydrazide compound selected from:

3,4-diphenyl-2-furancarboxylic acid 2-(3-cyano-4-hydroxybenzoyl)hydrazide, 3,4-diphenyl-2-furancarboxylic acid 2-(4-hydroxy-3-nitrobenzoyl)hydrazide, 3-[3-(2,3,5,6-tetramethylbenzyloxy)phenyl]-2-furancarboxylic acid 2-(3-cyano-4-hydroxybenzoyl)hydrazide, 3-[4-(2,3,5,6-tetramethylbenzyloxy)phenyl]-2-furancarboxylic acid 2-(3-cyano-4-hydroxybenzoyl)hydrazide, 3-[3-(2,3,5,6-tetramethylbenzyloxy)phenyl]-2-furancarboxylic acid 2-(4-hydroxy-3-nitrobenzoyl)hydrazide, 3-[4-(2,3,5,6-tetramethylbenzyloxy)phenyl]-2-furancarboxylic acid 2-(4-hydroxy-3-nitrobenzoyl)hydrazide, 4-phenyl-3-[3-(2,3,5,6-tetramethylbenzyloxy)phenyl]-2-furancarboxylic acid 2-(3-cyano-4-hydroxybenzoyl)hydrazide, 3-phenyl-4-[3-(2,3,5,6-tetramethylbenzyloxy)phenyl]-2-furancarboxylic acid 2-(3-cyano-4-hydroxybenzoyl)hydrazide, 4-phenyl-3-[3-(2,3,5,6-tetramethylbenzyloxy)phenyl]-2-furancarboxylic acid 2-(4-hydroxy-3-nitrobenzoyl)hydrazide, 3-(3-benzyloxyphenyl)-2-furancarboxylic acid 2-(3-cyano-4-hydroxybenzoyl)hydrazide, 3-(3-benzyloxyphenyl)-2-furancarboxylic acid 2-(4-hydroxy-3-nitrobenzoyl)hydrazide, 3-(3-phenoxyphenyl)-2-furancarboxylic acid 2-(3-cyano-4-hydroxybenzoyl)hydrazide, 3-(3-phenethyloxyphenyl)-2-furancarboxylic acid 2-(3-cyano-4-hydroxybenzoyl)hydrazide, 3-(3-phenethyloxyphenyl)-2-furancarboxylic acid 2-(4-hydroxy-3-nitrobenzoyl)hydrazide, 3-[3-(4-pyridylmethyloxy)phenyl]-2-furancarboxylic acid 2-(3-cyano-4-hydroxybenzoyl)hydrazide, 3-[3-(4-methylsulfonylbenzyloxy)phenyl]-2-furancarboxylic acid 2-(4-hydroxy-3-nitrobenzoyl)hydrazide, 3-[3-(4-methylsulfonylbenzyloxy)phenyl]-2-furancarboxylic acid 2-(3-cyano-4-hydroxybenzoyl)hydrazide, 3-phenyl-2-furancarboxylic acid 2-(3-cyano-4-hydroxybenzoyl)hydrazide, 3-phenyl-2-furancarboxylic acid 2-(4-hydroxy-3-nitrobenzoyl)hydrazide, 3-[3-(2-methylbenzyloxy)phenyl]-2-furancarboxylic acid 2-(4-hydroxy-3-nitrobenzoyl)hydrazide, 3-[3-(3-methylbenzyloxy)phenyl]-2-furancarboxylic acid 2-(4-hydroxy-3-nitrobenzoyl)hydrazide, 3-[3-(4-methylbenzyloxy)phenyl]-2-furancarboxylic acid 2-(4-hydroxy-3-nitrobenzoyl)hydrazide, 3-[3-(2,5-dimethylbenzyloxy)phenyl]-2-furancarboxylic acid 2-(4-hydroxy-3-nitrobenzoyl)hydrazide, 3-[3-(3,4-dimethylbenzyloxy)phenyl]-2-furancarboxylic acid 2-(4-hydroxy-3-nitrobenzoyl)hydrazide, 3-[3-(2,4-dimethylbenzyloxy)phenyl]-2-furancarboxylic acid 2-(4-hydroxy-3-nitrobenzoyl)hydrazide, 3-[3-(2-methylsulfonylaminobenzyloxy)phenyl]-2-furancarboxylic acid 2-(4-hydroxy-3-nitrobenzoyl)hydrazide, 3-(4-butylphenyl)-2-furancarboxylic acid 2-(4-hydroxy-3-nitrobenzoyl)hydrazide, 3-(3-methylphenyl)-2-furancarboxylic acid 2-(4-hydroxy-3-nitrobenzoyl)hydrazide, 3-(4-methylphenyl)-2-furancarboxylic acid 2-(4-hydroxy-3-nitrobenzoyl)hydrazide, 3-(3,4-dimethylphenyl)-2-furancarboxylic acid 2-(4-hydroxy-3-nitrobenzoyl)hydrazide, 3-(3-isopropylphenyl)-2-furancarboxylic acid 2-(4-hydroxy-3-nitrobenzoyl)hydrazide,
3-(4-isopropylphenyl)-2-furancarboxylic acid 2-(4-hydroxy-3-nitrobenzoyl)hydrazide,
3-(4-ethylphenyl)-2-furancarboxylic acid 2-(4-hydroxy-3-nitrobenzoyl)hydrazide,
3-(4-hexylphenyl)-2-furancarboxylic acid 2-(4-hydroxy-3-nitrobenzoyl)hydrazide,
3-(4-pentyloxyphenyl)-2-furancarboxylic acid 2-(4-hydroxy-3-nitrobenzoyl)hydrazide,
3-(4-propylphenyl)-2-furancarboxylic acid 2-(4-hydroxy-3-nitrobenzoyl)hydrazide,
3-(4-pentylphenyl)-2-furancarboxylic acid 2-(4-hydroxy-3-nitrobenzoyl)hydrazide,
3-[3-(2-methoxy-5-pyridylmethyloxy)phenyl]-2-furancarboxylic acid 2-(4-hydroxy-3-nitrobenzoyl)hydrazide,
3-[3-(4-methoxybenzyloxy)phenyl]-2-furancarboxylic acid 2-(4-hydroxy-3-nitrobenzoyl)hydrazide,
3-[3-(2-acetylaminobenzyloxy)phenyl]-2-furancarboxylic acid 2-(4-hydroxy-3-nitrobenzoyl)hydrazide,
3-(3-isopentyloxyphenyl)-2-furancarboxylic acid 2-(4-hydroxy-3-nitrobenzoyl)hydrazide,
3-(3-butoxyphenyl)-2-furancarboxylic acid 2-(4-hydroxy-3-nitrobenzoyl)hydrazide,
3-(3-pentyloxyphenyl)-2-furancarboxylic acid 2-(4-hydroxy-3-nitrobenzoyl)hydrazide,
3-(3-isobutoxyphenyl)-2-furancarboxylic acid 2-(4-hydroxy-3-nitrobenzoyl)hydrazide,
3-(3-hexyloxyphenyl)-2-furancarboxylic acid 2-(4-hydroxy-3-nitrobenzoyl)hydrazide,
3-(3-heptyloxyphenyl)-2-furancarboxylic acid 2-(4-hydroxy-3-nitrobenzoyl)hydrazide,
3-(3-hexylphenyl)-2-furancarboxylic acid 2-(4-hydroxy-3-nitrobenzoyl)hydrazide,
3-(3-benzylphenyl)-2-furancarboxylic acid 2-(4-hydroxy-3-nitrobenzoyl)hydrazide,
3-(3-pentylphenyl)-2-furancarboxylic acid 2-(4-hydroxy-3-nitrobenzoyl)hydrazide,
3-[3-(3-methyl-2-butenyloxy)phenyl]-2-furancarboxylic acid 2-(4-hydroxy-3-nitrobenzoyl)hydrazide,
3-[3-(2-methyl-2-propenyloxy)phenyl]-2-furancarboxylic acid 2-(4-hydroxy-3-nitrobenzoyl)hydrazide,
3-[3-(2-butenyloxy)phenyl]-2-furancarboxylic acid 2-(4-hydroxy-3-nitrobenzoyl)hydrazide, and
3-[3-(2-allyloxy)phenyl]-2-furancarboxylic acid 2-(4-hydroxy-3-nitrobenzoyl) hydrazide, or a physiologically acceptable salt thereof.

10. A pharmaceutical composition comprising:
a therapeutically effective amount of the 2-furancarboxylic acid hydrazide compound or a prodrug, physiologically acceptable salt, hydrate or solvate according to any one of claims 1 to 9, thereof; and a pharmaceutically accepted carrier.

11. The pharmaceutical composition according to claim 10 for use in a treatment of a symptom or disease selected from hyperglycemia, abnormal glucose tolerance, insulin resistance syndrome, syndrome X, type I diabetes, type II diabetes, hyperlipidemia, hypertriglyceridemia, glucagonoma, obesity, diabetes caused by obesity, and diabetic complications.

12. A method for treating a symptom or disease selected from hyperglycemia, abnormal glucose tolerance, insulin resistance syndrome, syndrome X, type I diabetes, type II diabetes, hyperlipidemia, hypertriglyceridemia, glucagonoma, obesity, diabetes caused by obesity, and diabetic complications, comprising the step of administering an effective amount of the 2-furancarboxylic acid hydrazide compound according to any one of claims 1 to 9, or a physiologically acceptable salt thereof as an active ingredient into a mammal in need of such treatment of the symptom and disease selected from hyperglycemia, abnormal glucose tolerance, insulin resistance syndrome, syndrome X, type I diabetes, type II diabetes, hyperlipidemia, hypertriglyceridemia, glucagonoma obesity, diabetes caused by obesity, and diabetic complications.

13. A 2-furancarboxylic acid hydrazide compound according to claim 9, which is 3-(4-hexylphenyl)-2-furancarboxylic acid 2-(4-hydroxy-3-nitrobenzoyl)hydrazide.

14. A 2-furancarboxylic acid hydrazide compound according to claim 9, which is 3-(4-pentyloxyphenyl)-2-furancarboxylic acid 2-(4-hydroxy-3-nitrobenzoyl)hydrazide.

15. A 2-furancarboxylic acid hydrazide compound according to claim 9, which is 3-(4-propylphenyl)-2-furancarboxylic acid 2-(4-hydroxy-3-nitrobenzoyl)hydrazide.

* * * * *

UNITED STATES PATENT AND TRADEMARK OFFICE
CERTIFICATE OF CORRECTION

PATENT NO. : 7,514,452 B2  
APPLICATION NO. : 10/503215  
DATED : April 7, 2009  
INVENTOR(S) : Fujii et al.

Page 1 of 1

It is certified that error appears in the above-identified patent and that said Letters Patent is hereby corrected as shown below:

On the title page, item (73), Assignee, please delete "Dianippon Pharmaceutical Co., Ltd." and insert therefore --Dainippon Sumitomo Pharma Co., Ltd.--.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,514,452 B2
APPLICATION NO. : 10/503215
DATED : April 7, 2009
INVENTOR(S) : Fujii et al.

It is certified that error appears in the above-identified patent and that said Letters Patent is hereby corrected as shown below:

Title page (Item 54, Title), please delete "HYDRAZIDES" and insert therefore, --HYDRAZIDE COMPOUNDS--.

At column 1, line 1 (Title), please delete "HYDRAZIDES" and insert therefore, --HYDRAZIDE COMPOUNDS--.

At column 4, line 6, please delete "—$(CH_2)_1$ $OR^{16}$," and insert therefore, -- —$(CH_2)_1OR^{16}$,--.

At column 4, line 9 (approx), please delete "—O $(CH_2)_1CO_2R^{18}$," and insert therefore, -- —$O(CH_2)_1CO_2R^{18}$,--.

At column 4, line 57 (approx), please delete "$(CH_2)_yOR^{29}$, $(CH_2)_yNR^{29}R^{30}$," and insert therefore, -- —$(CH_2)_yOR^{29}$, —$(CH_2)_yNR^{29}R^{30}$,--.

At column 5, line 42, please delete "aforedmentioned" and insert therefore, --aforementioned--.

At column 15, line 38, please delete "alkylgroup" and insert therefore, --alkyl group--.

At column 19, line 9, please delete "nitro benzoyl" and insert therefore, --nitrobenzoyl--.

At column 26, line 60, please delete "unsabstituted" and insert therefore, --unsubstituted--.

At column 27, line 55, please delete "(Perkin Elmer" and insert therefore, --(PerkinElmer--.

At column 30, line 53, please delete "mitiglinid)," and insert therefore, --mitiglinide),--.

At column 33, lines 25-26, please delete "4-methoxyphenylbronic acid" and insert therefore, --4-methoxyphenylboronic acid--.

UNITED STATES PATENT AND TRADEMARK OFFICE
CERTIFICATE OF CORRECTION

PATENT NO. : 7,514,452 B2
APPLICATION NO. : 10/503215
DATED : April 7, 2009
INVENTOR(S) : Fujii et al.

It is certified that error appears in the above-identified patent and that said Letters Patent is hereby corrected as shown below:

At column 33, line 48, please delete "carring" and insert therefore, --carrying--.

At column 45, line 67, please delete "(7.3 g)." and insert therefore, --(7.3 g)--.

At column 66, line 25, please delete "l(b)" and insert therefore, --1(b)--.

At column 80, line 4, please delete "2furancarboxylic" and insert therefore, --2-furancarboxylic--.

At column 86, line 60, please delete "carring" and insert therefore, --carrying--.

At column 88, line 60, please delete "carring" and insert therefore, --carrying--.

At Claim 1, column 96, line 31, please delete "disubstituted" and insert therefore, --di-substituted--.

At Claim 2, column 97, line 1, please delete "disubstituted" and insert therefore, --di-substituted--.

At Claim 2, column 97, line 4, please delete "$C_{2-6}$" and insert therefore, --$C_{1-6}$--.

At Claim 2, column 97, line 65, please delete "$C_{3-7}$" and insert therefore, --$C_{3-7}$--.

At Claim 9, column 102, line 4, please delete "nitrobenzoyl) hydrazide," and insert therefore, --nitrobenzoyl)hydrazide,--.

UNITED STATES PATENT AND TRADEMARK OFFICE
CERTIFICATE OF CORRECTION

PATENT NO. : 7,514,452 B2
APPLICATION NO. : 10/503215
DATED : April 7, 2009
INVENTOR(S) : Fujii et al.

It is certified that error appears in the above-identified patent and that said Letters Patent is hereby corrected as shown below:

At Claim 13, column 102, line 32, please delete "glucagonoma" and insert therefore, --glucagonoma,--.

Signed and Sealed this

First Day of December, 2009

David J. Kappos
*Director of the United States Patent and Trademark Office*